US012715885B2

United States Patent
(12) United States Patent
Zhang et al.

(10) Patent No.: US 12,715,885 B2
(45) Date of Patent: Aug. 25, 2026

(54) CHIRAL SYNTHONS FOR THE SYNTHESIS OF CHIRAL PHOSPHOROTHIOATES

(71) Applicant: Boehringer Ingelheim International GmbH, Ingelheim am Rhein (DE)

(72) Inventors: Yongda Zhang, Sandyhook, CT (US); Linglin Wu, Brookfield, CT (US)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 387 days.

(21) Appl. No.: 18/281,047

(22) PCT Filed: Mar. 16, 2022

(86) PCT No.: PCT/EP2022/056805
§ 371 (c)(1),
(2) Date: Sep. 8, 2023

(87) PCT Pub. No.: WO2022/194924
PCT Pub. Date: Sep. 22, 2022

(65) Prior Publication Data

US 2025/0115629 A1 Apr. 10, 2025

(30) Foreign Application Priority Data

Mar. 18, 2021 (EP) .................................... 21163531

(51) Int. Cl.
*C07F 9/58* (2006.01)
*C07H 1/02* (2006.01)
*C07H 19/10* (2006.01)
*C07H 19/20* (2006.01)
*C07H 21/04* (2006.01)

(52) U.S. Cl.
CPC ................. *C07F 9/58* (2013.01); *C07H 1/02* (2013.01); *C07H 19/10* (2013.01); *C07H 19/20* (2013.01); *C07H 21/04* (2013.01)

(58) Field of Classification Search
CPC .. C07F 9/58; C07H 1/02; C07H 19/10; C07H 19/20; C07H 21/04
See application file for complete search history.

(56) References Cited

U.S. PATENT DOCUMENTS

2019/0322694 A1 10/2019 Schmidt et al.

FOREIGN PATENT DOCUMENTS

WO 2006066260 A2 6/2006
WO 2015107425 A2 7/2015

OTHER PUBLICATIONS

Almer et al., "A new approach to stereospecific synthesis of P-chiral phosphorothioates. Preparation of diastereomeric dithymidyl-(3'-5') phosphorothioates", Chemical Communications, 2004, vol. 7, No. 3, pp. 290-291.
Almer et al., "A new approach to stereospecific synthesis of P-chiral phosphorothioates. Preparation of diastereomeric dithymidyl-(3A-5A) phosphorothioates", Chem. Comm., 2004, vol. 290, pp. 290-291.
Bergman et al., "Hydrolysis of the vinyl ether functional group in a model for Prostacyclin in Which the Carboxyl Group Has Been Replaced by a Pyridine Ring", J. Org. Chem., 1989, vol. 54, p. 2137-2142.
Boekelheide et al., "Muscular Relaxant Drugs. Some Substituted Pyridyl Ketones", Journal of the American Chemical Society, 1951, vol. 73, pp. 2356-2357.
Condon et al.; "Nickel Catalyzed Electrochemical Heteroarylation of Activated Olefins", Synthesis, 2002, vol. 12, pp. 1752-1758.
Efimov et al., "Approach to the Synthesis of Natural and Modified Oligonucleotides by the Phosphotriester Method Using O-Nucleophilic Intramolecular Catalysis", Nucleosides, Nucleotides & Nucleic Acids, 2007, vol. 26, No. 8-9, pp. 1087-1093.
Featherston et al., "Catalytic asymmetric and stereodivergent oligonucleotide synthesis", Science, 2021, vol. 371, No. 6530, pp. 702-707.
International Search Report and Written Opintion for application PCT/EP2022/056805, date of mailing Jun. 20, 2022.
Knouse et al., "Unlocking P(V): Reagents for chiral phosphorothioate synthesis", Science 2018, vol. 361, pp. 1234-1238.
Nukaga et al., "Stereocontrolled Solid-Phase Synthesis of Phosphate/ Phosphorothioate (PO/PS) Chimeric Oligodeoxyribonucleotides on an Automated Synthesizer Using an Oxazaphospholidine-Phosphoramidite Method", J. Org. Chem., 2016, vol. 81, pp. 2753-2762.
Reyes et al., "Iridium-Catalyzed Asymmetric Borylation of Unactivated Methylene C($sp^3$)-H Bonds", Am. Chem. Soc., 2019, vol. 141, pp. 6817?6821.
Stec et al., "Diastereomers of Nucleoside 3'-0-(2-Thio-1,3,2-oxathia(selena)phospholanes): Building Blocks for Stereocontrolled Synthesis of 01igo(nucleoside phosphorothioate)s", J. Am. Chem. Soc., 1995, vol. 117, pp. 12019-12029.
Wada et al., "An Oxazaphospholidine Approach for the Stereocontrolled Synthesis of Oligonucleoside Phosphorothioates", J. Am. Chem. Soc., 2003, vol. 125, pp. 8307-8317.

(Continued)

*Primary Examiner* — Alicia L Otton

(74) *Attorney, Agent, or Firm* — Robin L. Teskin; Baker, Donelson, Bearman, Caldwell & Berkowitz PC

(57) ABSTRACT

This invention relates to compounds of Formula (I) useful as synthons for a general synthetic method for making chiral phosphorothioates, to their preparation and to their use in a robust large scale process for making P-chiral phosphorothioates.

(I)

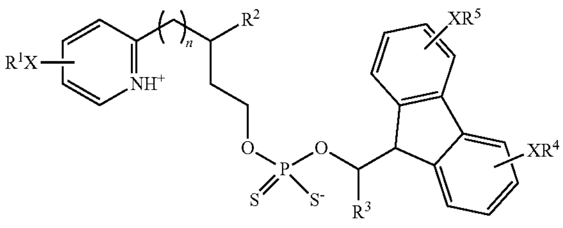

16 Claims, No Drawings

(56) References Cited

OTHER PUBLICATIONS

Wada et al., "Solid-Phase Synthesis of Stereoregular Oligodeoxyribonucleoside Phosphorothioates Using Bicyclic Oxazaphospholidine Derivatives as Monomer Units", J. Am. Chem. Soc., 2008, vol. 130, pp. 16031-16037.
Weickgenannt et al., "Catalytic Asymmetric Si—O Coupling of Simple Achiral Silanes and Chiral Donor-Functionalized Alcohols", Angewandte Chemie, International Edition 2010, vol. 49, No. 12, pp. 2223-2226.

CHIRAL SYNTHONS FOR THE SYNTHESIS OF CHIRAL PHOSPHOROTHIOATES

FIELD OF THE INVENTION

This invention relates to novel compounds useful as synthons for a general synthetic method for making chiral phosphorothioates, to their preparation and to their use in a robust large scale process for making P-chiral phosphorothioates.

BACKGROUND OF THE INVENTION

P-chiral phosphorothioate linkages have been widely implanted in the biologically active oligodeoxyribonucleotides and oligoribonuleotides. Traditionally, P-chiral phosphoro-thioates were synthesized in a few steps including (1) coupling of a P(III)-based phosphoramidite with the first nucleoside,
(2) coupling with the second nucleoside,
(3) sulfurization, and
(4) deprotection.

Scheme A Strategy for Synthesis of P-chiral phosphorothioates

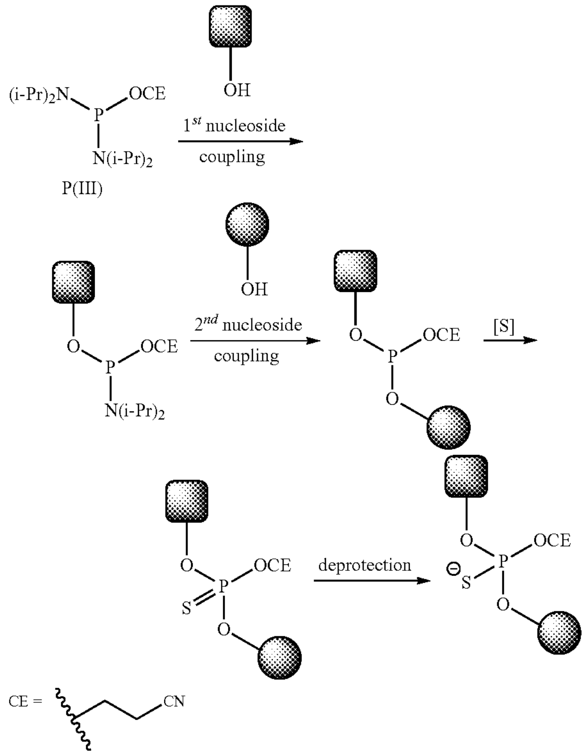

The strategies have been widely studied, as exemplified by T. Wada et al., *J. Am. Chem. Soc.*, 2003, 125, 8307-8317; T. Wada et al., *J. Am. Chem. Soc.*, 2008, 130, 16031-16037; T. Wada et al., *J. Org. Chem.*, 2016, 81, 2753-2762; WO 2015/107425. However, this method involves labile intermediates associated with P(III) and multiple-step synthesis of the chiral auxiliary. More recently, catalytic asymmetric and stereodivergent synthesis of oligonucleotide with chiral phosphorothioate linkage via P(III) intermediates was reported (Aaron L. Featherston, Yongseok Kwon, Matthew M. Pompeo, Oliver D. Engl, David K. Leahy, Scott J. Miller *Science,* 2021, 371, 702-707).

Scheme B
Synthesis of chiral Dithymidine Phosphorothioates according to Wada et al.

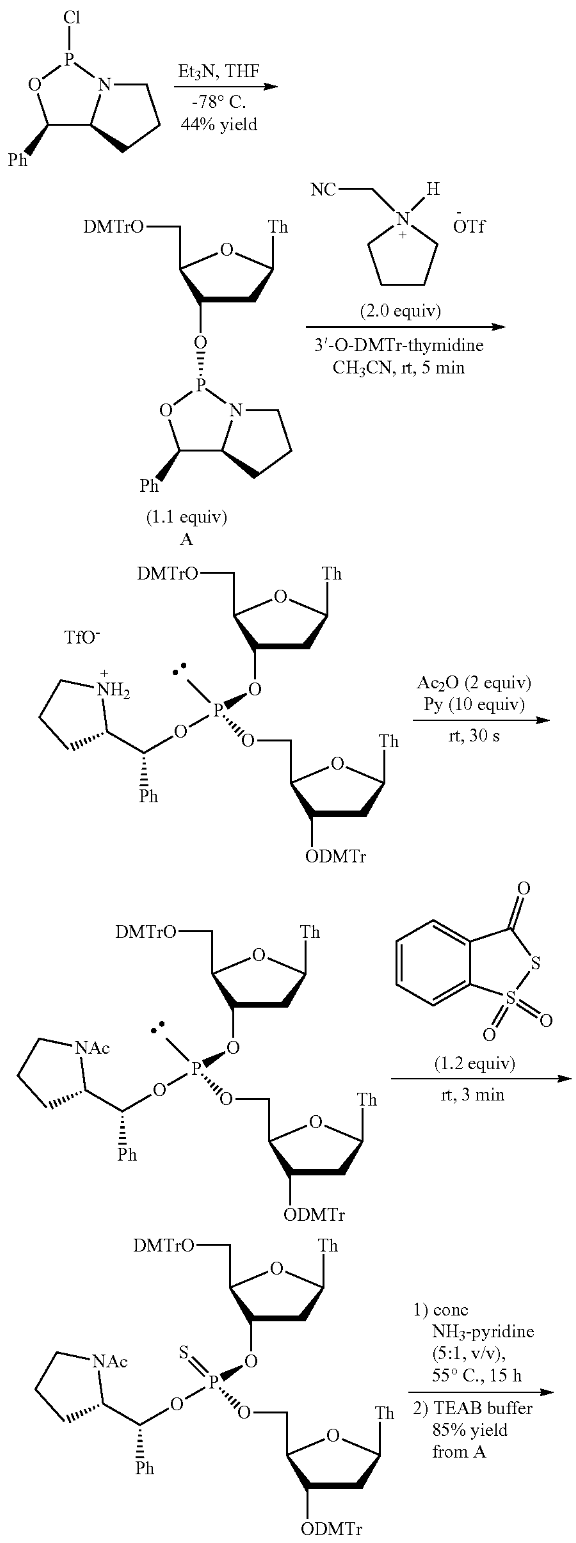

-continued

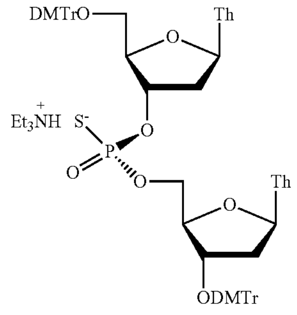

dr > 99.5:0.5

(Ph = phenyl;
THF = tetrahydrofuran;
OTf = trifluoromethylsulfonyl;
Th = Thymidine;
DMTr = dimethoxytrityl;
Ac = actetyl;
Py = pyridine;
TEAB = triethylammonium bicarbonate)

A first method for stereochemically controlled chemical synthesis of PS-Oligos (Phosphorothioate analogs of oligonucleotides) involving P(III)-oxathiophospholanes was developed by Stec et al. (Wojciech J. Stec, Andrzej Grajkowski, Anna Kobylafiska, Boledaw Karwowski, Maria KozioHciewicz, Konrad Misiura, Andnej Okruszek, Andrzej Wilk, Piotr Guga, and Mdgonata Boczkowska, *J. Am. Chem. Soc.* 1995, 117, 12019-12029). However, this approach is scale-limited and suffers from poor coupling efficiency. Meanwhile, the strategy involves the resolution of the chiral P(V)-oxathiophospholane sulfides with the sacrifice of one nucleoside.

Scheme C
Stereochemically controlled synthesis of PS-Oligos according to Stec et al.

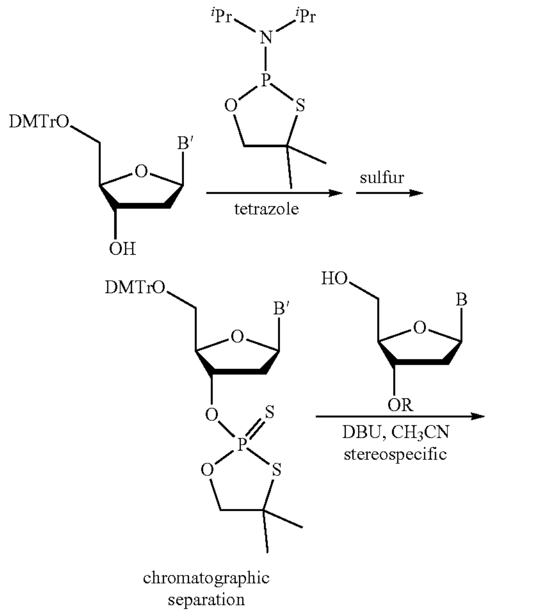

-continued

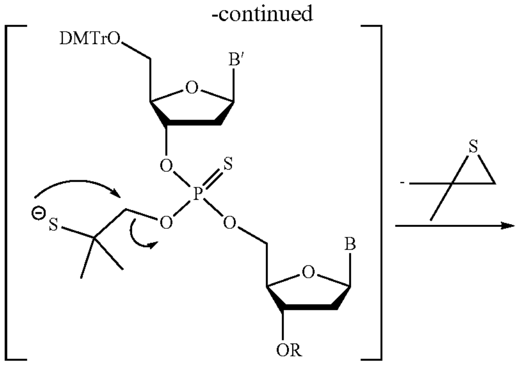

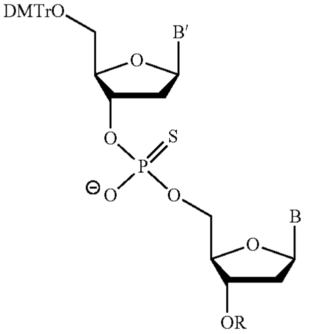

(DMTr = dimethoxytrityl;
$^{i}$Pr = isopropyl;
DBU = 1,8-diazabicyclo[5.4.0]undex-7-ene;
R = Ac or R = -$COCH_2CH_2CO$-LCA-CPG;
B′ = Thy, $Ade^{Bz}$, $Cyt^{Bz}$ or $Gua^{iBu, DPC}$;
B = Thy, Ade, Cyt or Gua;
R = Ac or R = -COCH CH CO-LCA-CPG;
LCA CPG = long chain alkylamine controlled pore glass)

To overcome the issues mentioned above, a novel bench-stable chiral P(V)-based reagent abbreviated as Ψ (PSI=phosphorus-sulfur incorporation) was invented recently (Kyle W. Knouse, Justine N. deGruyter, Michael A. Schmidt, Bin Zheng, Julien C. Vantourout, Cian Kingston, Stephen E. Mercer, Ivar M. Mcdonald, Richard E. Olson, Ye Zhu, Chao Hang, Jason Zhu, Changxia Yuan, Qinggang Wang, Peter Park, Martin D. Eastgate, Phil S. Baran *Science* 2018, 361, 1234-1238) for diastereoselective introduction of phosphorus-sulfur, which significantly increases the process efficiency and provides huge benefits such as simple operation and easy scale-up. The applications of the reagent system were demonstrated in the stereocontrolled syntheses of dideoxyribonucleosides, which were prepared as a single diastereomer in 50-88% yields from the protected nucleoside monomers. The chemistry required the very strong base DBU (Pka=24.34 conjugate acid in acetonitrile) as the sole base to effect the elongation of an oligonucleotidic chain, which limits the flexibility of choice of protecting groups for the nucleosides especially for ribonucleosides. Besides, the synthesis of oligoribonuleotide was not fully demonstrated.

Scheme D Synthesis and use of reagent ψ

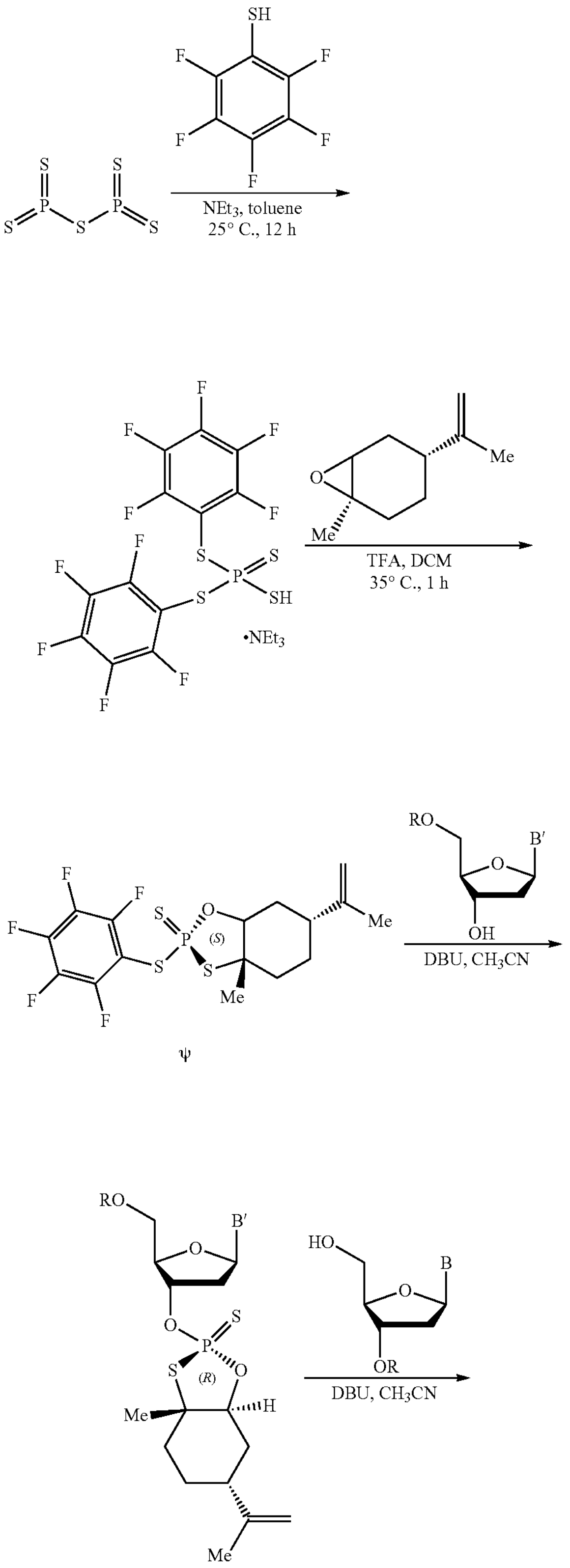

-continued

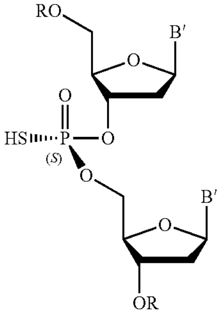

(DCM = dichloromethane;
Et = ethyl;
Me = methyl;
TFA = trifluoroacetic acid;
B = Thy, $Ade^{Bz}$, $Cyt^{Bz}$ or $Gua^{iBu}$;
B' = Thy, $Ade^{Bz}$, $Cyt^{Bz}$ or $Gua^{iBu}$;
R = TBDPS = tert-butyldiphenylsilyl)

In 2004, Stawinski and co-workers developed an alternative approach for stereospecific synthesis of P-chiral phosphorothioates by manipulation of a P(V)-based intermediate based on intramolecular nucleophile catalysis of pyridine N-oxide (J. Stawinski et al., *Chem. Comm.* 2004, 290-291; WO 2006/066260). This strategy improved the coupling reaction kinetics and prevented epimerization at the P-center. However, the approach requires column chromatography to separate the diastereomerical intermediates with the sacrifice of one nucleoside and makes it impractical for further elongation to introduce a second P-chiral phosphorothioate. Moreover, the production 4-methoxy-2-pyridinemethanol-1-oxide on large scale and its stability under the reaction conditions present a huge challenge and prevent the approach from wide application.

To address and circumvent the aforementioned limitations and other challenges connected with the formation of P-chiral phosphorothioates, the development of robust and cost-effective methods is still highly desirable in the field of nucleotide world.

AIM OF THE PRESENT INVENTION

The aim of the present invention is to provide new compounds, in particular new synthons, which are useful for the synthesis of P-chiral phosphorothioates.

A further aim of the present invention is to provide new compounds, in particular new synthons, which are useful for the large scale synthesis of P-chiral phosphorothioates.

A further aim of the present invention is to provide a process for the synthesis of stereoenriched nucleotides such as oligodeoxyribonucleotides and oligoribonuleotides using the new compounds.

A further aim of the present invention is to provide methods for the synthesis of the new compounds, in particular P-chiral synthons.

A further aim of the present invention is to provide starting and/or intermediate compounds suitable in methods for the synthesis of the new compounds containing one or more P-stereogenic centers.

Further aims of the present invention become apparent to the one skilled in the art by the description hereinbefore and in the following and by the examples.

OBJECT OF THE INVENTION

Within the scope of the present invention, it has now surprisingly been found that the new compounds of general formula (I) as described hereinafter are useful as chiral synthons that overcome the problems of the prior art. They are stable, and well characterized in that that they are P(V)-based orthogonally protected chiral phosphorothioates, bearing a fluorenylmethyl group and a pyridinyl group on a chiral alcohol. They allow the precise construction of stereoenriched nucleotides in a stereoselective and predictable manner, and simultaneously provide the possibility to prepare either one of the diastereomers by changing the coupling order or switching to the other diastereomer of the synthon. As a consequence, either diastereomer of the P-stereogenic nucleotide can be prepared in a simple manner, i.e. without column chromatography. This makes the claimed synthons fit for large scale use.

In a first aspect, the present invention provides compounds of formula (I)

(I)

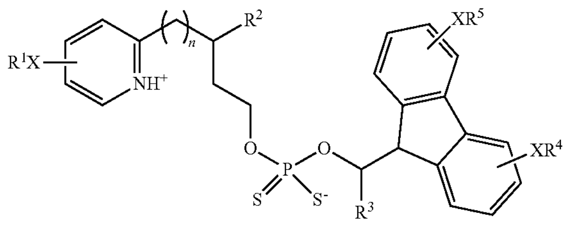

wherein n is 0, 1, 2, 3, 4, 5, or 6;

each X is selected from the group X-G1 consisting of a bond;

$—(CH_2)_m—$ optionally substituted with halogen, —CN, $C_{1-3}$alkyl or —O—$C_{1-3}$alkyl;

O;

$NR^N$ and

S;

wherein m is 1, 2, 3 or 4, and wherein $R^N$ is selected from the group $R^N$-G1 consisting of H and $C_{1-3}$alkyl;

$R^1$ is selected from the group $R^1$-G1 consisting of H, $C_{1-6}$alkyl, $C_{3-6}$cycloalkyl, $—CH_2—C_{3-10}$cycloalkyl, aryl, $—CH_2$-aryl, and heteroaryl, wherein each aryl and heteroaryl group is optionally substituted with 1-3 substituents selected from the group consisting of halogen, —CN, $C_{1-3}$alkyl and —O—$C_{1-3}$alkyl;

$R^2$ is selected from the group $R^2$-G1 consisting of $C_{1-4}$alkyl, —C(O)OR$^6$, and aryl, wherein each alkyl group of $R^2$ is optionally substituted with one or more substituents independently selected from halogen, cyano, and trimethylsilyl, and wherein $R^6$ is selected from the group consisting of $C_{1-4}$alkyl;

$R^3$ is selected from the group $R^3$-G1 consisting of H, $C_{1-6}$alkyl, $C_{3-6}$cycloalkyl, $—CH_2—C_{3-10}$cycloalkyl, aryl, $—CH_2$-aryl, and heteroaryl, wherein each aryl and heteroaryl group is optionally substituted with 1-3 substituents selected from the group consisting of halogen, —CN, $C_{1-3}$alkyl and —O—$C_{1-3}$alkyl; and $R^4$ and $R^5$ are each independently of each other selected from the group $R^4$-G1 consisting of H, $C_{1-6}$alkyl, $C_{3-6}$cycloalkyl, $—CH_2—C_{3-10}$cycloalkyl, aryl, $—CH_2$-aryl, and heteroaryl, wherein each aryl and heteroaryl group is optionally substituted with 1-3 substituents selected from the group consisting of halogen, —CN, $C_{1-3}$alkyl and —O—$C_{1-3}$alkyl;

or a tautomer, stereoisomer or salt thereof.

In a further aspect, the present invention relates to processes for preparing a compounds of general formula (I) and to new intermediate compounds in these processes.

A further aspect of the invention relates to a salt of the compounds of general formula (I) according to this invention.

According to another aspect of the invention, there is provided the use of a compound of the general formula (I) in the synthesis of P-chiral phosphorothioates, particularly in large scale synthesis of P-chiral phosphorothioates.

According to another aspect of the invention, there is provided a process for the synthesis of stereoenriched nucleotides, such as oligodeoxyribonucleotides and oligoribonuleotides, using the new compounds of formula (I).

Other aspects of the invention become apparent to the one skilled in the art from the specification and the experimental part as described hereinbefore and hereinafter.

The compounds of formula (I) were prepared easily from readily available and economic raw materials such as (9H-fluoren-9-yl)methanol and picolinic acid.

The compounds of formula (I) as useful as synthons for a general synthetic method that provides access to chiral phosphorothioates and allows the effective preparation of P-chiral phosphorothioate linkages in oligodeoxyribonucleotides or more synthetically complicated oligoribonuleotides through simple operations with predicable stereochemistry, offering a new avenue to access P-chiral phosphorothioates under mild conditions and enabling the stereospecific synthesis of P-chiral phosphorothioates efficiently on large scale. The compounds of formula (I) are also useful as synthons in the synthesis of cyclic dinucleotides (also abbreviated as CDN), an important class of compounds with interesting biologically activities.

DETAILED DESCRIPTION OF THE INVENTION

Unless otherwise stated, the groups, residues, and substituents, particularly n, X, $R^1$, $R^2$, $R^3$ and $R^4$, are defined as above and hereinafter. If residues, substituents or groups occur several times in a compound, they may have the same or different meanings. Some preferred meanings of individual groups and substituents of the compounds according to the invention will be given hereinafter. Any and each of these definitions may be combined with each other.

X:

X-G1:

The group X is preferably selected from the group X-G1 as defined above.

X-G2:

In another embodiment, each group X is selected from the group X-G2 consisting of a bond;

$—(CH_2)—$ optionally substituted with —H, halogen, —CN, $—CH_3$ or $—O—CH_3$;

O;

$NR^N$; and

S;

wherein $R^N$ is selected from the group $R^N$-G2 consisting of H and $—CH_3$.

X-G3:

In another embodiment, each group X is selected from the group X-G3 consisting of a bond, O, NH, $NCH_3$ and S.

X-G4:

In another embodiment, each group X is selected from the group X-G4 consisting of a bond, O, NH and S.

X-G5a:

In another embodiment, each group X is selected from the group X-G5a consisting of a bond and O.

X-G5b:

In another embodiment, each group X is selected from the group X-G5b consisting of S and O.

X-G6:

In another embodiment the group X is selected from the group X-G6 consisting of O.

$R^1$:

$R^1$-G1:

The group $R^1$ is preferably selected from the group $R^1$-G1 as defined above.

$R^1$-G2:

In one embodiment the group $R^1$ is selected from the group $R^1$-G2 consisting of H, $C_{1-6}$alkyl, $C_{3-6}$cycloalkyl, —$CH_2$—$C_{3-10}$cycloalkyl, and —$CH_2$-phenyl, wherein the phenyl group is optionally substituted with 1-3 substituents selected from the group consisting of halogen, —CN, $CH_3$ and —O—$CH_3$.

$R^1$-G3:

In one embodiment the group $R^1$ is selected from the group $R^1$-G3 consisting of H, $C_{1-4}$alkyl, —$CH_2$—$C_{3-6}$cycloalkyl, and —$CH_2$-phenyl, wherein the phenyl group is optionally substituted with 1-3 substituents selected from the group consisting of halogen, —CN, $CH_3$ and —O—$CH_3$.

$R^1$-G4:

In one embodiment the group $R^1$ is selected from the group $R^1$-G4 consisting of H and $C_{1-4}$alkyl.

$R^1$-G5:

In another embodiment the group $R^1$ is selected from the group $R^1$-G5 consisting of $C_{1-3}$-alkyl.

$R^2$:

$R^2$-G1:

The group $R^2$ is preferably selected from the group $R^2$-G1 as defined above.

$R^2$-G2:

In one embodiment the group $R^2$ is selected from the group $R^2$-G2 consisting of $C_{1-4}$alkyl optionally substituted with one or more F, or with one substituent selected from Cl, Br, cyano, and trimethylsilyl.

$R^2$-G3:

In one embodiment the group $R^2$ is selected from the group $R^2$-G3 consisting of $C_{1-3}$alkyl optionally substituted with one or more F.

$R^2$-G4:

In one embodiment the group $R^2$ is selected from the group $R^2$-G4 consisting of $C_{1-2}$alkyl optionally substituted with one to three F.

$R^2$-G5:

In one embodiment the group $R^2$ is selected from the group $R^2$-G5 consisting of $C_{1-2}$alkyl.

$R^2$-G6:

In another embodiment the group $R^2$ is selected from the group $R^2$-G6 consisting of $CH_3$.

$R^3$-G1:

The group $R^3$ is preferably selected from the group $R^3$-G1 as defined above.

$R^3$-G2:

In one embodiment the group $R^3$ is selected from the group $R^3$-G2 consisting of H and $C_{1-3}$alkyl.

$R^3$-G3:

In another embodiment the group $R^3$ is selected from the group $R^3$-G3 consisting of H.

$R^4$;

$R^4$-G1:

The group $R^4$ is preferably selected from the group $R^4$-G1 as defined above.

$R^4$-G2:

In one embodiment, the group $R^4$ is selected from the group $R^4$-G2 consisting of H and $C_{1-3}$alkyl.

$R^4$-G3

In another embodiment the group $R^4$ is selected from the group $R^4$-G3 consisting of H.

$R^5$:

$R^4$-G1=$R^5$-G1:

The group $R^5$ is preferably selected from the group $R^4$-G1 as defined above.

$R^5$-G2:

In one embodiment, the group $R^5$ is selected from the group $R^5$-G2 consisting of H and $C_{1-3}$alkyl.

$R^5$-G3

In another embodiment the group $R^5$ is selected from the group $R^5$-G3 consisting of H.

n:

n is an integer selected from 0, 1, 2, 3, 4, 5 and 6.

Preferably, n is selected from 0, 1, 2 and 3.

More preferably, n is 0 or 1.

Most preferably, n is 0.

The following preferred embodiments of compounds of the formula (I) are described using generic formulae (I.1) to (I.3b), wherein any salts thereof are encompassed.

I.1

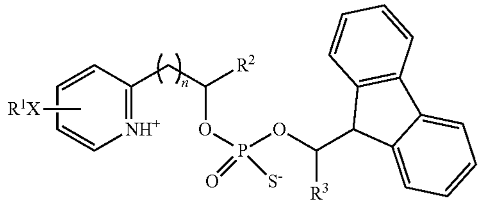

I.2

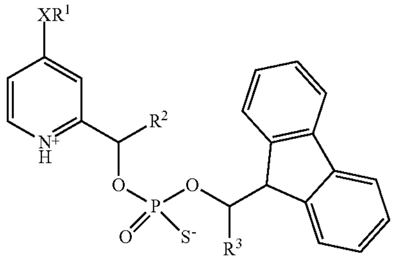

I.2a

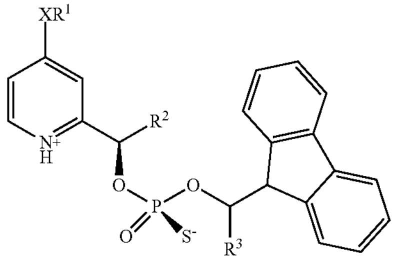

-continued

I.2b

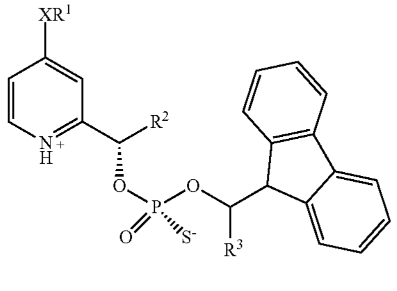

I.3

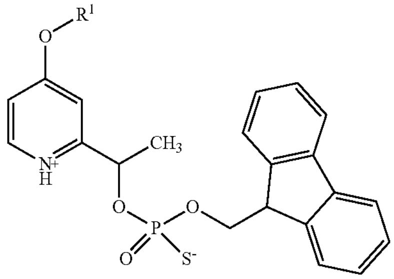

-continued

I.3a

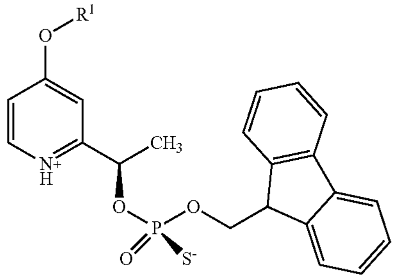

I.3b

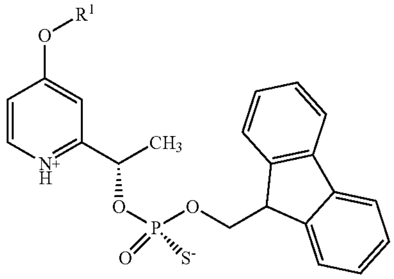

In of the above formulae (I.1) to (I.3b), n and the groups X, $R^1$, $R^2$ and $R^3$ are as defined above.

Examples of preferred subgeneric embodiments (E) according to the present invention are set forth in the following table, wherein each substituent group of each embodiment is defined according to the definitions set forth above:

| Embodiment | Formula | n | X | $R^1$ | $R^2$ | $R^3$ | $R^4$ | $R^5$ |
|---|---|---|---|---|---|---|---|---|
| E1 | I | 0 to 6 | X-G1 | $R^1$-G1 | $R^2$-G1 | $R^3$-G1 | $R^4$-G1 | $R^5$-G1 |
| E2 | I | 0, 1, 2, 3 | X-G2 | $R^1$-G2 | $R^2$-G2 | $R^3$-G2 | $R^4$-G2 | $R^5$-G2 |
| E3 | I | 0 or 1 | X-G2 | $R^1$-G2 | $R^2$-G2 | $R^3$-G3 | $R^4$-G3 | $R^5$-G3 |
| E4 | I | 0 or 1 | X-G3 | $R^1$-G2 | $R^2$-G2 | $R^3$-G2 | $R^4$-G2 | $R^5$-G2 |
| E5 | I | 0 or 1 | X-G3 | $R^1$-G3 | $R^2$-G2 | $R^3$-G2 | $R^4$-G2 | $R^5$-G2 |
| E6 | I | 0 or 1 | X-G3 | $R^1$-G3 | $R^2$-G2 | $R^3$-G3 | $R^4$-G3 | $R^5$-G3 |
| E7 | I | 0 or 1 | X-G3 | $R^1$-G4 | $R^2$-G3 | $R^3$-G2 | $R^4$-G2 | $R^5$-G2 |
| E8 | I | 0 or 1 | X-G3 | $R^1$-G4 | $R^2$-G3 | $R^3$-G3 | $R^4$-G3 | $R^5$-G3 |
| E9 | I | 0 | X-G3 | $R^1$-G4 | $R^2$-G3 | $R^3$-G2 | $R^4$-G2 | $R^5$-G2 |
| E10 | I | 0 | X-G3 | $R^1$-G4 | $R^2$-G3 | $R^3$-G3 | $R^4$-G3 | $R^5$-G3 |
| E11 | I | 0 or 1 | X-G4 | $R^1$-G2 | $R^2$-G2 | $R^3$-G2 | $R^4$-G2 | $R^5$-G2 |
| E12 | I | 0 or 1 | X-G4 | $R^1$-G3 | $R^2$-G2 | $R^3$-G2 | $R^4$-G2 | $R^5$-G2 |
| E13 | I | 0 or 1 | X-G4 | $R^1$-G3 | $R^2$-G2 | $R^3$-G3 | $R^4$-G3 | $R^5$-G3 |
| E14 | I | 0 or 1 | X-G4 | $R^1$-G4 | $R^2$-G3 | $R^3$-G2 | $R^4$-G2 | $R^5$-G2 |
| E15 | I | 0 or 1 | X-G4 | $R^1$-G4 | $R^2$-G3 | $R^3$-G3 | $R^4$-G3 | $R^5$-G3 |
| E16 | I | 0 | X-G4 | $R^1$-G4 | $R^2$-G3 | $R^3$-G2 | $R^4$-G2 | $R^5$-G2 |
| E17 | I | 0 | X-G4 | $R^1$-G4 | $R^2$-G3 | $R^3$-G3 | $R^4$-G3 | $R^5$-G3 |
| E18 | I | 0 or 1 | X-G5a | $R^1$-G2 | $R^2$-G2 | $R^3$-G2 | $R^4$-G2 | $R^5$-G2 |
| E19 | I | 0 or 1 | X-G5a | $R^1$-G3 | $R^2$-G2 | $R^3$-G2 | $R^4$-G2 | $R^5$-G2 |
| E20 | I | 0 or 1 | X-G5a | $R^1$-G3 | $R^2$-G2 | $R^3$-G3 | $R^4$-G3 | $R^5$-G3 |
| E21 | I | 0 or 1 | X-G5a | $R^1$-G4 | $R^2$-G3 | $R^3$-G2 | $R^4$-G2 | $R^5$-G2 |
| E22 | I | 0 or 1 | X-G5a | $R^1$-G4 | $R^2$-G3 | $R^3$-G3 | $R^4$-G3 | $R^5$-G3 |
| E23 | I | 0 | X-G5a | $R^1$-G4 | $R^2$-G3 | $R^3$-G2 | $R^4$-G2 | $R^5$-G2 |
| E24 | I | 0 | X-G5a | $R^1$-G4 | $R^2$-G3 | $R^3$-G3 | $R^4$-G3 | $R^5$-G3 |
| E25 | I | 0 | X-G5a | $R^1$-G4 | $R^2$-G4 | $R^3$-G2 | $R^4$-G2 | $R^5$-G2 |
| E26 | I | 0 | X-G5a | $R^1$-G4 | $R^2$-G4 | $R^3$-G3 | $R^4$-G3 | $R^5$-G3 |
| E27 | I | 0 | X-G5a | $R^1$-G4 | $R^2$-G5 | $R^3$-G2 | $R^4$-G2 | $R^5$-G2 |
| E28 | I | 0 | X-G5a | $R^1$-G4 | $R^2$-G5 | $R^3$-G3 | $R^4$-G3 | $R^5$-G3 |
| E29 | I | 0 | X-G5a | $R^1$-G4 | $R^2$-G6 | $R^3$-G2 | $R^4$-G2 | $R^5$-G2 |
| E30 | I | 0 | X-G5a | $R^1$-G4 | $R^2$-G6 | $R^3$-G3 | $R^4$-G3 | $R^5$-G3 |
| E31 | I | 0 or 1 | X-G5b | $R^1$-G2 | $R^2$-G2 | $R^3$-G2 | $R^4$-G2 | $R^5$-G2 |
| E32 | I | 0 or 1 | X-G5b | $R^1$-G3 | $R^2$-G2 | $R^3$-G2 | $R^4$-G2 | $R^5$-G2 |
| E33 | I | 0 or 1 | X-G5b | $R^1$-G3 | $R^2$-G2 | $R^3$-G3 | $R^4$-G3 | $R^5$-G3 |
| E34 | I | 0 or 1 | X-G5b | $R^1$-G4 | $R^2$-G3 | $R^3$-G2 | $R^4$-G2 | $R^5$-G2 |
| E35 | I | 0 or 1 | X-G5b | $R^1$-G4 | $R^2$-G3 | $R^3$-G3 | $R^4$-G3 | $R^5$-G3 |
| E36 | I | 0 | X-G5b | $R^1$-G4 | $R^2$-G3 | $R^3$-G2 | $R^4$-G2 | $R^5$-G2 |
| E37 | I | 0 | X-G5b | $R^1$-G4 | $R^2$-G3 | $R^3$-G3 | $R^4$-G3 | $R^5$-G3 |
| E38 | I | 0 | X-G5b | $R^1$-G4 | $R^2$-G4 | $R^3$-G2 | $R^4$-G2 | $R^5$-G2 |

-continued

| Embodiment | Formula | n | X | $R^1$ | $R^2$ | $R^3$ | $R^4$ | $R^5$ |
|---|---|---|---|---|---|---|---|---|
| E39 | I | 0 | X-G5b | $R^1$-G4 | $R^2$-G4 | $R^3$-G3 | $R^4$-G3 | $R^5$-G3 |
| E40 | I | 0 | X-G5b | $R^1$-G4 | $R^2$-G5 | $R^3$-G2 | $R^4$-G2 | $R^5$-G2 |
| E41 | I | 0 | X-G5b | $R^1$-G4 | $R^2$-G5 | $R^3$-G3 | $R^4$-G3 | $R^5$-G3 |
| E42 | I | 0 | X-G5b | $R^1$-G4 | $R^2$-G6 | $R^3$-G2 | $R^4$-G2 | $R^5$-G2 |
| E43 | I | 0 | X-G5b | $R^1$-G4 | $R^2$-G6 | $R^3$-G3 | $R^4$-G3 | $R^5$-G3 |
| E44 | I.2 | — | X-G3 | $R^1$-G2 | $R^2$-G2 | $R^3$-G2 | — | — |
| E45 | I.2 | — | X-G3 | $R^1$-G3 | $R^2$-G3 | $R^3$-G2 | — | — |
| E46 | I.2 | — | X-G3 | $R^1$-G3 | $R^2$-G3 | $R^3$-G3 | — | — |
| E47 | I.2 | — | X-G3 | $R^1$-G4 | $R^2$-G4 | $R^3$-G2 | — | — |
| E48 | I.2 | — | X-G3 | $R^1$-G4 | $R^2$-G4 | $R^3$-G3 | — | — |
| E49 | I.2 | — | X-G3 | $R^1$-G5 | $R^2$-G5 | $R^3$-G2 | — | — |
| E50 | I.2 | — | X-G3 | $R^1$-G5 | $R^2$-G5 | $R^3$-G3 | — | — |
| E51 | I.2 | — | X-G3 | $R^1$-G5 | $R^2$-G6 | $R^3$-G2 | — | — |
| E52 | I.2 | — | X-G3 | $R^1$-G5 | $R^2$-G6 | $R^3$-G3 | — | — |
| E53 | I.2 | — | X-G4 | $R^1$-G2 | $R^2$-G2 | $R^3$-G2 | — | — |
| E54 | I.2 | — | X-G4 | $R^1$-G3 | $R^2$-G3 | $R^3$-G2 | — | — |
| E55 | I.2 | — | X-G4 | $R^1$-G3 | $R^2$-G3 | $R^3$-G3 | — | — |
| E56 | I.2 | — | X-G4 | $R^1$-G4 | $R^2$-G4 | $R^3$-G2 | — | — |
| E57 | I.2 | — | X-G4 | $R^1$-G4 | $R^2$-G4 | $R^3$-G3 | — | — |
| E58 | I.2 | — | X-G4 | $R^1$-G5 | $R^2$-G5 | $R^3$-G2 | — | — |
| E59 | I.2 | — | X-G4 | $R^1$-G5 | $R^2$-G5 | $R^3$-G3 | — | — |
| E60 | I.2 | — | X-G4 | $R^1$-G5 | $R^2$-G6 | $R^3$-G2 | — | — |
| E61 | I.2 | — | X-G4 | $R^1$-G5 | $R^2$-G6 | $R^3$-G3 | — | — |
| E62 | I.2 | — | X-G5a | $R^1$-G2 | $R^2$-G2 | $R^3$-G2 | — | — |
| E63 | I.2 | — | X-G5a | $R^1$-G3 | $R^2$-G3 | $R^3$-G2 | — | — |
| E64 | I.2 | — | X-G5a | $R^1$-G3 | $R^2$-G3 | $R^3$-G3 | — | — |
| E65 | I.2 | — | X-G5a | $R^1$-G4 | $R^2$-G4 | $R^3$-G2 | — | — |
| E66 | I.2 | — | X-G5a | $R^1$-G4 | $R^2$-G4 | $R^3$-G3 | — | — |
| E67 | I.2 | — | X-G5a | $R^1$-G5 | $R^2$-G5 | $R^3$-G2 | — | — |
| E68 | I.2 | — | X-G5a | $R^1$-G5 | $R^2$-G5 | $R^3$-G3 | — | — |
| E69 | I.2 | — | X-G5a | $R^1$-G5 | $R^2$-G6 | $R^3$-G2 | — | — |
| E70 | I.2 | — | X-G5a | $R^1$-G5 | $R^2$-G6 | $R^3$-G3 | — | — |
| E71 | I.2 | — | X-G5b | $R^1$-G2 | $R^2$-G2 | $R^3$-G2 | — | — |
| E72 | I.2 | — | X-G5b | $R^1$-G3 | $R^2$-G3 | $R^3$-G2 | — | — |
| E73 | I.2 | — | X-G5b | $R^1$-G3 | $R^2$-G3 | $R^3$-G3 | — | — |
| E74 | I.2 | — | X-G5b | $R^1$-G4 | $R^2$-G4 | $R^3$-G2 | — | — |
| E75 | I.2 | — | X-G5b | $R^1$-G4 | $R^2$-G4 | $R^3$-G3 | — | — |
| E76 | I.2 | — | X-G5b | $R^1$-G5 | $R^2$-G5 | $R^3$-G2 | — | — |
| E77 | I.2 | — | X-G5b | $R^1$-G5 | $R^2$-G5 | $R^3$-G3 | — | — |
| E78 | I.2 | — | X-G5b | $R^1$-G5 | $R^2$-G6 | $R^3$-G2 | — | — |
| E79 | I.2 | — | X-G5b | $R^1$-G5 | $R^2$-G6 | $R^3$-G3 | — | — |
| E80 | I.2 | — | X-G6 | $R^1$-G2 | $R^2$-G2 | $R^3$-G2 | — | — |
| E81 | I.2 | — | X-G6 | $R^1$-G3 | $R^2$-G3 | $R^3$-G2 | — | — |
| E82 | I.2 | — | X-G6 | $R^1$-G3 | $R^2$-G3 | $R^3$-G3 | — | — |
| E83 | I.2 | — | X-G6 | $R^1$-G4 | $R^2$-G4 | $R^3$-G2 | — | — |
| E84 | I.2 | — | X-G6 | $R^1$-G4 | $R^2$-G4 | $R^3$-G3 | — | — |
| E85 | I.2 | — | X-G6 | $R^1$-G4 | $R^2$-G5 | $R^3$-G2 | — | — |
| E86 | I.2 | — | X-G6 | $R^1$-G4 | $R^2$-G5 | $R^3$-G3 | — | — |
| E87 | I.2 | — | X-G6 | $R^1$-G4 | $R^2$-G6 | $R^3$-G2 | — | — |
| E88 | I.2 | — | X-G6 | $R^1$-G4 | $R^2$-G6 | $R^3$-G3 | — | — |
| E89 | I.2 | — | X-G6 | $R^1$-G5 | $R^2$-G5 | $R^3$-G2 | — | — |
| E90 | I.2 | — | X-G6 | $R^1$-G5 | $R^2$-G5 | $R^3$-G3 | — | — |
| E91 | I.2 | — | X-G6 | $R^1$-G5 | $R^2$-G6 | $R^3$-G2 | — | — |
| E92 | I.2 | — | X-G6 | $R^1$-G5 | $R^2$-G6 | $R^3$-G3 | — | — |

A preferred embodiment of the present invention concerns compounds of formula (I.2)

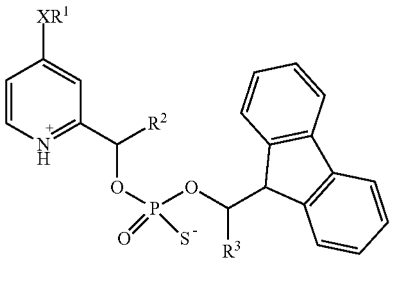

, wherein

X is O;

$R^1$ is selected from the group consisting of H and $C_{1-4}$alkyl;

$R^2$ is $CH_3$; and $R^3$ is H;

or an enantiomer, diastereomer or salt thereof.

A more preferred embodiment of the present invention concerns compounds of formula (I.2), wherein X is O;

$R^1$ is $C_{1-3}$alkyl; $R^2$ is $CH_3$; and $R^3$ is H;

or an enantiomer, diastereomer or salt thereof.

Preferred compounds of the invention include:

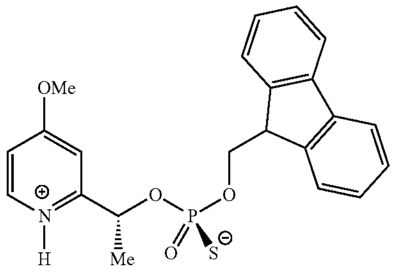

(R, $R_P$)

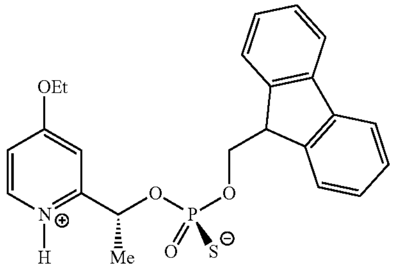

(R, $R_P$)

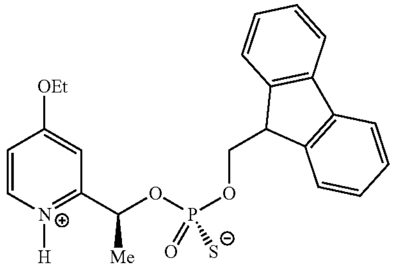

(S, $S_P$)

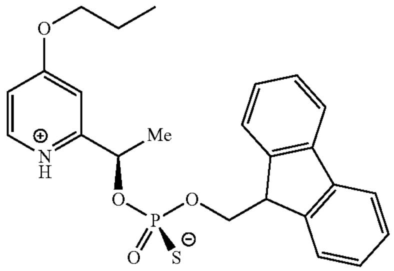

(R, $R_P$)

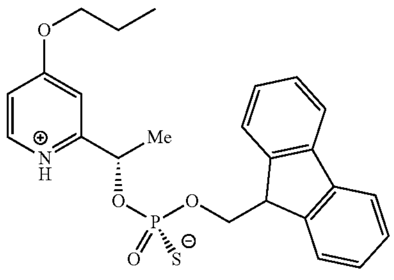

(S, $S_P$)

-continued

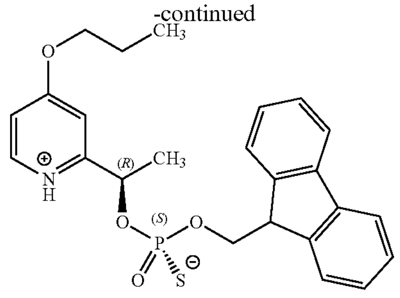

(R, $S_P$)

Particularly preferred compounds, including their stereoisomers, and the salts thereof, are described in the experimental section hereinafter.

The compounds according to the invention may be obtained using methods of synthesis, which are known to the one skilled in the art and described in the literature of organic synthesis. Preferably, the compounds are obtained analogously to the methods of preparation explained more fully hereinafter, in particular as described in the experimental section.

Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of the formula (I) according to the present invention including their tautomers, stereoisomers and mixtures thereof and the salts thereof, and the solvates and hydrates of such compounds, including the solvates and hydrates of such tautomers, stereoisomers and salts thereof.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

The numeration of the atoms of a substituent starts with the atom which is closest to the core or to the group to which the substituent is attached.

For example, the term "3-carboxypropyl-group" represents the following substituent:

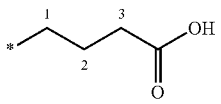

wherein the carboxy group is attached to the third carbon atom of the propyl group. The terms "1-methylpropyl-", "2,2-dimethylpropyl-" or "cyclopropylmethyl-" group represent the following groups:

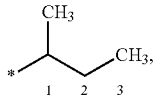
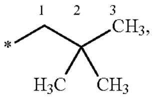
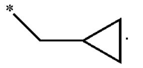

The asterisk may be used in sub-formulas to indicate the bond which is connected to the core molecule as defined.

In a definition of a group the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$." or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, and solvates thereof such as for instance hydrates including solvates of the free compounds or solvates of a salt of the compound.

As used herein, "salts" refer to derivatives of the disclosed compounds wherein the parent compound is modified by making acid or base salts thereof. Examples of salts include, but are not limited to, mineral or organic acid salts of basic residues such as amines; alkali or organic salts of acidic residues such as carboxylic acids; and the like.

The salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention also comprise a part of the invention.

The term halogen generally denotes fluorine, chlorine, bromine and iodine.

The term "$C_{1-n}$-alkyl", wherein n is an integer from 1 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_3$-n-cycloalkyl", wherein n is an integer 4 to n, either alone or in combination with another radical denotes a cyclic, saturated, unbranched hydrocarbon radical with 3 to n C atoms. The cyclic group may be mono-, bi-, tri- or spirocyclic, most preferably monocyclic. Examples of such cycloalkyl groups include cyclopropyl, cyclobutyl, cyclo-pentyl, cyclohexyl, cycloheptyl, cyclooctyl, cyclononyl, cyclododecyl, bicyclo[3.2.1.]octyl, spiro[4.5]decyl, norpinyl, norbonyl, norcaryl, adamantyl, etc.

The term "aryl" as used herein, either alone or in combination with another radical, denotes a carbocyclic aromatic monocyclic group containing 6 carbon atoms which is optionally further fused to a second five- or six-membered, carbocyclic group which is optionally aromatic, saturated or unsaturated. Aryl includes, but is not limited to, phenyl, indanyl, indenyl, naphthyl, anthracenyl, phenanthrenyl, tetrahydronaphthyl and dihydronaphthyl. Preferably, aryl denotes phenyl or naphthyl. More preferably, aryl denotes phenyl.

Many of the terms given above may be used repeatedly in the definition of a formula or group and in each case have one of the meanings given above, independently of one another.

All rests and substituents as defined hereinbefore and hereinafter may be substituted with one or more F atoms.

Use of the Compounds of the Invention in the Synthesis of Chiral Phosphothioates General synthesis of chiral phosphorothioates with the compounds of the invention Scheme 1

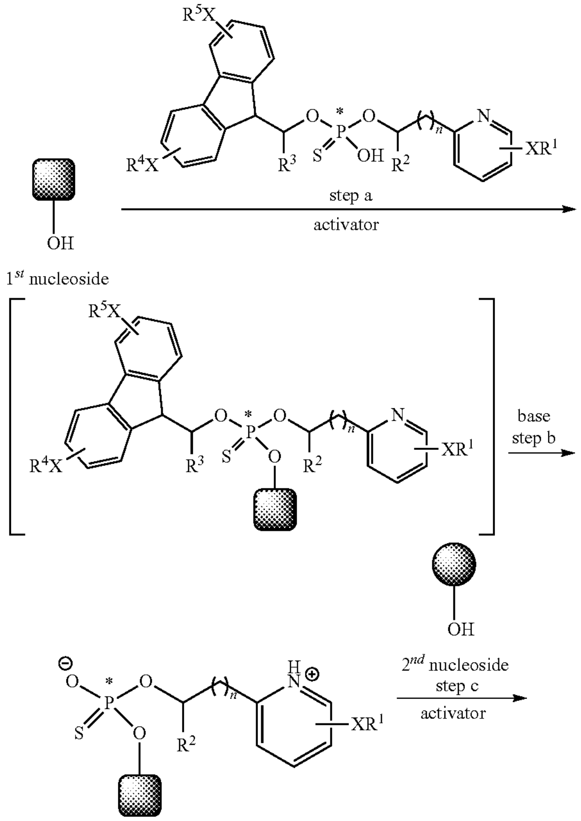

-continued

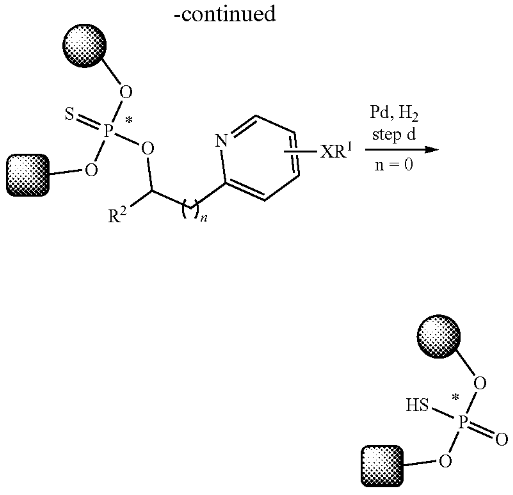

chiral
phosphorothioate

The 1st nucleoside (including ribonucleosides and deoxyribonuleosides) is first coupled with the chiral synthon in the presence of activator such as DMOCP in the solvent such as pyridine and acetonitrile. Without isolation, the coupling product is treated with base such DBU, TMG, t-$BuNH_2$ or trialkyl amines such as $Et_3N$ or $^iPr_2NEt$ to remove the fluorenylmethyl group. The isolated product is coupled with 2nd nucleoside (including ribonucleosides and deoxyribonuleosides) under the similar conditions for the first coupling. Hydrogenation conditions to remove the 1-(2-pyridinyl) ethyl group gives the chiral phosphorothioate. If DMTr is used for the protection of nucleoside, the Pd-catalyzed hydrogenation works with or without DMTr. Various Pd catalyst such as Pd/C, $Pd(OAc)_2$ and $Pd(CF_3CO_2)_2$ can be used in the presence of Lewis acid such as $Zn(OTf)_2$, $Zn(CF_3CO_2)_2$, $ZnBr_2$ and $ZnCl_2$.

Structure of possible activators:

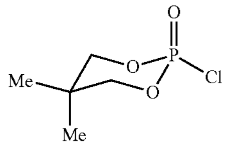

DMOCP

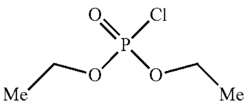

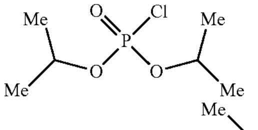

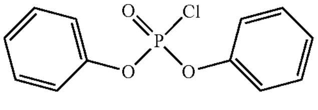

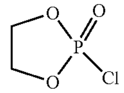

COP

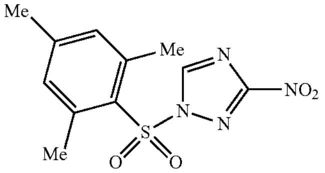

MSNT

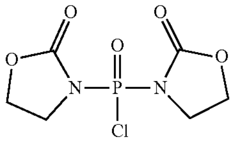

OXP

An example for the application of $FPPS^{Pr}$ is shown in scheme 2 below:

Scheme 2

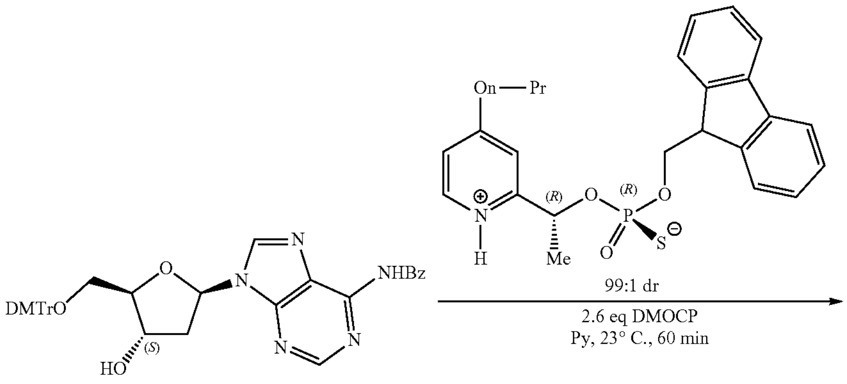

A

-continued

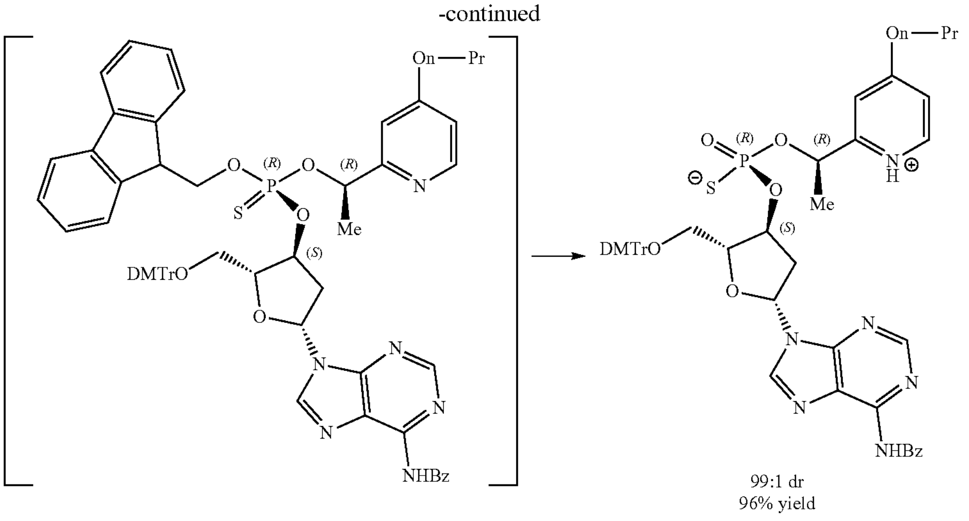

N-6-Benzoyl-5'-O-(4,4'-dimethoxytrityl)-2'-deoxyadenosine was coupled with O-((9H-fluoren-9-yl)methyl) O—((R)-1-(4-propoxypyridin-1-ium-2-yl)ethyl) (R)-phosphorothioate with 2-chloro-5,5-dimethyl-1,3,2-dioxaphosphorinane-2-oxide (DMOCP) as the activator in pyridine at room temperature. After the reaction went to completion, water was added to quench the reaction. DBU was then introduced to remove fluorenylmethyl group. The product was extracted with organic solvent such as EtOAc. Typically, the chiral phosphorothioate product was isolated with quantitative yield. An analytically pure sample was easily obtained by silica gel column chromatography purification. Typically, P-chirality of the synthon O-((9H-fluoren-9-yl) methyl) O-((R)-1-(4-propoxypyridin-1-ium-2-yl)ethyl) (R)-phosphorothioate was completely transferred to the product and the whole chemical process is stereoselective. In other words, the product will be isolated with 99:1 dr if the synthon with 99:1 dr is used in the coupling.

Synthesis Schemes

Typical methods of preparing the compounds of the invention are described in the experimental section.

The compounds of the present invention can also be made by methods known in the art including those described below and including variations within the skill of the art.

Scheme 1 shows the synthesis of the synthons. All the synthons are prepared by the coupling of the chiral alcohol and the H-phosphonate bearing fluorenylmethyl group in the presence of activator such as DMOCP or PivCl in a suitable solvent such as pyridine at room temperature. Sulfurization of the product is achieved by addition of sulfur or $S_8$. In some cases, the diastereomerically pure isomer was isolated by simple filtration after addition of antisolvents such as MeOH, $CH_3CN$ and water. By using the enantiomer of the chiral alcohol, the enantiomer of the synthon is prepared in the same manner.

Scheme 3

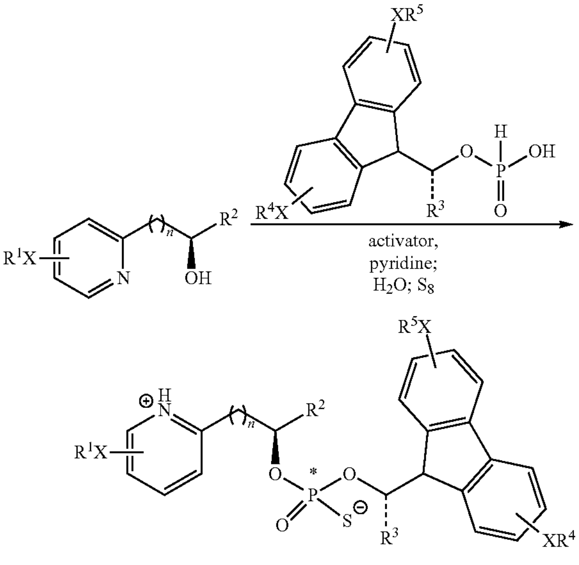

orthogonally protected
chiral phosphorothioate synthon

The chiral alcohol used as starting material in scheme 3 can be prepared as follows:

Scheme 4

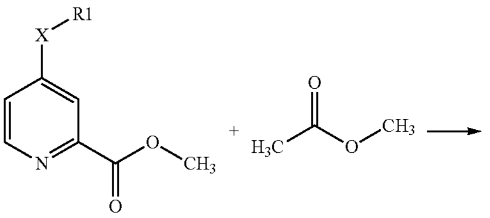

-continued

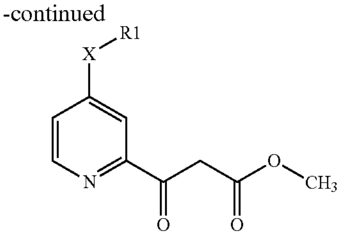

If n is 0 and $R^2$ is methyl, Claisen condensation of 4-substituted methyl picolinate and acetate such as MeOAc and EtOAc in the presence of base such as t-BuOK and LDA give the corresponding β-ketone ester.

Scheme 5

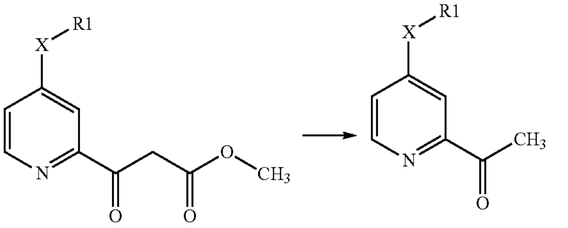

If n is 0 and $R^2$ is methyl, the ketone ester undergoes sequential hydrolysis and decarboxylation under acidic conditions to afford the methyl ketone.

Further ketones needed for the synthesis of the chiral alcohols mentioned below may be obtained using methods of synthesis which are known to the one skilled in the art and described in the literature of organic synthesis.

Depending on n, the corresponding ketone is then transformed into the chiral alcohol:

Scheme 6a for n = 0

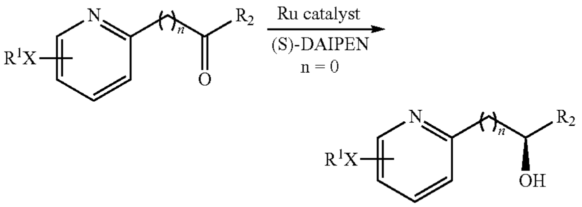

If n is 0, the ketone can be converted to the corresponding (R)-chiral alcohol with the S-isomer of the catalyst under Noyori' hydrogenation conditions.

Scheme 6b for n = 1

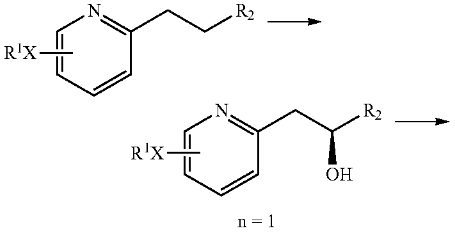

-continued

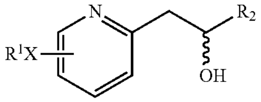

Ronald L. Reyes, Tomohiro Iwai, Satoshi Maeda and Masaya Sawamura, *J. Am. Chem. Soc.* 2019, 141, 6817-6821

Andreas Weickgenannt, Marius Mewald, Thomas W. T. Muesmann, Martin Oestreich Prof. Dr., *Angewandte Chemie, International Edition* 2010, 49, 2223-2226

Scheme 6c for n = 2

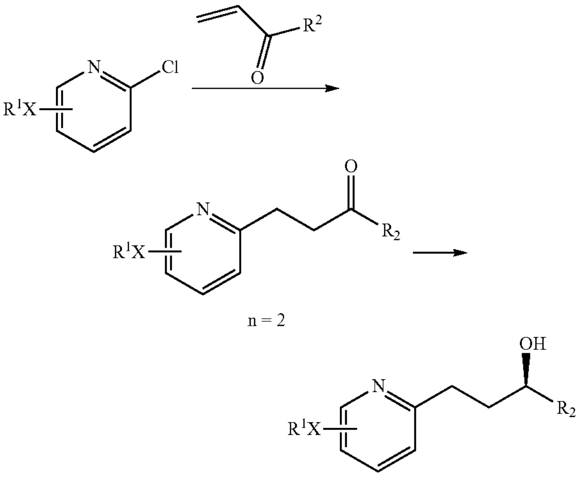

Sylvie Condon, Daniel Dupré, Isabelle Lachaise, Jean-Yves Nédélec, *Synthesis* 2002, 12, 1752-1758

Scheme 6d for n = 3

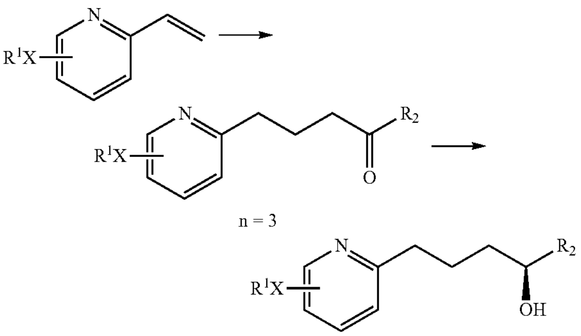

Boekelheide, V.; Mason, J. H., *Journal of the American Chemical Society* 1951, 73, 2356-7

Scheme 6e for n = 2-6

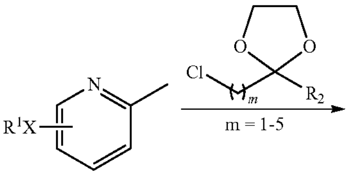

-continued

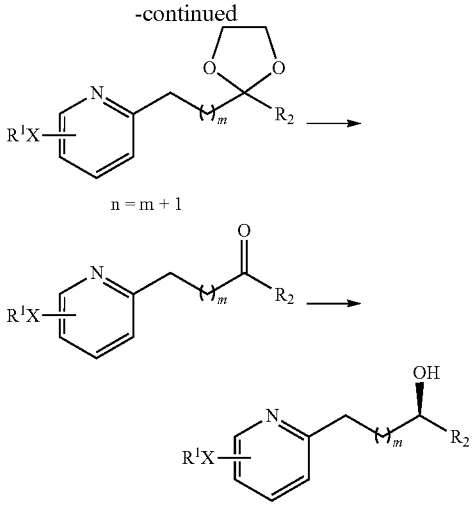

Nils Aake Bergman, Torbjoern Halvarsson, *J. Org. Chem.* 1989, 54, 2137-2142.

As depicted in scheme 3 above, condensation of the chiral alcohol and [(9H-fluoren-9-yl)methoxy]phosphinic acid followed by sulfurization with $S_8$ gives a 1:1 diastereomer. After addition of $CH_3CN$ or MeOH and water, the (R, Rp)-diastereomer is isolated with high/excellent diastereoselectivity. Further slurry in a solvent such toluene removed the residual $S_8$. Typical yield of the solid product is 35-40%.

EXPERIMENTAL PART

The Examples that follow are intended to illustrate the present invention without restricting it. The terms "ambient temperature" and "room temperature" are used interchangeably and designate a temperature of about 20° C.

The hereinafter described compounds have been characterized through their characteristic mass after ionisation in a mass-spectrometer and their retention time on an analytical HPLC.

List of Abbreviations

| | |
|---|---|
| 2'-OH | 2'-hydroxyl |
| 5'-OH | 5'-hydroxyl |
| Ac | acetyl |
| Aq. | aqueous |
| BINAP | (2,2'-bis(diphenylphosphino)-1,1'-binaphthyl) |
| Bz | benzoyl |
| COP | 2-chloro-2-oxo-1,3,2-dioxaphosphorinane |
| dA | deoxyadenosine |
| DAIPEN | 1,1-bis(4-methoxyphenyl)-3-methyl-1,2-butanediamine |
| DBU | 1,8-diazabicyclo[5.4.0]undec-7-ene |
| dC | deoxycytidine |
| DCA | dichloroacetic acid |
| DCM | dichloromethane |
| dG | deoxyguanosine |
| DMAc | dimethylacetamide |
| DMOCP | 2-chloro-5,5-dimethyl-1,3,2-dioxaphosphorinane-2-oxide |
| DMTr | bis(4-O-methoxyphenyl)phenylmethyl-(4,4'-dimethoxytrityl) |
| DNA | deoxyribonucleic acid |
| dr | diastereomeric ratio |
| dT | thymidine |
| er | enantiomeric ratio |
| EtOAc | ethyl acetate |
| Fm | (9H-fluoren-9-yl)methyl |
| FPPS | Fluorenemethyl 1-(Pyridin-2-yl)ethyl Phosphorothioate |

-continued

| | |
|---|---|
| h | hour(s) |
| HPLC | high performance liquid chromatography |
| KDMO | potassium 3,7-dimethyl-3-octanoxide |
| MNST | (mesitylenesulfonyl)-3-nitro-1,2,4-triazole |
| MTBE | methyl tert-butyl ether |
| NMR | nulcear magnetic resonance |
| OXP | bis(2-oxo-3-oxazolidinyl) phosphinic chloride |
| RNA | ribonucleic acid |
| RP-HPLC | reverse phase high performance liquid chromatography |
| TBAF | tetrabutylammonium fluoride |
| TBDMS | tert-butyldimethylsilyl |
| TBDPS | tert-butyldiphenylsilyl |
| THF | tetrahydrofuran |
| TMG | 1,1,3,3-tetramethylguanidine |
| Piv | trimethylacetyl |
| PivCl | pivaloyl chloride |
| Pr | propyl |
| Py | pyridine |
| xyl | 3,5-dimethylphenyl |

General Experimental

All reagents were purchased and used without further purification unless otherwise stated. Reactions were monitored by RP-HPLC analysis, see respective sections for details. NMR spectra were recorded on Bruker DRX-600, DRX-500, and AMX-400 instruments and were calibrated using residual undeuterated solvent (e.g., $CHCl_3$ at 7.26 ppm 1H NMR, 77.16 13C NMR). The following abbreviations were used to explain multiplicities: s=singlet, d=doublet, t=triplet, q=quartet, m=multiplet, br=broad. Column chromatography was performed using E. Merck silica gel (60, particle size 0.043-0.063 mm). High-resolution mass spectra (HRMS) were recorded on an Agilent LC/MSD TOF mass spectrometer by electrospray ionization time of flight reflectron experiments.

Synthesis of the Synthons

Example 1

Synthesis of [(9H-fluoren-9-yl)methoxy]phosphinic acid

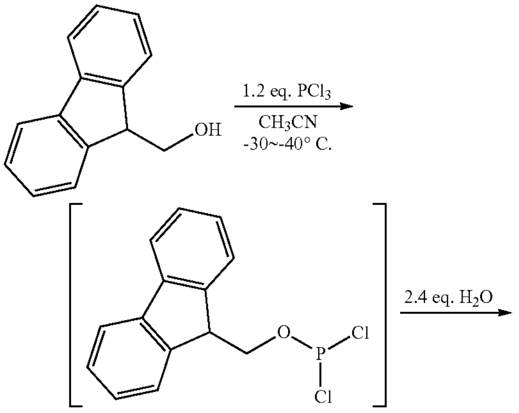

-continued

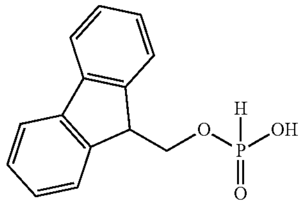

To a clean and dry reactor was added acetonitrile (11.5 L). After the solvent was cooled to −35° C., $PCl_3$ (3.78 kg, 27.5 mol, 1.20 eq.) was added in one portion. Then a solution of (9H-fluoren-9-yl)methanol (4.5 kg, 22.9 mol) in acetonitrile (36 L) was added at a temperature between −30° C. and −40° C. After 30 min between −30° C. and −40° C., the mixture was warmed to 0° C. over 0.5 h. Water (0.99 kg, 55 mol, 2.4 eq.) was added while controlling the temperature below 20° C. The mixture was then warmed to 20° C. After 2 h at 20-25° C., the solid was collected by filtration and then washed with acetonitrile (8 L). After drying at 40° C. under vacuum, a total of 4.47 kg (75% yield) of the product was obtained as a solid.

$^1$H NMR (400 MHz, $CDCl_3$): δ 7.74 (d, J=7.6 Hz, 2H), 7.58 (dd, J=0.84, 7.52 Hz, 2H), 7.38 (t, J=7.48 Hz, 2H), 7.28 (dt, J=1.12, 7.48 Hz, 2H), 6.75 (d, J (P, H)=710.3 Hz, 1H), 4.30 (t, J=7.24 Hz, 2H), 4.21 (t, J=7.12, 1H). $^{13}$C NMR (100 MHz, $CDCl_3$): δ 143.0, 141.3, 128.0, 127.2, 125.2, 120.1, 67.2 [d, J (P, C)=5.94 Hz], 47.9 [d, J (P, C)=7.09 Hz]. $^{31}$P NMR (162 MHz, $CDCl_3$): δ 8.7.

Example 2

Synthesis of O-((9H-fluoren-9-yl)methyl)O—((R)-1-(4-methoxypyridin-1-ium-2-yl)ethyl) (R)-phosphorothioate (FPPS$^{Me}$)

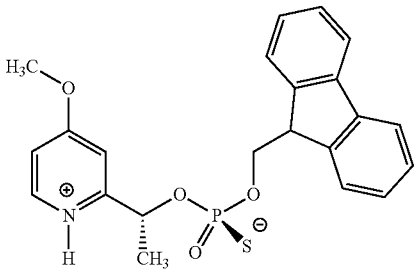 [SMILES: COc1cc[nH+]c([C@@H](C)O[P@](=O)(S)OCC2c3ccccc3-c3ccccc32)c1]

a) Methyl 3-(4-methoxypyridin-2-yl)-3-oxopropanoate

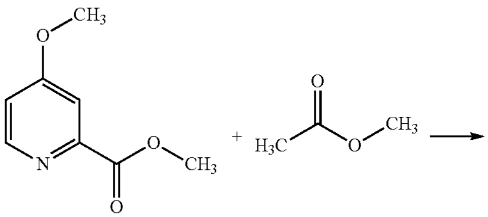

-continued

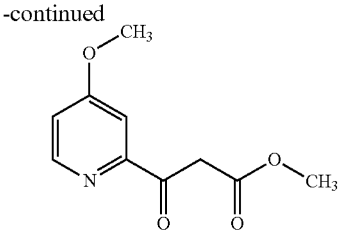

To a dry and clean flask was charged KOt-Bu (84.8 g, 897.3 mmol, 3.0 eq.) and THF (400 mL). The mixture was stirred at 23° C. to obtain a clear solution. After the solution was cooled to 0° C., 4-methoxy-pyridine-2-carboxylic acid methyl ester (50 g, 299.1 mmol, 1.0 eq.) in THF (100 mL) was added followed by addition of methyl acetate (51 g, 688.0 mmol, 2.2 eq.) maintaining the temperature below 5° C. After 1 h at 0° C., the reaction was quenched and acidified with 12 M HCl to pH 5. The organic solvent was removed under vacuum. The product was extracted with EtOAc. The organic layer was washed with water. Removal of the solvent gave the crude ketone ester product, which was used for next step directly.

b) 1-(4-Methoxypyridin-2-yl)ethan-1-one

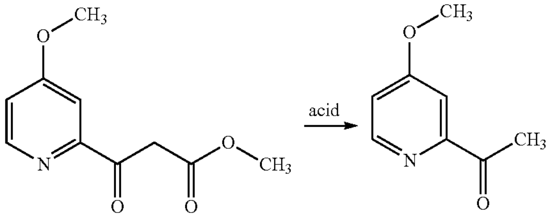

To a flask was charged methyl 3-(4-methoxypyridin-2-yl)-3-oxopropanoate (62 g, 296.4 mmol), HOAc (248 mL) and water (49.6 mL) followed by addition of $H_2SO_4$ (45.6 mL). Then the mixture was heated at 98° C. for 2 h. After the residue was cooled to 0° C., 6M NaOH was added to reach pH=5.5. The product was extracted with EtOAc. The organic layer was washed with water. The organic solution was then treated with activated carbon. After concentration, the product solidified and was slurried in hexane. The solid was collected and then washed with hexane. After drying, 42 g of the product was isolated with 94% yield.

$^1$H-NMR (500 MHz, DMSO-$d_6$) δ 8.53 (d, J=5.60 Hz, 1H), 7.44 (d, J=1.80 Hz, 1H), 7.22 (dd, J=1.70, 5.25 Hz, 1H), 3.90 (s, 3H), 2.62 (s, 3H).

c) (1R)-1-(4-Methoxypyridin-2-yl)ethan-1-ol

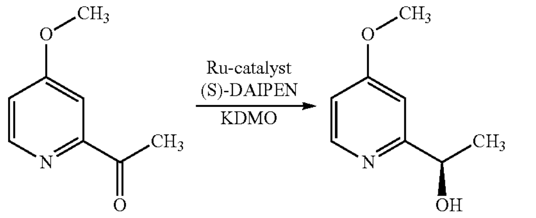

To a reactor was added the 1-(4-methoxypyridin-2-yl) ethan-1-one (10 g, 66.2 mmol), $RuCl_2$[(S)-xylBINAP][(S)-DAIPEN] (40.4 mg, 0.033 mmol), KDMO (0.779 g, 50% in heptane, 0.03 eq), 2-PrOH (50 mL). The mixture was stirred at 450 psi $H_2$ at 20-21° C. for 14 h. The product was purified by column chromatography with 0-60% EtOAc in hexane. A total of 8.2 g of the product was isolated with 81% yield and 87:13 er.

$^1$H-NMR (400 MHz, DMSO-$d_6$) δ 8.28 (d, J=5.68 Hz, 1H), 7.05 (d, J=2.52 Hz, 1H), 6.81 (dd, J=2.60, 5.68 Hz, 1H), 5.34 (d, J=4.72 Hz, 1H), 4.68 (m, 1H), 3.83 (s, 3H), 1.35 (d, J=6.56 Hz, 3H).

d) O-((9H-fluoren-9-yl)methyl)O—((R)-1-(4-methoxypyridin-1-ium-2-yl)ethyl) (R)-phosphorothioate ($FPPS^{Me}$)

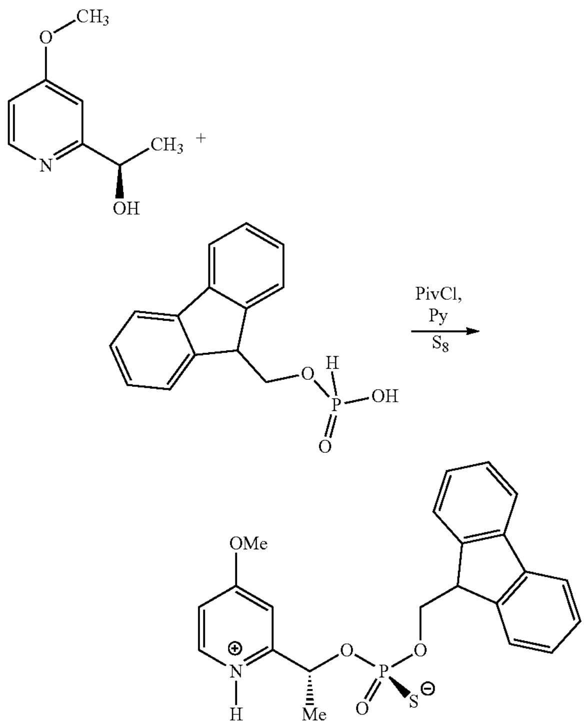

To a flask was charged (1R)-1-(4-methoxypyridin-2-yl)ethan-1-ol (5.0 g, 32.6 mmol) and (9H-fluoren-9-yl)methoxy]phosphinic acid (10.0 g, 35.9 mmol) followed by addition of pyridine (15.000 ml). 2,2-Dimethylpropanoyl chloride (PivCl) (5.566 g, 5.685 ml, 45.7 mmol) was added while maintaining the temperature between 2° and 25° C. After 0.5 h at 20-25° C., water (1.18 g, 65.283 mmol) was added followed by addition of sulfur (1.1 g, 34.274 mmol) maintaining the temperature below 35° C. After 2-3 h, the mixture was diluted with EtOAc and washed successively with 2M $KHSO_4$ and water. The organic layer was concentrated. To the residue was added 25 mL of MeOH. After overnight, the solid was collected and then washed with 10 mL of MeOH. The solid was further slurried in toluene to remove residual sulfur. The isolated solid was dried under vacuum to give 3.3 g of the product $FPPS^{Me}$ with 23.7% yield.

$^1$H NMR (600 MHz, pyridine-$d_5$): 8.48 (d, J=5.64 Hz, 1H), 7.86 (d, J=7.50 Hz, 1H), 7.80 (d, J=7.56 Hz, 2H), 7.77 (d, J=7.50 Hz, 1H), 7.57 (d, J=2.10 Hz, 1H), 7.35 (q, J=7.08, 13.38 Hz, 2H), 7.25-7.21 (m, 2H), 6.72 (dd, J=2.40, 5.58 Hz, 1H), 6.29 (m, 1H), 4.77 (m, 1H), 4.63 (m, 1H), 4.48 (t, J=7.26 Hz, 1H), 3.57 (s, 3H), 1.93 (d, J=6.54 Hz, 3H). $^{13}$C NMR (150 MHz, pyridine-$d_5$): 166.7, 165.5 [d, J (P, C)=6.21 Hz], 150.4, 145.1, 144.9, 141.7, 141.7, 128.0, 127.9, 127.4, 126.1, 125.9, 120.3, 120.3, 109.0, 106.7, 76.0 [d, J (P, C)=5.18 Hz], 68.8 [d, J (P, C)=5.48 Hz], 55.0, 48.9 [d, J (P, C)=8.13 Hz], 23.5 [d, J (P, C)=4.17 Hz]. HRMS (ES pos.): m/z calcd for $C_{22}H_{23}NO_4PS$ (M+H$^+$): 428.10799, found: 428.10777.

Example 3

Synthesis of O-((9H-fluoren-9-yl)methyl)O—((R)-1-(4-ethoxypyridin-1-ium-2-yl)ethyl) (R)-phosphorothioate ($FPPS^{Et}$)

a) Ethyl 3-(4-ethoxypyridin-2-yl)-3-oxopropanoate

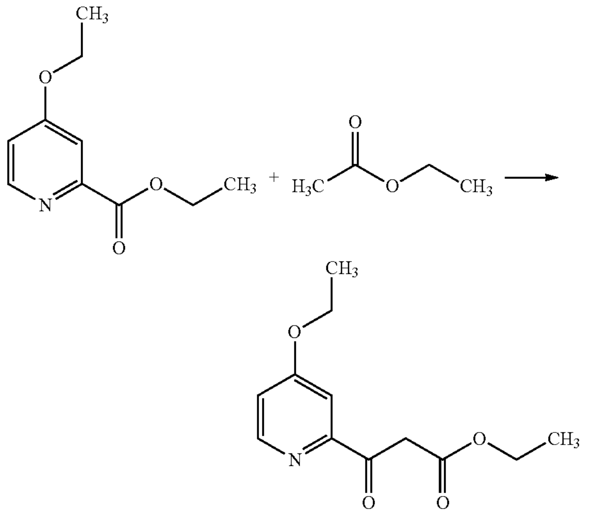

To a dry and clean flask was charged KOt-Bu (64.5 g, 563.5 mmol, 2.2 eq.) and THF (500 mL). The mixture was stirred at 23° C. to obtain a clear solution. After the solution was cooled to −20° C., ethyl acetate (55 ml, 563.5 mmol, 2.2 eq.) was added maintaining the temperature below −15° C. After 15 min, 4-ethoxy-pyridine-2-carboxylic acid ethyl ester (50 g, 256.13 mmol, 1.0 eq.) in THF (100 mL) was added over 0.5 h while maintaining the temperature below 0° C. After 0.5 h at 0° C., the reaction was quenched with acetic acid (43.99 ml, 768.4 mmol) followed by addition of water (400 mL). The solvent was removed under vacuum. The product was extracted with EtOAc. The organic layer was washed with water. Removal of the solvent gave the crude ketone ester product. An analytic sample was obtained by chromatography on silica gel column.

$^1$H NMR (400 MHz, $CDCl_3$): δ 8.45 (d, J=5.64 Hz, 1H), 7.56 (d, J=2.40 Hz, 1H), 6.96 (dd, J=2.56, 5.64 Hz, 1H), 4.22-4.12 (m, 6H), 1.45 (t, J=7.0 Hz, 3H), 1.24 (t, J=7.16 Hz, 3H). $^{13}$C NMR (100 MHz, $CDCl_3$): δ 200.0, 165.8, 155.4, 150.1, 114.2, 107.2, 63.9, 25.9, 14.4.

b) 1-(4-Ethoxypyridin-2-yl)ethan-1-one

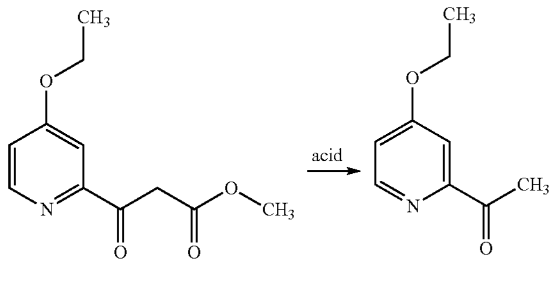 [SMILES: CCOc1ccnc(C(=O)CC(=O)OC)c1 ; CCOc1ccnc(C(C)=O)c1]

To a flask was charged ethyl 3-(4-ethoxypyridin-2-yl)-3-oxopropanoate (85.0 g; 358.3 mmol; 1.0 eq.) and HOAc (212.5 mL) and water (85 mL) followed by addition of $H_2SO_4$ (21.25 mL). Then the mixture was heated at 98° C. for 2 h. Most of the solvent was removed under vacuum. After the residue was cooled to 0° C., 6M NaOH was added to reach pH=11. The product was extracted with EtOAc. The organic layer was washed with water. The organic solution was then treated with activated carbon. After concentration, the product was used for the next step. The overall yield is 93%. An analytic sample was obtained by purification on silica gel column.

$^1$H NMR (400 MHz, $CDCl_3$): δ 8.47 (dd, J=0.52, 5.64 Hz, 1H), 7.54 (dd, J=0.68, 2.52 Hz, 1H), 6.95 (ddd, J=1.0, 2.64, 5.64 Hz, 1H), 4.14 (q, J=6.96, 14.0 Hz, 2H), 2.71 (s, 3H), 1.45 (t, J=7.0 Hz, 3H). $^{13}$C NMR (100 MHz, $CDCl_3$): δ 200.0, 165.8, 155.4, 150.1, 114.2, 107.2, 63.9, 25.9, 14.4.

c) (R)-1-(4-Ethoxypyridin-2-yl)ethan-1-ol

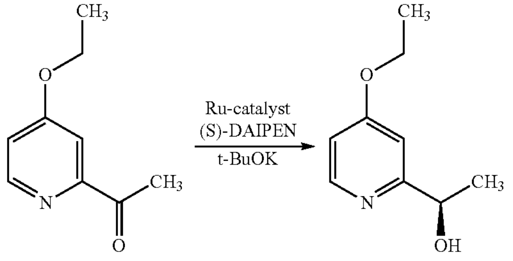

To a reactor was added 1-(4-ethoxypyridin-2-yl)ethan-1-one (10 g, 60.5 mmol), $RuCl_2$[(S)-xylBINAP][(S)-DAIPEN] (147.9 mg, 0.12 mmol), t-BuOK (271.7 mg, 2.42 mmol), 2-PrOH (40 mL). The mixture was stirred at 31.03 bar (450 psi) $H_2$ at 20-21° C. for 14 h. The product was purified by column chromatography with 0-60% EtOAc in hexane. The product was isolated with 90% yield and 97:3 er.

$^1$H NMR (400 MHz, $CDCl_3$): δ 8.17 (bs, 1H), 6.80 (d, J=2.44 Hz, 1H), 6.57 (m, 1H), 4.76 (q, J=6.52, 13.04 Hz, 1H), 3.98 (q, J=7.08, 14.12 Hz, 2H), 1.39 (d, J=6.44 Hz, 3H), 1.32 (t, J=7.0 Hz, 3H). $^{13}$C NMR (100 MHz, $CDCl_3$): δ 165.9, 165.7, 149.2, 109.0, 105.6, 69.3, 63.5, 24.1, 14.4.

Chiral HPLC conditions: Chiralpak AD-3, 4.6×250 mm; 96:4 heptane/ethanol, 1.3 mL/min, 220 nm, (R)-isomer, t=15.72 min, (S)-isomer, t=16.61 min.

d1) O-((9H-fluoren-9-yl)methyl)O—((R)-1-(4-ethoxypyridin-1-ium-2-yl)ethyl) (R)-phosphorothioate((R, $R_p$)—FPP-$S^{Et}$)

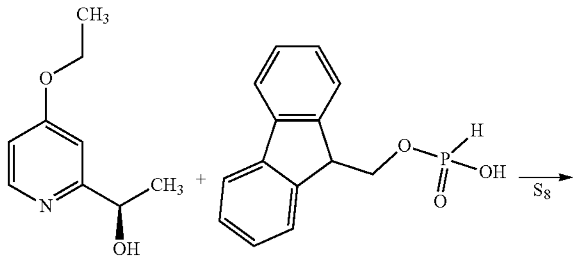

-continued

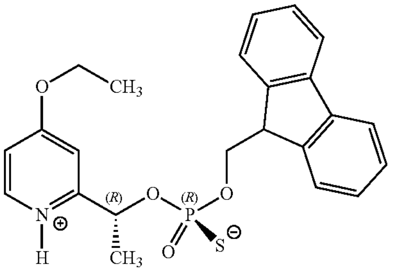

A mixture of (1R)-1-(4-ethoxypyridin-2-yl)ethan-1-ol (56 g; 334.92 mmol; 1.0 eq.) and [(9H-fluoren-9-yl)methoxy]phosphinic acid (131.3 g; 334.92 mmol; 1.0 eq.) was dried by coevaporation with pyridine (2×10 mL). After pyridine (196 mL) was added, 2,2-dimethylpropanoyl chloride (61.87 mL; 502.38 mmol; 1.5 eq.) was added. After 30 min, water (12.09 mL; 669.84 mmol; 2.0 eq.) was added followed by addition of sulfur (11.81 g; 368.41 mmol; 1.1 eq.). After 2 h, methanol (840 mL) was added. After 1 h at 23° C., the solid was collected and washed with methanol (504 mL). After the solid was suspended in toluene (560 mL), the solid was collected and washed with toluene (112 mL) and then dried under vacuum. The product was isolated with 31% yield with >98:2 dr.

$^1$H NMR (400 MHz, DMSO-$d_6$): δ 8.51 (d, J=6.72 Hz, 1H), 7.84-7.80 (m, 2H), 7.58-7.53 (m, 2H), 7.40-7.34 (m, 3H), 7.32-7.24 (m, 3H), 5.52 (m, 1H), 4.33-4.18 (m, 2H), 4.11 (m, 1H), 4.07-3.96 (m, 2H), 1.44 (d, J=6.52, 3H), 1.35 (t, J=6.92 Hz, 3H). $^{13}$C NMR (100 MHz, Py-$d_5$): δ 167.4, 166.6 [d, J (P, C)=6.02 Hz], 146.3 [d, J (P, C)=15.2 Hz], 142.9 [d, J (P, C)=3.0 Hz], 129.2 [d, J (P, C)=1.9 Hz], 128.7, 127.3, 127.2, 121.6 [d, J (P, C)=2.4 Hz], 110.7, 108.3, 77.2 [d, J (P, C)=5.0 Hz], 70.1 [d, J (P, C)=5.6 Hz], 65.0, 50.2 [d, J (P, C)=8.3 Hz], 24.8 [d, J (P, C)=4.8 Hz], 15.7. $^{31}$P NMR (162 MHz, Pyridine-$d_5$): δ 62.2. HRMS (ES pos.): m/z calcd for $C_{23}H_{25}NO_4PS$ (M+H$^+$): 442.12364, found: 442.12357.

d2) O-((9H-fluoren-9-yl)methyl)O—((S)-1-(4-ethoxypyridin-1-ium-2-yl)ethyl) (S)-phosphorothioate ((S, $S_p$)-FPP-$S^{Et}$)

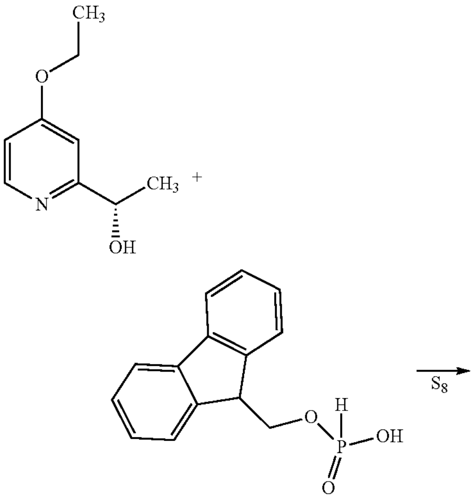

-continued

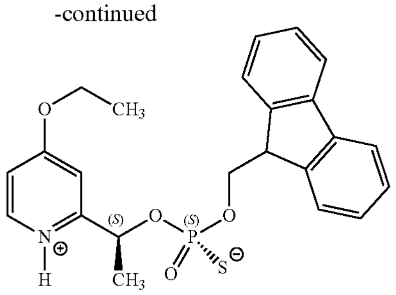

A mixture of (1S)-1-(4-ethoxypyridin-2-yl)ethan-1-ol (38.7 g; 231.5 mmol; 1.0 eq.) and [(9H-fluoren-9-yl) methoxy]phosphinic acid (60.2 g; 231.5 mmol; 1.0 eq.) was dried by coevaporation with pyridine (2×100 mL). After pyridine (194 mL) was added, 2,2-dimethylpropanoyl chloride (65.05 g; 347.2 mmol; 1.5 eq.) was added. After 30 min, water (8.36 mL; 462.9 mmol; 2.0 eq.) was added followed by addition of sulfur (22.27 g; 694.4 mmol; 3.0 eq.). After 2 h, methanol (774 mL) was added. After 1 h at 23° C., the solid was collected and washed with methanol (80 mL). After the solid was suspended in toluene (450 mL), the solid was collected and washed with toluene (80 mL) and then dried under vacuum. 34 g of the product was isolated with 33% yield with >98:2 dr.

$^1$H NMR (400 MHz, Py-$d_5$): δ 13.54 (bs, 2H), 10.00 (d, J=1.42 Hz, 1H), 9.37 (d, J=7.44 Hz, 1H), 9.32-9.27 (m, 3H), 9.05 (d, J=2.52 Hz, 1H), 8.89-8.84 (m, 2H), 8.77-8.72 (m, 2H), 8.27 (dd, J=2.52, 5.68 Hz, 1H), 7.79 (m, 1H), 6.27 (m, 1H), 6.16 (m, 1H), 5.99 (t, J=7.16 Hz, 1H), 5.31 (q, J=7.00, 14.00 Hz, 2H), 3.45 (d, J=6.60 Hz, 3H), 2.67 (t, J=6.96 Hz, 3H). $^{13}$C NMR (100 MHz, Py-$d_5$): δ 167.4, 166.6 [d, J (P, C)=6.02 Hz], 146.3 [d, J (P, C)=15.2 Hz], 142.9 [d, J (P, C)=3.0 Hz], 129.2 [d, J (P, C)=1.9 Hz], 128.7, 127.3, 127.2, 121.6 [d, J (P, C)=2.4 Hz], 110.7, 108.3, 77.2 [d, J (P, C)=5.0 Hz], 70.1 [d, J (P, C)=5.6 Hz], 65.0, 50.2 [d, J (P, C)=8.3 Hz], 24.8 [d, J (P, C)=4.8 Hz], 15.7. $^{31}$P NMR (162 MHz, pyridine-$d_5$): δ 62.2. HRMS (ES pos.): m/z calcd for $C_{23}H_{25}NO_4PS$ (M+H$^+$): 442.12364, found: 442.12361.

Example 4

Synthesis of O-((9H-fluoren-9-yl)methyl)O—((R)-1-(4-propoxypyridin-1-ium-2-yl)ethyl) (R)-phosphorothioate ((R, $R_p$)—FPPS$^{Pr}$)

a) Propyl 4-propoxypicolinate

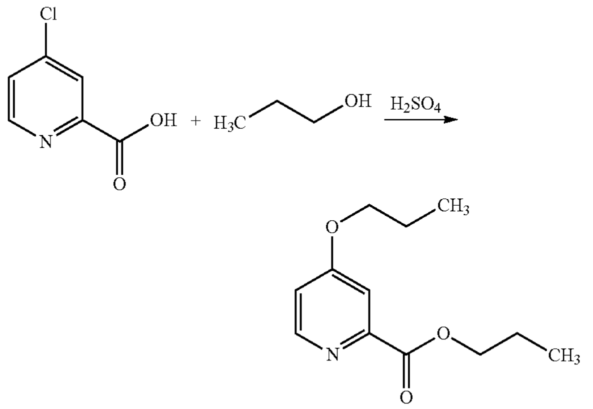

To a solution of 4-chloropicolinic acid (250 g; 1586.76 mmol; 1.0 eq.) was charged 1-PrOH (2250 mL) and $H_2SO_4$ (100.98 mL; 1904.1091 mmol; 1.2 eq.). After 18 h at 90° C., 1250 mL of 1-PrOH was distilled under 10 mbar at 35° C. Water (250 mL) was added followed by careful addition of solid $NaHCO_3$ (319.89 g; 3808.2181 mmol; 2.4 eq.) to reach pH 7-8. The product was extracted with MTBE (500 mL×3). The combined organic layer was washed with 500 mL of water. After concentration, the product was isolated with 57% yield.

$^1$H NMR (400 MHz, $CDCl_3$): δ 8.54 (d, J=5.64 Hz, 1H), 7.64 (d, J=2.56 Hz, 1H), 6.95 (dd, J=2.56, 5.64 Hz, 1H), 4.37 (t, J=6.96 Hz, 2H), 4.04 (t, J=6.56 Hz, 2H), 1.90-1.81 (m, 4H), 1.08-1.00 (m, 6H). $^{13}$C NMR (100 MHz, $CDCl_3$): δ 166.0, 165.4, 151.0, 149.9, 113.2, 111.7, 69.9, 67.5, 22.2, 22.0, 10.4. HRMS (ES pos.): m/z calcd for $C_{12}H_{18}NO_3$ (M+H$^+$): 224.12812, found: 224.12805.

b) methyl 3-(4-chloropyridin-2-yl)-3-oxopropanoate

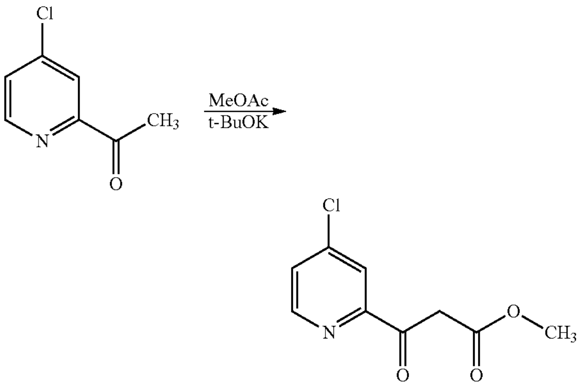

To a dry and clean reactor was charged KOt-Bu (269.2 g, 2398.87 mmol, 2.1. eq.) and THF (2 L). After the mixture was cooled to −10° C., MeOAc (186.2 g, 2513.1 mmol, 2.2 eq.) was added below $T_r$=0° C. The charging line was rinsed with with THF (1 L) into the reactor. After 0.5 h at 0 to −5° C., a thin slurry of methyl 4-chloropicolinate (200 g, 1142.3 mmol, 1.0 eq.) in THF (800 mL) was charged below 2° C. The charging line was rinsed with THF (100 mL) into the reactor. After 0.5 h at 0-5° C., HOAc (205.8 g, 3426.95 mmol, 3.0 eq.) was charged below 25° C. followed by addition of $H_2O$ (400 mL) in one portion to obtain a homogenous solution. The organic solvents (ca. 3000 mL) were removed under vacuum at 30-40° C. After MeOH (1200 mL) was added, the organic solvent (ca. 600 mL) was removed under vacuum at 30-35° C. After the mixture was cooled to 20-23° C. at least over 1 h. Water (1600 mL) was added over 0.5 h. After 1 h at 20-23° C., the solid was collected by filtration and then washed with $H_2O$ (400 mL). The solid was dried under vacuum by passing nitrogen through the wet cake. The product was isolated with 93-95% yield.

c) 1-(4-Chloropyridin-2-yl)ethan-1-one

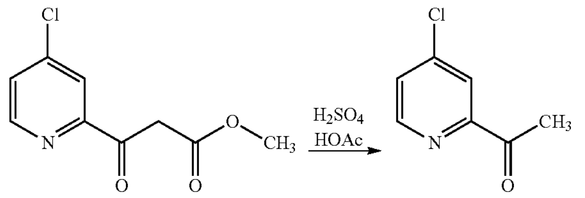

To a dry and clean reactor was charged methyl 3-(4-chloropyridin-2-yl)-3-oxopropanoate (559 g, 2.62 mol, containing tautomer), $H_2O$ (999 mL), HOAc (550 g) and $H_2SO_4$ (333 g). After 2 h at 85° C., the mixture was cooled to 5-20° C. After 1-methylpyrrolidine (1114 g) was added below 30° C. and the charge line was rinsed with $H_2O$ (838 mL) at 20-30° C. into the reactor below 30° C., the product was extracted with EtOAc (2236 mL). After phase cut, the organic layer was washed with $H_2O$ (559 mL). After removal of the solvent under vacuum below 45° C., the product was dried by co-evaporation with toluene (559 mL). A typical yield is 85-90%.

d) 1-(4-Propoxypyridin-2-yl)ethan-1-one

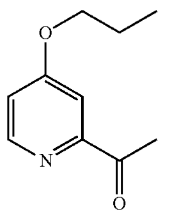

Procedure A i) Propyl 3-oxo-3-(4-propoxypyridin-2-yl)propanoate

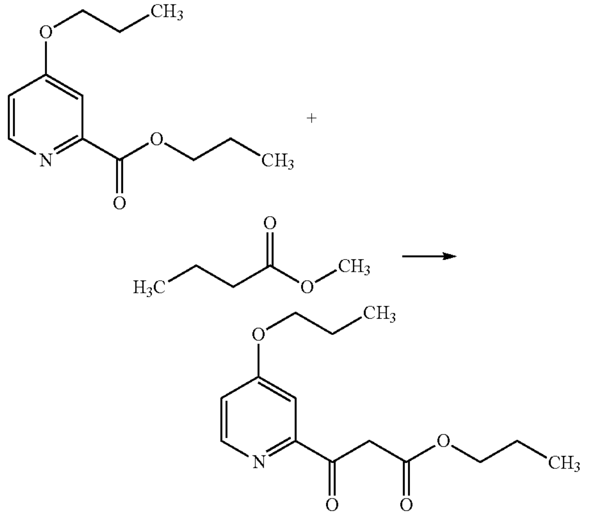

To a dry flask was charged KOt-Bu (11.06 g; 98.5 mmol) and THF (100 mL). After cooling the solution to −10° C., n-PrOAc (11.40 mL; 98.5 mmol; 2.2 eq.) was added below 0° C. After 10 min, 4-propoxy-pyridine-2-carboxylic acid propyl ester (10 g; 44.79 mmol; 1.0 eq.) was added below 0° C. After 0.5 h, HOAc (8.97 mL; 156.76 mmol; 3.500 eq.) was added below 25° C. followed by addition of water (20 mL) to obtain a homogenous solution. After removal of THF under vacuum, the product was extracted with ethyl acetate (60 mL) and washed with water (20 mL). After concentration, the product propyl 3-oxo-3-(4-propoxypyridin-2-yl) propanoate was used for the next step.

ii) 1-(4-Propoxypyridin-2-yl)ethan-1-one

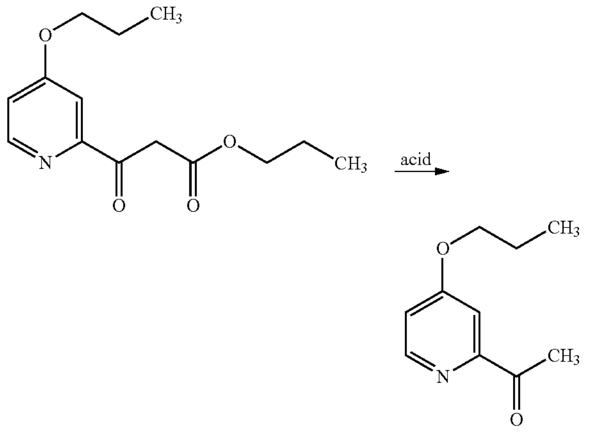

To a flask was charged propyl 3-oxo-3-(4-propoxypyridin-2-yl)propanoate (270 g; 1017.7 mmol; 1.0 eq.), HOAc (277.78 mL), water (405 mL) and $H_2SO_4$ (81.31 mL). After heating to 98° C. for 2 h, the mixture was cooled to 0° C., water (270 mL) was added followed by addition of 50% NaOH to reach pH=5.5 (ca. 376 mL). Additional water was added to dissolve the salt solid. The product was extracted with EtOAc (330 mL) two times. The organic layer was washed with aq. $NaHCO_3$ (220 mL) and water (220 mL). The crude product was treated with 10% activated carbon at room temperature. After filtration and concentration, the product was isolated with 89% yield and used for the next step.

Procedure B

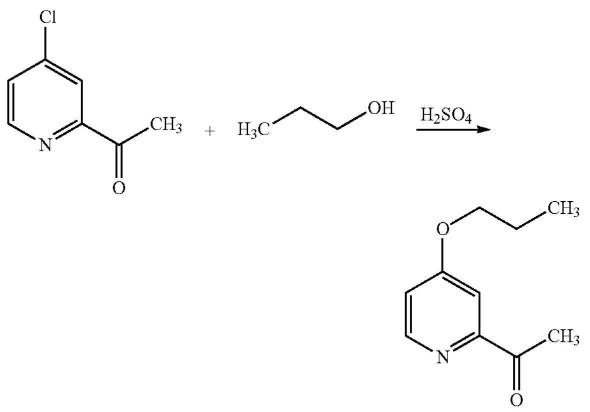

To a dry and clean reactor was charged 1-(4-chloropyridin-2-yl)ethan-1-one (100 g, 642 mmol) and 1-PrOH (1000 mL) followed by addition of $H_2SO_4$ (75.3 g, 1.2 eq.). The charging line was rinsed with 1-PrOH (300 mL). The resulting mixture was heated at 90° C. at least for 20 h. After 1100 mL of 1-PrOH was distilled under vacuum at 55-60° C., water was added. After 0.5 h at 55-60° C., the mixture was cooled to 23° C. Pyridine (155.6 mL, 3.0 eq.) was added at 20-25° C. followed by addition of toluene (600 mL). After phase cut, the organic layer was washed with aq. N(257 mL, 0.5 M, 0.20 eq.) at 20-25° C. After phase cut, the organic layer was washed with $H_2O$ (300 mL) two times. The organic layer was passed through Cuno carbon 55 at the flow rate 10 mL/min. The carbon was washed with 200 mL toluene. After concentration, the crude product was used for the next step. A typical yield is 70-75%.

$^1H$ NMR (400 MHz, $CDCl_3$): δ 8.47 (d, J=5.64 Hz, 1H), 7.55 (s, 1H), 6.96 (m, 1H), 4.03 (t, J=6.56 Hz, 2H), 2.71 (s, 3H), 1.89-1.80 (m, 2H), 1.05 (t, J=7.36 Hz, 3H). $^{13}C$ NMR (100 MHz, $CDCl_3$): δ 200.1, 166.0, 155.4, 150.1, 114.2, 107.3, 69.8, 25.9, 22.2, 10.3. HRMS (ES pos.): m/z calcd for $C_{10}H_{14}NO_2$ (M+H$^+$): 180.10191, found: 180.10182.

e) (R)-1-(4-Propoxypyridin-2-yl)ethan-1-ol

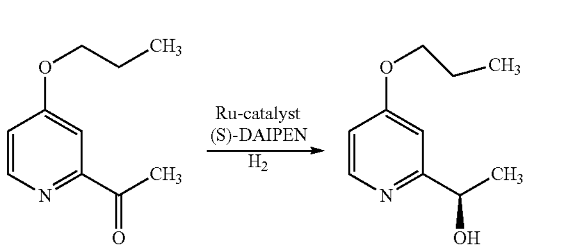

To a reactor was added 1-(4-propoxypyridin-2-yl)ethan-1-one (678.2 g, 3784.0 mmol), $RuCl_2$[(S)-xylBINAP][(S)-DAIPEN] (9.24 g, 7.57 mmol), potassium 3,7-dimethyl-3-octylate (55.58, 50% in heptane, 113.5 mmol) and 2-PrOH (3173 mL). The mixture was stirred at 31.03 bar (450 psi) $H_2$ at 20-21° C. for 30 min. The solution was concentrated and heptane (900 mL) was added. The mixture was stirred overnight. The solid was collected and washed with heptane (700 mL). A total of 603 g of the product was isolated as a solid with 99:1 er and 83% yield.

$^1H$ NMR (400 MHz, $CDCl_3$): δ 8.31 (d, J=5.76 Hz, 1H), 6.79 (d, J=2.44 Hz, 1H), 6.70 (dd, J=2.44, 5.76 Hz, 1H), 4.82 (q, J=6.56, 13.08 Hz, 1H), 4.43 (bs, 1H), 3.97 (t, J=6.56 Hz, 2H), 1.87-1.78 (m, 2H), 1.49 (d, J=6.52 Hz, 3H), 1.04 (t, J=7.40 Hz, 3H). $^{13}C$ NMR (100 MHz, $CDCl_3$): δ 165.9, 165.1, 149.3, 109.1, 105.7, 69.5, 69.0, 24.2, 22.3, 10.4. HRMS (ES pos.): m/z calcd for $C_{10}H_{16}NO_2$ (M+H$^+$): 182.11756, found: 182.11752. Chiral HPLC conditions: Chiralpak AD-3, 4.6×250 mm; 94:6 heptane/ethanol, 1.3 mL/min, 220 nm, (R)-isomer, t=8.39 min, (S)-isomer, t=8.98 min.

f1) O-((9H-fluoren-9-yl)methyl)O—((R)-1-(4-propoxypyridin-1-ium-2-yl)ethyl) (R)-phosphorothioate ((R, $R_p$)—FPPS$^{Pr}$)

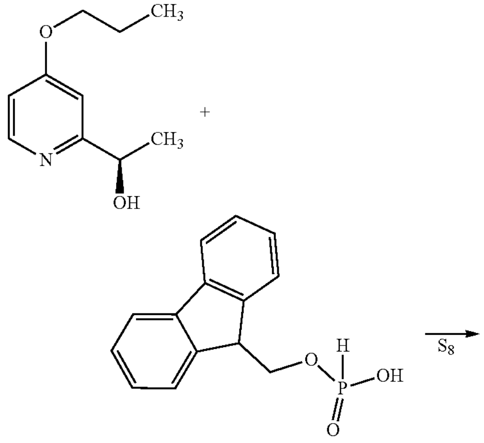

-continued

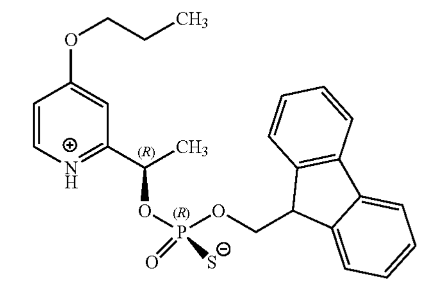

To a a dry and clean reactor was charged (R)-1-(4-propoxypyridin-2-yl)ethan-1-ol (312.9 g, 1.73 mol, 1.0 eq) and [(9H-fluoren-9-yl)methoxy]phosphinic acid (493.89 g, 1.90 mol, 1.1 eq.). After pyridine (990 mL) was added, PivCl (294.2 g, 2.42 mol, 1.4 eq.) was added while maintaining the temperature at 20-25° C. After more than 0.5 h at 20-25° C., $H_2O$ (62.2 g, 3.45 mol, 2.0 eq.) was added to quench the reaction. Sulfur (59.09 g, 1.81 mol, 1.05 eq.) was added while maintaining the temperature below 35° C. After 2-3 h, MeOH (990 mL) was added at 20-25° C. over 0.5 h followed by addition of $H_2O$ (1980 mL) at 20-25° C. over 0.5 h. After 1 h at 20-23° C., the solid was collected and washed with a solution of MeOH (1155 mL) and $H_2O$ (231 mL). The wet cake was charged into a clean reactor followed by addition of MeOH (1980 mL). After 0.5 h, $H_2O$ (396 mL) was added. After 0.5 h, the solid was collected again and washed with MeOH (160 mL). The wet cake was charged into a clean reactor and then toluene (2500 mL) was added. After 2 h at 25±2° C., the solid was collected and washed with toluene (300 mL). After drying under vacuum below 30° C., the product was isolated as a solid with 39% yield and >98:2 dr.

$^1H$ NMR (600 MHz, pyridine-$d_5$): δ 8.49 (d, J=5.64 Hz, 1H), 7.84 (d, J=7.44 Hz, 1H), 7.79-7.76 (m, 3H), 7.56 (d, J=2.46 Hz, 1H), 7.34 (dd, J=7.14, 13.98 Hz, 2H), 7.24-7.21 (m, 2H), 6.74 (dd, J=2.46, 5.58 Hz, 1H), 6.28 (m, 1H), 4.75-4.71 (m, 1H), 4.66-4.62 (m, 1H), 4.48 (t, J=7.26 Hz, 1H), 3.74 (t, J=6.48 Hz, 2H), 1.93 (d, J=6.60 Hz, 3H), 1.62-1.56 (m, 2H), 0.81 (t, J=7.44 Hz, 3H). $^{13}C$ NMR (150 MHz, pyridine-$d_5$): δ 166.1, 165.1 [d, J (P,C)=5.69 Hz], 150.1, 144.8, 144.7, 141.4, 141.4, 127.7, 127.7, 127.2, 127.1, 125.8, 125.7, 120.1, 120.1, 109.3, 107.0, 75.7 [d, J (P,C)=5.1 Hz], 69.3, 68.6 [d, J (P,C)=5.5 Hz], 48.6 [d, J (P,C)=8.5 Hz], 23.3 [d, J (P,C)=4.2 Hz], 22.2, 10.2. HRMS (ES pos.): m/z calcd for $C_{24}H_{27}NO_4PS$ (M+H$^+$): 456.13929, found: 456.13913.

f2) O-((9H-fluoren-9-yl)methyl)O—((S)-1-(4-propoxypyridin-1-ium-2-yl)ethyl) (S)-phosphorothioate ((S, $S_p$)-FPPS$^{Pr}$)

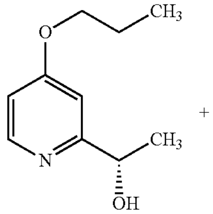

-continued

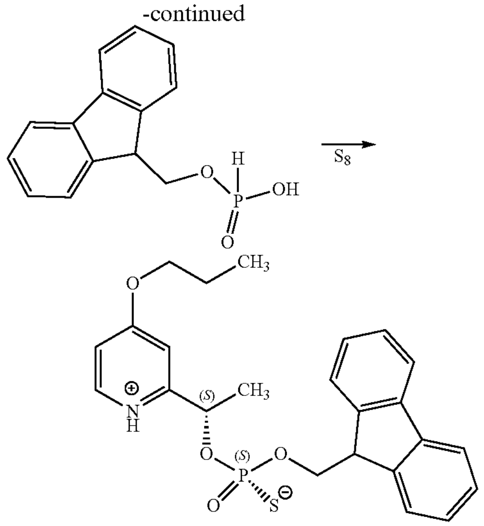

To a a dry and clean reactor was charged (S)-1-(4-propoxypyridin-2-yl)ethan-1-ol (4.0 g, 22.1 mmol) and [(9H-fluoren-9-yl)methoxy]phosphinic acid (6.48 g, 24.3 mmol, 1.1 eq.). After pyridine (12 mL) was added, PivCl (4.05 g, 33.1 mmol, 1.5 eq.) was added while maintaining the temperature at 20-25° C. After more than 0.5 h at 20-25° C., $H_2O$ (0.8 mL, 44.1 mmol, 2.0 eq.) was added to quench the reaction. Sulfur (0.78 g, 24.3 mmol, 1.1 eq.) was added while maintaining the temperature below 35° C. After 2-3 h, MeOH (12 mL) was added at 20-25° C. over 0.5 h followed by addition of $H_2O$ (24 mL) at 20-25° C. over 0.5 h. After 1 h at 20-23° C., the solid was collected and washed with a solution of MeOH (15 mL) and $H_2O$ (3 mL). The wet cake was charged into a clean reactor and then toluene (100 mL) was added. After 2 h at 25±2° C., the solid was collected and washed with toluene (20 mL). After dried under vacuum below 30° C., the product was isolated as a solid with 35% yield and >98:2 dr.

HRMS (ES pos.): m/z calcd for $C_{24}H_{27}NO_4PS$ (M+H$^+$): 456.13929, found: 456.13906.

g1) Purification of O-((9H-fluoren-9-yl)methyl)O—((R)-1-(4-propoxypyridin-1-ium-2-yl)ethyl) (S)-phosphorothioate ((R, $S_p$)-FPPS$^{Pr}$)

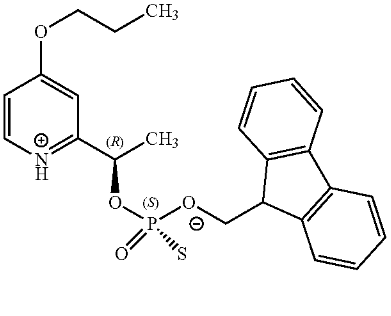

After isolation of O-((9H-fluoren-9-yl)methyl)O—((R)-1-(4-propoxypyridin-1-ium-2-yl)ethyl) (R)-phosphorothioate, the mother liquor was concentrated to remove most of the MeOH. The residue was diluted with EtOAc and water. After the organic layer was washed with 2M $KHSO_4$ to remove pyridine and then with water, the organic solvent was removed under vacuum. The residue was purified by silical gel column chromatography. After the column was equilibrated with hexane, the column was preloaded with $CH_2Cl_2$ and then the crude product was loaded on the column with the help of $CH_2Cl_2$. The column was first washed with 0-100% EtOAc. After that, 0-10% MeOH in $CH_2Cl_2$ was used to elute the product. After the fraction was collected and concentrated, the product was obtained as a foam solid. The foam solid was further mixed with EtOAc to prepare a slurry in EtOAc. The solid was collected and washed with EtOAc. After drying under vacuum, the product was isolated in 90:10 dr as a solid.

HRMS (ES pos.): m/z calcd for $C_{24}H_{27}NO_4PS$ (M+H$^+$): 456.13929, found: 456.13901.

Application/Use of the Synthons

Example 5

General Procedure for the Synthesis of Monomers:

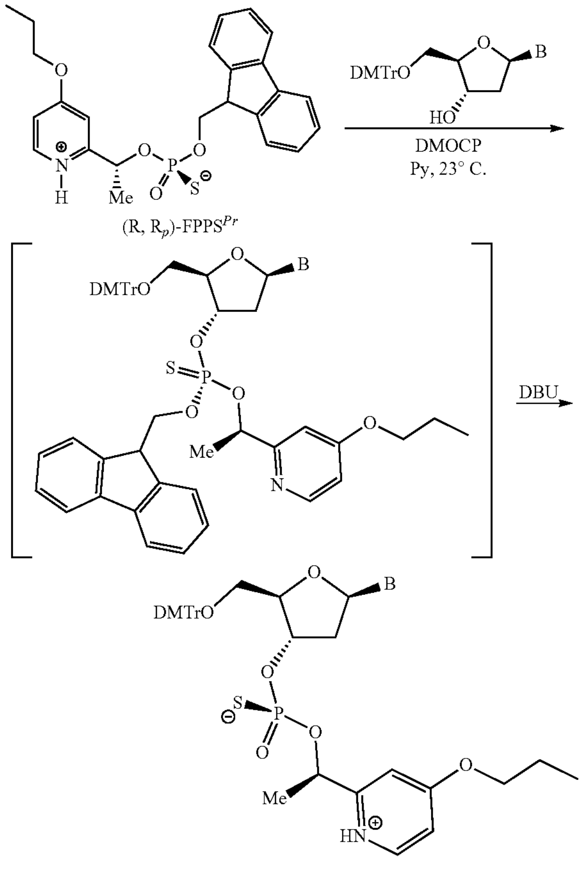

B=nitrogenous base of the nucleoside

To a dry and clean flask was charged 1 g of the nucleoside dA, dC, dG or dT with DMTr as the protection group and the synthon selected from FPPS$^{Me}$, (R, $R_p$)—FPPS$^{Et}$, (S, $S_p$)—FPPS$^{Et}$, (R, $R_p$)—FPPS$^{Pr}$, (S, $S_p$)—FPPS$^{Pr}$, and (R, $S_p$)—FPPS$^{Pr}$. The mixture was dried by evaporation of 3 mL of pyridine. After 3 mL of pyridine was added, DMOCP (2.6 eq.) was added in one portion. After 1-2 h, 0.1 mL of water was added, the mixture was stirred for 10 min. 1 mL of DBU was added. After 30 min, the mixture was diluted with 5 mL of water, 7 mL of aq. 2M $KHSO_4$ and 10 ml of EtOAc. After phase cut, the organic layer was washed with 8 mL of aq. 2M $KHSO_4$ and then 2 ml of water. After concentration, the crude product was isolated and used for next step directly. An analytic sample was purified by silica gel column chromatography. The column was preloaded with $CH_2Cl_2$ and then the crude product was loaded on the column with the help of $CH_2Cl_2$. The column was first washed with 0-100% EtOAc. After that, 0-10% MeOH in $CH_2Cl_2$ was used to elute the product. Then, the fraction was collected and concentrated, the product was obtained as a foam solid.

Specific Examples for the Synthesis of Monomers

Example 5.1. dA-P(V) Prepared by Using dA as Nucleoside and (R, $R_p$)-FPPS$^{Pr}$ as Synthon

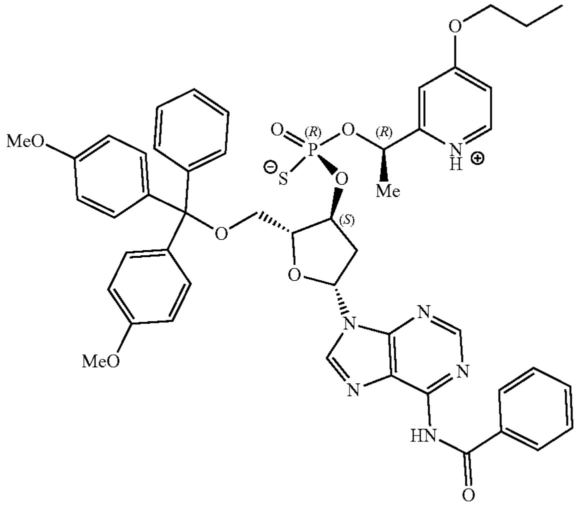

To a dry and clean flask was charged the nucleoside N-6-benzoyl-5'-O-(4,4'-dimethoxytrityl)-2'-deoxyadenosine (dA; 1 g, 1.52 mmol) and O-((9H-fluoren-9-yl)methyl) 0-((R)-1-(4-propoxypyridin-1-ium-2-yl)ethyl) (R)-phosphorothioate ((R, $R_p$)—FPPS$^{Pr}$, 0.73 g, 1.58 mmol). The mixture was dried by evaporation of 3 mL of pyridine. After 3 mL of pyridine was added, 2-chloro-5,5-dimethyl-1,3,2-dioxaphosphorinane-2-oxide (DMOCP; 0.73 g, 3.95 mmol, 2.6 eq.) was added in one portion. After 1-2 h, 0.1 mL of water was added, the mixture was stirred for 10 min. 1 mL of DBU was added. After 30 min, the mixture was diluted with 5 mL of water, 7 mL of aq. 2M $KHSO_4$ and 10 mL of EtOAc. After phase cut, the organic layer was washed with 8 mL of aq. 2M $KHSO_4$ and then with 2 ml of water. After concentration, the crude product was purified by silica gel column chromatography. The column was preloaded with $CH_2Cl_2$ and then the crude product was loaded on the column with the help of $CH_2Cl_2$. The column was first washed with 0-100% EtOAc. After that, 0-10% MeOH in $CH_2Cl_2$ was used to elute the product. After the fraction was collected and concentrated, 1.31 g of the product was obtained as a foam solid with >97.5:2.5 dr and 94% yield.

$^1$H NMR (500 MHz, DMSO-$d_6$): δ 8.61 (s, 1H), 8.55 (s, 1H), 8.06 (d, J=7.3 Hz, 2H), 7.65 (t, J=7.3 Hz, 1H), 7.55 (t, J=7.8 Hz, 2H), 7.41 (s, 1H), 7.37 (d, J=7.35 Hz, 2H), 7.26-7.16 (m, 8H), 6.81 (t, J=9.35 Hz, 4H), 6.47 (t, J=6.45 Hz, 1H), 5.62 (m, 1H), 5.18 (bs, 1H), 4.39 (bs, 1H), 4.17 (t, J=6.4 Hz, 2H), 3.71 (s, 3H), 3.71 (s, 3H), 3.32 (m, 1H), 3.25 (m, 1H), 3.11 (m, 1H), 2.63 (m, 1H), 1.78-1.71 (m, 2H), 1.52 (d, J=6.6 Hz, 3H), 0.94 (t, J=7.35 Hz, 3H). $^{13}$C NMR (126 MHz, DMSO-$d_6$): δ 169.7, 166.2, 161.0, 158.5, 158.5, 152.4, 151.9, 150.9, 145.3, 145.2, 136.1, 135.9, 133.9, 132.9, 130.2, 130.1, 129.4, 129.1, 129.0, 128.9, 128.3, 128.2, 127.9, 127.1, 126.4, 113.6, 111.1, 109.6, 86.1, 85.5 [d, J (P, C)=5.6 Hz], 84.7, 76.4, [d, J (P, C)=5.7 Hz], 71.5, 71.0, 64.5, 37.4, 22.5 [d, J (P, C)=5.3 Hz], 22.0, 10.5. $^{31}$P NMR (202 MHz, DMSO-$d_6$): δ 55.76. HRMS (ES pos.): m/z calcd for $C_{48}H_{50}N_6O_9PS$ (M+H$^+$): 917.30921, found: 917.30886.

Example 5.2. dC-P(V) Prepared by Using dC as Nucleoside and (R, $R_p$)-FPPS$^{Pr}$ as Synthon

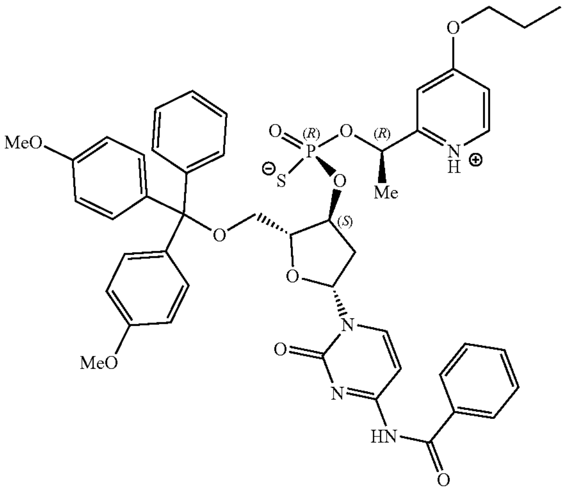

To a dry and clean flask was charged the nucleoside 5'-O-dimethoxytrityl-N-benzoyl-deoxycytidine (dC; 1 g, 1.58 mmol) and O-((9H-fluoren-9-yl)methyl) 0-((R)-1-(4-propoxypyridin-1-ium-2-yl)ethyl) (R)-phosphorothioate ((R, $R_p$)—FPPS$^{Pr}$; 0.76 g, 1.64 mmol). The mixture was dried by evaporation of 3 mL of pyridine. After 3 mL of pyridine was added, 2-chloro-5,5-dimethyl-1,3,2-dioxaphosphorinane-2-oxide (DMOCP; 0.76 g, 4.10 mmol, 2.6 eq.) was added in one portion. After 1-2 h, 0.1 mL of water was added, the mixture was stirred for 10 min. 1 mL of DBU was added. After 30 min, the mixture was diluted with 5 mL of water, 7 mL of aq. 2M $KHSO_4$ and 10 ml of EtOAc. After phase cut, the organic layer was washed with 8 mL of aq. 2M $KHSO_4$ and then with 2 mL of water. After concentration, the crude product was purified by silica gel column chromatography. The column was preloaded with $CH_2Cl_2$ and then the crude product was loaded on the column with the help of $CH_2Cl_2$. The column was first washed with 0-100% EtOAc. After that, 0-10% MeOH in $CH_2Cl_2$ was used to elute the product. After the fraction was collected and concentrated, 1.35 g of the product was obtained as a foam solid with >99:1 dr and 96% yield.

$^1$H NMR (500 MHz, DMSO-$d_6$): δ 8.58 (d, J=6.55 Hz, 1H), 8.12 (d, J=7.45 Hz, 1H), 8.00 (d, J=7.35 Hz, 2H), 7.63 (t, J=7.40 Hz, 1H), 7.52 (t, J=7.90 Hz, 2H), 7.42-7.38 (m, 3H), 7.33-7.15 (m, 9H), 6.89 (dd, J=1.35, 8.75 Hz, 4H), 6.13 (t, J=6.35 Hz, 1H), 5.59 (m, 1H), 5.08 (m, 1H), 4.33 (m, 1H), 4.20 (t, J=6.25 Hz, 2H), 3.73 (s, 3H), 3.73 (s, 3H), 3.39 (dd, J=4.65, 10.65 Hz, 1H), 3.25 (dd, J=2.45, 10.91 Hz, 1H), 2.59 (m, 1H), 2.24 (m, 1H), 1.81-1.72 (m, 2H), 1.50 (d, J=6.60 Hz, 3H), 0.96 (t, J=7.30 Hz, 3H). $^{13}$C NMR (126 MHz, DMSO-$d_6$): δ 169.9, 167.9, 163.5, 160.7, 158.6, 158.6, 154.7, 144.9, 144.6, 135.8, 135.6, 133.6, 133.2, 130.3, 130.2, 129.4, 128.9, 128.9, 128.4, 128.2, 113.7, 113.2, 111.3, 109.7, 96.6, 86.9, 86.6, 85.5 [d, J (P, C)=6.6 Hz], 75.3, 71.6, 70.7, 63.6, 55.5, 55.5, 22.3 [d, J (P. C)=5.7 Hz], 21.9, 10.51. $^{31}$P NMR (202 MHz, DMSO-$d_6$): δ 55.80.

Example 5.3. dG-P(V) Prepared by Using dG as Nucleoside and (R, $R_p$)—FPPS$^{Pr}$ as Synthon

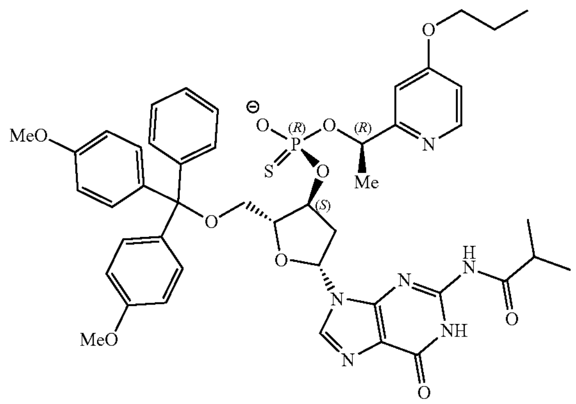

To a dry and clean flask was charged the nucleoside 5'-O-(4,4'-dimethoxytrityl)-N-isobutyl-deoxyguanosine (dG; 1 g, 1.56 mmol) and O-((9H-fluoren-9-yl)methyl) 0-((R)-1-(4-propoxypyridin-1-ium-2-yl)ethyl) (R)-phosphorothioate ((R, $R_p$)-FPPS$^{Pr}$; 0.75 g, 1.63 mmol). The mixture was dried by evaporation of 3 mL of pyridine. After 3 mL of pyridine was added, 2-chloro-5,5-dimethyl-1,3,2-dioxaphosphorinane-2-oxide (DMOCP (0.75 g, 4.06 mmol, 2.6 eq.) was added in one portion. After 1-2 h, 0.1 mL of water was added, the mixture was stirred for 10 min. 1 mL of DBU was added. After 30 min, the mixture was diluted with 5 mL of water, 7 mL of aq. 2M $KHSO_4$ and 10 ml of EtOAc. After phase cut, the organic layer was washed with 8 mL of aq. 2M $KHSO_4$ and then with 2 mL of water. After concentration, the crude product was purified by silica gel column chromatography. The column was preloaded with $CH_2Cl_2$ and then the crude product was loaded on the column with the help of $CH_2Cl_2$. The column was first washed with 0-100% EtOAc. After that, 0-10% MeOH in $CH_2Cl_2$ was used to elute the product. After the fraction was collected and concentrated, 1.3 g of the product was obtained as a foam solid with >99:1 dr and 93% yield.

$^1$H NMR (500 MHz, DMSO-$d_6$): δ 12.04 (s, 1H), 11.74 (s, 1H), 8.56 (d, J=6.55 Hz, 1H), 8.04 (s, 1H), 7.38 (s, 1H), 7.34 (d, J=7.35 Hz, 2H), 7.25-7.18 (m, 8H), 6.82 (d, J=9.15 Hz, 2H), 6.80 (d, J=9.15 Hz, 2H), 6.27 (m, 2H), 5.55 (m, 1H), 5.02 (m, 1H), 4.30 (m, 1H), 4.17 (t, J=6.30 Hz, 2H), 3.72 (s, 6H), 3.29 (m, 1H), 3.12 (m, 1H), 2.81 (m, 1H), 2.73 (m, 1H), 2.56 (m, 1H), 1.78-1.72 (m, 2H), 1.47 (d, J=6.65 Hz, 3H), 1.12 (d, J=6.80 Hz, 6H), 0.95 (t, J=7.35 Hz, 3H). $^{13}$C NMR (126 MHz, DMSO-$d_6$): δ 180.5, 169.7, 160.9, 158.5, 158.5, 155.3, 149.1, 148.6, 145.2, 137.5, 135.9, 135.9, 130.2, 130.1, 128.2, 128.2, 127.1, 120.8, 113.6, 111.1, 109.6, 86.1, 85.4 [d, J (P, C)=6.01 Hz], 83.7, 76.3 [d, J (P, C)=5.75 Hz], 71.5, 70.9, 64.7, 55.5, 55.4, 38.0, 35.3, 22.4 [d, J (P, C)=4.81 Hz], 21.9, 19.2, 10.5. $^{31}$P NMR (202 MHz, DMSO-$d_6$): δ 55.10. HRMS (ES pos.): m/z calcd for $C_{45}H_{52}N_6O_{10}PS$ (M+H$^+$): 899.31978, found: 899.31999.

Example 5.4. dT-P(V) Prepared by Using dT as Nucleoside and (R, $R_p$)-FPPS$^{Pr}$ as Synthon

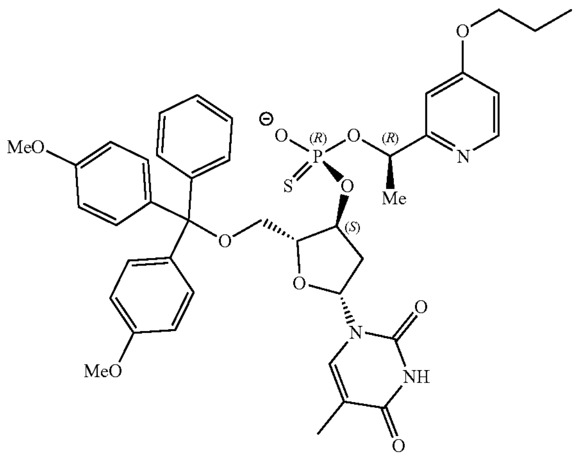

To a dry and clean flask was charged the nucleoside 5'-O-(4,4'-dimethoxytrityl)thymidine (dT; 1 g, 1.84 mmol) and O-((9H-fluoren-9-yl)methyl) 0-((R)-1-(4-propoxypyridin-1-ium-2-yl)ethyl) (R)-phosphorothioate ((R, $R_p$)—FPPS$^{Pr}$; 0.88 g, 1.01 mmol). The mixture was dried by evaporation of 3 mL of pyridine. After 3 mL of pyridine was added, 2-chloro-5,5-dimethyl-1,3,2-dioxaphosphorinane-2-oxide (DMOCP (0.88 g, 4.77 mmol, 2.6 eq.) was added in one portion. After 1-2 h, 0.1 mL of water was added, the mixture was stirred for 10 min. 1 mL of DBU was added. After 30 min, the mixture was diluted with 5 mL of water, 7 mL of aq. 2M $KHSO_4$ and 10 mL of EtOAc. After phase cut, the organic layer was washed with 8 mL of aq. 2M $KHSO_4$ and then with 2 mL of water. After concentration, the crude product was purified by silica gel column chromatography. The column was preloaded with $CH_2Cl_2$ and then the crude product was loaded on the column with the help of $CH_2Cl_2$. The column was first washed with 0-100% EtOAc. After that, 0-10% MeOH in $CH_2Cl_2$ was used to elute the product. After the fraction was collected and concentrated, 1.4 g of the product was obtained as a foam solid with >99:1 dr and 95% yield.

$^1$H NMR (500 MHz, DMSO-$d_6$): δ 11.37 (s, 1H), 8.57 (d, J=6.55 Hz, 1H), 7.49 (s, 1H), 7.42-7.39 (m, 3H), 7.32-7.22 (m, 8H), 6.89 (d, J=8.75 Hz, 4H), 6.19 (m, 1H), 5.61 (m, 1H), 5.14 (m, 1H), 4.23 (s, 1H), 4.18 (m, 2H), 3.73 (s, 6H), 3.35 (m, 1H), 3.15 (m, 1H), 2.39-2.29 (m, 2H), 1.78-1.71 (m, 2H), 1.49 (d, J=6.65 Hz, 3H), 1.36 (s, 3H), 0.95 (t, J=7.35 Hz, 3H). $^{13}$C NMR (126 MHz, DMSO-$d_6$): δ 169.9, 164.1, 160.7, 158.7, 158.6, 150.8, 145.1, 135.9, 135.8, 135.6, 130.2, 130.2, 128.4, 128.1, 127.3, 113.8, 111.3, 110.2, 110.0, 86.6, 84.9 [d, J (P, C)=5.63 Hz], 84.3, 76.3 [d, J (P, C)=5.67 Hz], 71.6, 70.8, 64.3, 55.5, 55.5, 38.6 [d, J (P, C)=4.35 Hz], 21.9, 12.0, 10.5. $^{31}$P NMR (202 MHz, DMSO-$d_6$): δ 55.76. HRMS (ES pos.): m/z calcd for $C_{41}H_{47}N_3O_{10}PS$ (M+H$^+$): 804.27143, found: 804.27152.

Analogously were Prepared:

5.5. dT-P(V) from FPPS$^{Me}$

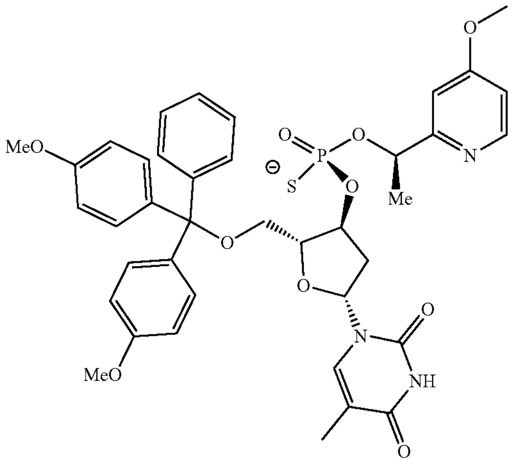

dT-P(V) FPPS$^{Me}$ $^{1}$H NMR (500 MHz, DMSO-$d_6$): δ 11.37 (s, 1H), 8.54 (d, J=6.35 Hz, 1H), 7.50 (s, 1H), 7.41 (s, 1H), 7.39 (s, 2H), 7.32-7.22 (m, 8H), 6.89 (d, J=7.75 Hz, 4H), 6.19 (t, J=8.1 Hz, 1H), 5.59 (m, 1H), 5.14 (m, 1H), 4.26 (s, 1H), 3.96 (s, 3H), 3.73 (s, 6H), 3.36 (m, 1H), 3.15 (m, 1H), 2.34-2.31 (m, 2H), 1.48 (d, J=6.55 Hz, 3H), 1.36 (s, 3H). $^{13}$C NMR (125 MHz, DMSO-$d_6$): δ 168.9, 164.1, 161.5, 158.7, 158.6, 150.8, 145.9, 145.1, 135.9, 135.8, 135.6, 130.2, 128.4, 128.1, 127.3, 113.8, 110.7, 110.6, 110.3, 109.0, 86.6, 84.9 [d, J (P, C)=5.4 Hz], 84.3, 76.3 [d, J (P, C)=5.2 Hz], 71.3, 64.4, 57.5, 55.5, 55.5, 38.6 [d, J (P, C)=3.9 Hz], 24.1[d, J (P, C)=4.9 Hz], 12.0. $^{31}$P NMR (202 MHz, DMSO-$d_6$): δ 55.32.

5.6. dT-P(V) from FPPS$^{Et}$

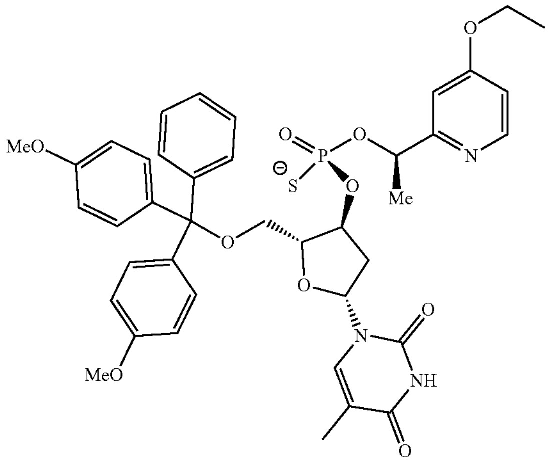

dT-P(V) FPPS$^{Et}$ $^{1}$H NMR (500 MHz, DMSO-$d_6$): δ 11.4 (s, 1H), 8.55 (d, J=6.45 Hz, 1H), 7.50 (s, 1H), 7.40 (s, 1H), 7.39 (s, 2H), 7.31 (t, J=7.5 Hz, 2H), 7.28-7.22 (m, 6H), 6.88 (d, J=7.80 Hz, 4H), 6.19 (m, 1H), 5.58 (m, 1H), 5.14 (m, 1H), 4.30-4.24 (m, 3H), 3.73 (s, 6H), 3.35 (m, 1H), 3.15 (m, 1H), 2.37-2.28 (m, 2H), 1.49 (d, J=6.55 Hz, 3H), 1.36-1.32 (m, 6H). $^{13}$C NMR (125 MHz, DMSO-$d_6$): δ 169.5, 164.1, 161.0, 158.7, 158.6, 150.8, 145.2, 145.1, 135.9, 135.8, 135.6, 130.2, 130.2, 128.4, 128.1, 127.3, 113.8, 111.2, 110.2, 109.5, 85.6, 84.9 [d, J (P, C)=5.4 Hz], 84.3, 76.2 [d, J (P, C)=4.79 Hz], 70.9, 66.0, 64.4, 55.5, 55.5, 38.6 [d, J (P, C)=4.25 Hz], 22.5 [d, J (P, C)=4.93 Hz], 14.5, 12.0. $^{31}$P NMR (202 MHz, DMSO-$d_6$): δ 55.58.

5.7. F—P(V)

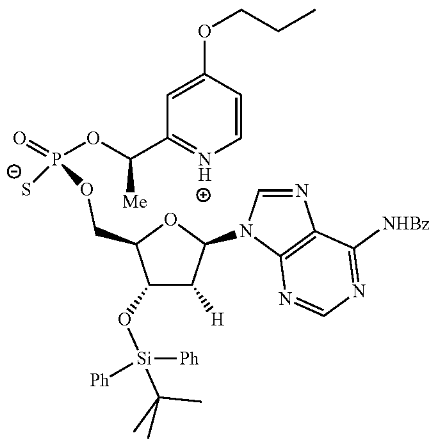

To a dry and clean reactor was charged N-{9-[(2R,3R,4R,5R)-4-[(tert-butyldiphenylsilyl)oxy]-3-fluoro-5-(hydroxymethyl)oxolan-2-yl]-9H-purin-6-yl}benzamide (100 g, 98.4 wt %, 160.85 mmol), O-((9H-fluoren-9-yl)methyl) 0-((R)-1-(4-propoxypyridin-1-ium-2-yl)ethyl) (R)-phosphorothioate ((R, $R_p$)-FPPS$^{Pr}$; 76.97 g, 99.0 wt %, 160.3 mmol, 1.04 eq.) and pyridine (600 mL). After pyridne (450 mL) was removed under vacuum below 40° C., acetonitrile (100 mL) was added at 20-23° C. DMOCP (77.19 g, 418.2 mmol, 2.6 eq) in pyridine (100 mL) was added in less than 10 min. After 1 h, $H_2O$ (10 mL) was added followed by addition of DBU (100 mL) below 35° C. After 30 min, water (500 mL) and EtOAc (1 L) were added followed by 2M $KHSO_4$ (700 mL) at 20-25° C. After phase cut, the organic layer was washed with 2M $KHSO_4$ until aq. phase reached pH 2-3 followed by washing with water (200 mL). The organic layer was cooled to −5° C. and stirred for 1 h, the solid was removed by filtration through a Celite bed. The filtrate was concentrated to give the product with 98% yield. An analytic sample was prepared by silica gel chromatography with 0-100% EtOAc in hexane followed by 0-10% MeOH in $CH_2Cl_2$ as the elute.

$^{1}$H NMR (600 MHz, DMSO-$d_6$): δ 11.22 (s, 1H), 8.76 (s, 1H), 8.65 (s, 1H), 8.49 (d, J=6.30, 2H), 8.04 (d, J=7.44, 2H), 7.67-7.63 (m, 5H), 7.54 (t, J=7.8 Hz, 2H), 7.49-7.42 (m, 6H), 7.30 (s, 1H), 7.16 (bs, 1H), 6.44 (dd, J=4.2, 15.6 Hz, 1H), 5.47 (m, 1H), 5.33 (dt, J=4.2, 52.08 Hz, 1H), 4.79 (m, 1H), 4.26 (bs, 1H), 4.11 (t, J=5.4 Hz, 2H), 4.01 (m, 1H), 3.74 (m, 1H), 1.74-1.68 (m, 2H), 1.36 (d, J=6.6 Hz, 3H), 0.92 (t, J=7.38, 3H). $^{13}$C NMR (150 MHz, DMSO-$d_6$): δ 168.9, 165.6, 160.5, 151.8, 151.7, 150.4, 144.9, 142.7, 135.3, 135.3, 133.3, 132.4, 132.2, 130.1, 130.1, 128.5, 128.4, 128.0, 127.9, 125.4, 110.5, 108.8, 92.9, 91.6, 85.2 [d, J (P, C)=32.61 Hz], 83.7 [d, J (P, C)=7.44 Hz], 71.7 [d, J (P, C)=14.45 Hz], 70.8, 70.4, 64.3 [d, J (P, C)=4.92 Hz], 26.7, 21.7 [d, J (P, C)=4.82 Hz], 21.4, 18.9, 10.0. $^{31}$P NMR (243 MHz, DMSO-$d_6$): δ 56.97. $^{19}$F NMR (565 MHz, DMSO-$d_6$): δ −208.05.

Example 6

Examples for the Synthesis of Phosphorothioate Dimers

Substrate Synthesis

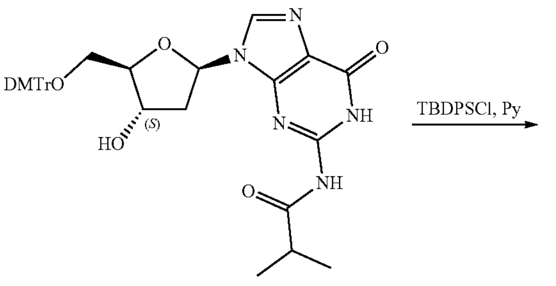

dG

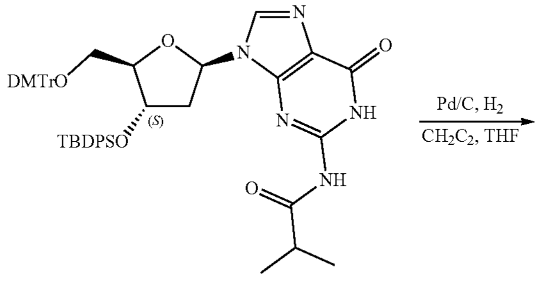

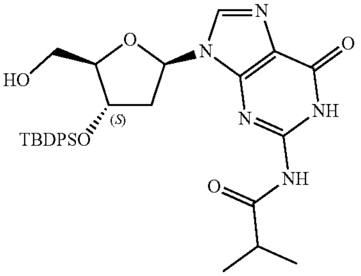

To a solution of dG (15 g, 23.45 mmol) in DMF (30 mL) was charged imidazole (3.99 g, 58.62 mmol) and TBDPSCl (9.7 g, 35.17 mmol). After 5 h at 23° C., the reaction mixture was added slowly to water (1 L). The solid was collected and then washed with water. $CH_2Cl_2$ was added to dissolve the solid. After phase cut to remove some water, the solution was concentrated and then purified on silica gel column with 50-80% EtOAc in hexane.

The product (10 g, 11.4 mmol) was dissolved in THF (30 mL) and $CH_2Cl_2$ (30 mL). After addition of 0.1 g of Pd/C, the reaction mixture was pressurized at 6.8 bar (100 psi) of $H_2$ overnight. After the carbon was filtered off, the crude product was concentrated and then purified by silica gel chromatography with 0-100% EtOAc in hexane.

General Procedure for the Synthesis of Phosphorothioate Dimers

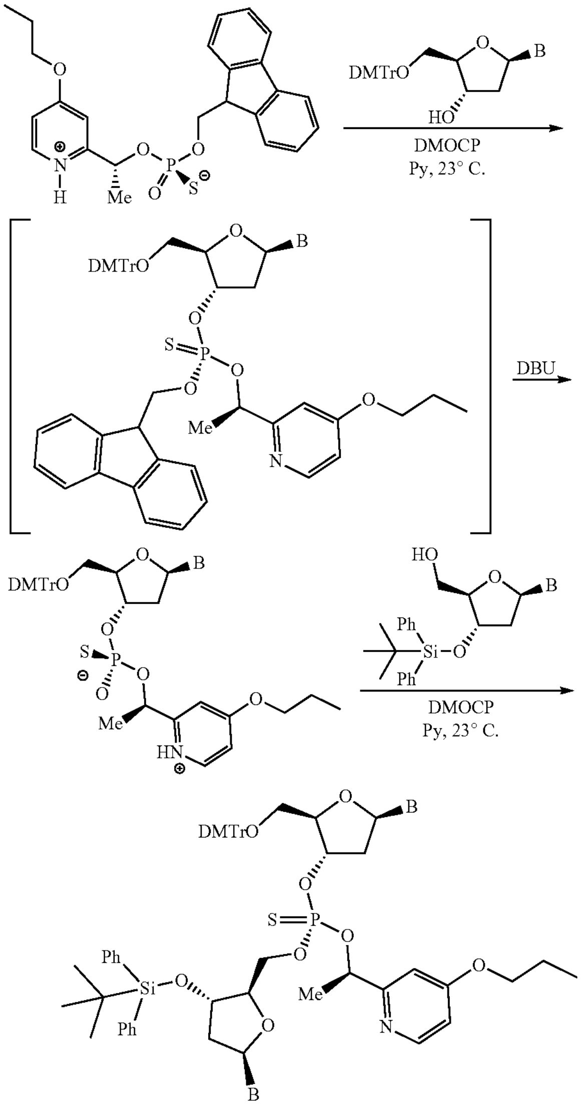

To a dry and clean flask was charged 1 g of the nucleoside phosphorothioate with DMTr as the protection group and monomer dA, dC, dG or dT with TBDPS as the protection group. The mixture was dried by evaporation of 3 mL of pyridine. After 3 mL of pyridine was added, DMOCP (2.8 eq) was added in one portion. After 2 h, 0.1 mL of water was added, the mixture was diluted with 5 mL of water, 7 mL of aq. 2M $KHSO_4$ and 10 mL of EtOAc. After phase cut, the organic layer was washed with 8 mL of aq. 2M $KHSO_4$ and then with 2 mL of water. After concentration, the crude product was obtained. An analytically pure sample was obtained by silica gel column chromatography. The column was preloaded with $CH_2Cl_2$ and then the crude product was loaded on the column with the help of $CH_2Cl_2$. The column was first washed with 0-100% EtOAc. After the fraction was collected and concentrated, the product was obtained as a foam solid.

Specific Examples for the Synthesis of Phosphorothioate Dimers 6.1. dA-dA

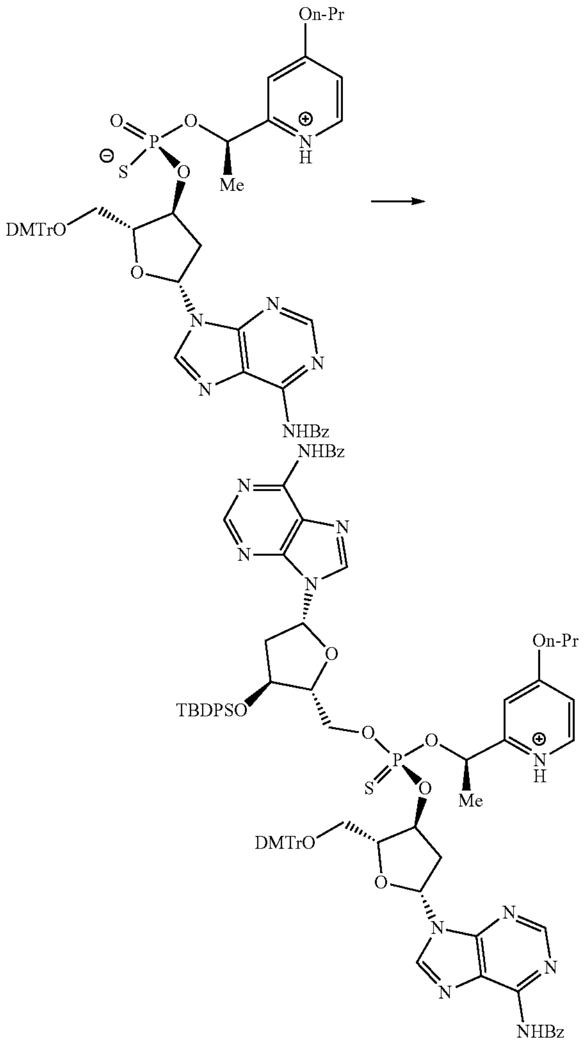

dA-dA

To a dry and clean flask was charged the nucleoside phosphorothioate dA-P(V) (0.73 g, 0.796 mmol) and dA (0.47 g, 0.796 mmol, 1.0 eq.) with TBDPS as the protection group. The mixture was dried by evaporation of 3 mL of pyridine. After 2.2 mL of pyridine was added, DMOCP (0.41 g, 2.22 mmol, 2.8 eq) was added in one portion. After 2 h, 0.1 mL of water was added, the mixture was diluted with 5 mL of water, 3.5 mL of aq. 2M $KHSO_4$ and 10 mL of EtOAc. After phase cut, the organic layer was washed with aq. 2M $KHSO_4$ and then with 2 mL of water. After concentration, the crude product was obtained with >99:1 dr and 85% solution yield. An analytically pure sample was obtained by purification by silica gel column chromatography. The column was preloaded with $CH_2Cl_2$ and then the crude product was loaded on the column with the help of $CH_2Cl_2$. The column was first washed with 0-100% EtOAc. After the fraction was collected and concentrated, the product was obtained as a foam solid.

$^1H$ NMR (500 MHz, DMSO-$d_6$) δ 11.20 (bs, 2H), 8.64 (s, 1H), 8.57 (s, 1H), 8.56 (s, 1H), 8.49 (s, 1H), 8.22 (d, J=6.5 Hz, 1H), 8.07-8.03 (m, 4H), 7.65-7.62 (m, 6H), 7.59-7.52 (m, 4H), 7.35-7.31 (m, 2H), 7.22-7.19 (m, 6H), 7.16-7.14 (m, 1H), 6.90 (s, 1H), 6.80-6.77 (m, 5H), 6.57 (t, J=6.80 Hz, 1H), 6.43 (t, J=6.90 Hz, 1H), 5.45 (m, 1H), 5.35 (bs, 1H), 4.63 (bs, 1H), 4.23 (s, 1H), 4.19 (s, 1H), 4.02 (m, 1H), 3.88-3.85 (m, 3H), 3.68 (bs, 6H), 3.33-3.29 (m, 2H), 3.24-3.19 (m, 2H), 2.70 (m, 1H), 2.56 (m, 1H), 2.41 (m, 1H), 1.62-1.57 (m, 2H), 1.49 (d, J=6.40 Hz, 3H), 1.06 (s, 9H), 0.84 (t, J=7.20 Hz, 3H). $^{13}C$ NMR (125 MHz, DMSO-$d_6$) δ 166.1, 166.0, 165.7, 161.2 [d, J(P, C)=5.69 Hz], 158.5, 158.5, 152.2, 152.2, 151.9, 151.8, 151.0, 150.9, 150.9, 145.1, 144.0, 143.5, 135.9, 135.8, 135.7, 133.8, 133.1, 133.0, 133.0, 132.9, 130.6, 130.1, 130.1, 129.0, 129.0, 128.9, 128.9, 128.5, 128.5, 128.2, 128.1, 127.1, 126.6, 126.4, 113.6, 109.8, 107.5, 86.2, 85.5 [d, J (P, C)=8.73 Hz], 84.5, 84.3, 84.3, 79.2 [d, J (P, C)=4.75 Hz], 78.6 [d, J (P, C)=5.15 Hz], 74.0, 69.6, 67.6 [d, J (P, C)=4.4 Hz], 63.5, 55.4, 55.4, 39.0, 36.4, 27.2, 22.2 [d, J (P, C)=4.98 Hz], 22.1, 19.1, 10.6. $^{31}P$ (202 MHz, DMSO-$d_6$) δ 65.64 Hz.

6.2. dA-dC

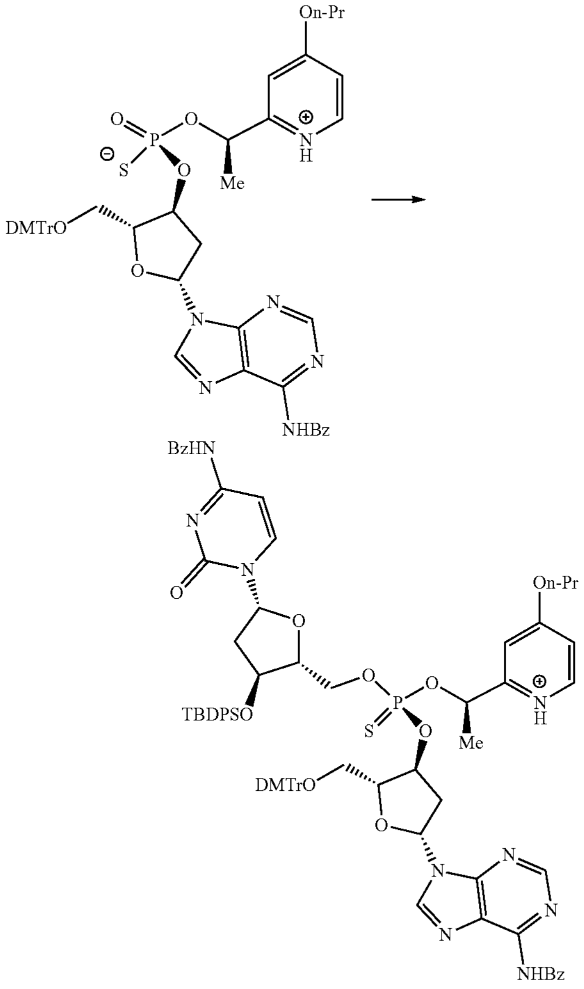

dA-dC

To a dry and clean flask was charged the nucleoside phosphorothioate dA-P(V) (1.4 g, 1.53 mmol) and dC (0.96 g, 1.68 mmol, 1.1 eq.) with TBDPS as the protection group. The mixture was dried by evaporation of 3 mL of pyridine. After 3 mL of pyridine was added, DMOCP (0.79 g, 4.3 mmol, 2.8 eq) was added in one portion. After 2 h, 0.1 mL of water was added, the mixture was diluted with 5 mL of water, 7 mL of aq. 2M $KHSO_4$ and 10 mL of EtOAc. After phase cut, the organic layer was washed with 8 mL of aq. 2M $KHSO_4$ and then with 2 mL of water. After concentration, the crude product was obtained with 97.5:2.5 dr and 78% solution yield. An analytically pure sample was obtained by purification by silica gel column chromatography. The column was preloaded with $CH_2Cl_2$ and then the crude product was loaded on the column with the help of $CH_2Cl_2$. The column was first washed with 0-100% EtOAc. After the fraction was collected and concentrated, the product was obtained as a foam solid.

$^1$H NMR (500 MHz, DMSO-$d_6$) δ 11.23 (bs, 2H), 8.58 (bs, 2H), 8.22 (d, J=5.65 Hz, 1H), 8.06 (d, J=7.50 Hz, 2H), 7.98 (d, J=7.50 Hz, 2H), 7.94 (d, J=7.25 Hz, 1H), 6.67-7.35 (m, 18H), 7.27-7.15 (m, 8H), 6.90 (d, J=2.25 Hz, 1H), 6.81-6.79 (m, 3H), 6.48 (t, J=6.95 Hz, 1H), 6.24 (t, J=6.70 Hz, 1H), 5.49 (m, 1H), 5.38 (m, 1H), 4.35 (m, 1H), 4.27 (m, 1H), 4.16 (m, 1H), 3.97 (m, 1H), 3.89-3.82 (m, 3H), 6.39 (s, 3H), 3.69 (s, 3H), 3.28-3.25 (m, 2H), 2.62 (m, 1H), 2.35 (m, 1H), 1.81 (m, 1H), 1.63 (m, 2H), 1.54 (d, J=6.5 Hz, 3H), 1.03 (s, 9H), 0.86 (t, J=7.35 Hz, 3H). $^{13}$C NMR (125 MHz, DMSO-$d_6$): δ 165.7, 163.6, 161.1 [d, J (P, C)=5.51 Hz], 158.5, 158.5, 154.7, 152.3, 151.8, 151.0, 150.9, 145.1, 144.5, 144.0, 135.8, 135.8, 133.8, 133.5, 133.2, 133.0, 133.0, 132.9, 130.6, 130.1, 130.1, 129.0, 128.9, 128.9, 128.5, 128.2, 128.1, 127.1, 126.5, 113.6, 109.7, 107.6, 96.7, 86.9, 85.7 [d, J (P, C)=8.80 Hz], 84.5, 84.3 [d, J (P, C)=6.41 Hz], 73.6, 69.6, 68.2, 67.5, 63.5, 55.4, 55.4, 41.0, 36.5, 27.1, 22.4 [d, J (P, C)=5.08 Hz], 21.2, 19.1, 10.6. $^{31}$P NMR (202 MHz, DMSO-$d_6$): δ 65.86.

6.3. dA-dG

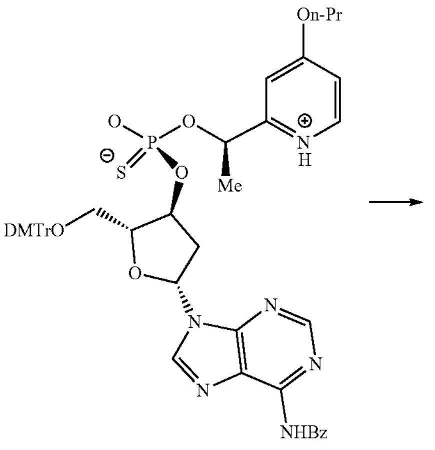

-continued

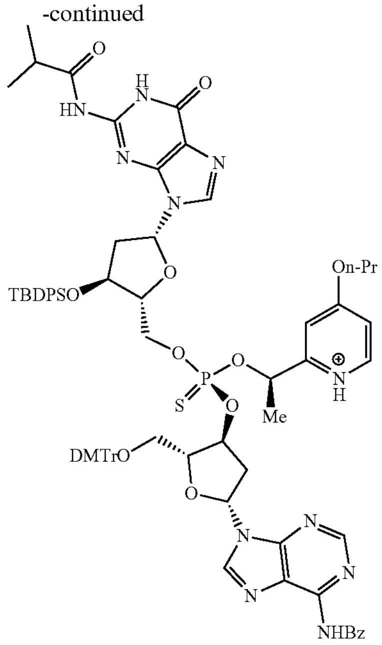

dA-dG

To a dry and clean flask was charged the nucleoside phosphorothioate dA-P(V) (1.4 g, 1.53 mmol) and dG (0.967 g, 1.68 mmol, 1.1 eq.) with TBDPS as the protection group. The mixture was dried by evaporation of 3 mL of pyridine. After 3 mL of pyridine was added, DMOCP (0.79 g, 4.3 mmol, 2.8 eq) was added in one portion. After 2 h, 0.1 mL of water was added, the mixture was diluted with 5 mL of water, 7 mL of aq. 2M $KHSO_4$ and 10 mL of EtOAc. After phase cut, the organic layer was washed with 8 mL of aq. 2M $KHSO_4$ and then 2 mL of water. After concentration, the crude product was obtained with 96.3:3.7 dr and 75% solution yield. An analytically pure sample was obtained by purification on silica gel column. The column was preloaded with $CH_2Cl_2$ and then the crude product was loaded on the column with the help of $CH_2Cl_2$. The column was eluted with 0-100% EtOAc. After the fraction was collected and concentrated, the product was obtained as a foam solid.

$^1$H NMR (500 MHz, DMSO-$d_6$) δ 12.08 (s, 1H), 11.56 (s, 1H), 11.20 (s, 1H), 8.57 (s, 1H), 8.56 (s, 1H), 8.21 (d, J=5.45 Hz, 1H), 8.05 (d, J=7.50 Hz, 2H), 8.01 (s, 1H), 7.66-7.53 (m, 7H), 7.48-7.41 (m, 6H), 7.33 (d, J=7.55 Hz, 2H), 7.21-7.14 (m, 7H), 6.88 (s, 1H), 6.80-6.77 (m, 5H), 6.45 (t, J=6.65 Hz, 1H), 6.33 (t, J=6.60 Hz, 1H), 5.44 (m, 1H), 5.34 (m, 1H), 4.39 (bs, 1H), 4.24 (bs, 1H), 4.13 (bs, 1H), 3.87-3.80 (m, 4H), 3.69 (s, 6H), 3.29 (m, 1H), 3.23-3.16 (m, 2H0, 2.76 (m, 1H), 2.56 (m, 1H), 2.47 (m, 1H), 2.33 (m, 1H), 1.64-1.60 (m, 2H), 1.51 (d, J=6.2 Hz, 3H), 1.17 (d, J=7.45 Hz, 3H), 1.16 (d, J=7.45 Hz, 3H), 1.03 (s, 9H), 0.86 (t, J=7.30 Hz, 3H). $^{13}$C NMR (125 MHz, DMSO-$d_6$): δ 180.0, 165.5, 165.2, 160.6 [d, J (P, C)=5.6 Hz)], 158.0, 158.0, 154.7, 151.7, 151.3, 150.5, 150.4, 148.4, 148.1, 144.6, 143.6, 136.9, 135.3, 135.2, 135.2, 133.3, 132.4, 132.4, 132.3, 130.1, 129.6, 129.6, 128.4, 128.4, 128.0, 128.0, 127.7, 127.6, 126.6, 126.1, 120.3, 85.7, 85.2 [d, J (P, C)=8.4 Hz)], 84.1, 83.8 [d, J (P, C)=6.15 Hz)], 83.2, 73.7, 69.1, 67.2, 54.9, 54.9, 35.7, 34.7, 26.7, 21.8 [d, J (P, C)=5.2 Hz)], 21.6, 18.8, 18.7, 18.5, 10.0. $^{31}$P NMR (202 MHz, DMSO-$d_6$): δ 65.66.

6.4. dAdT

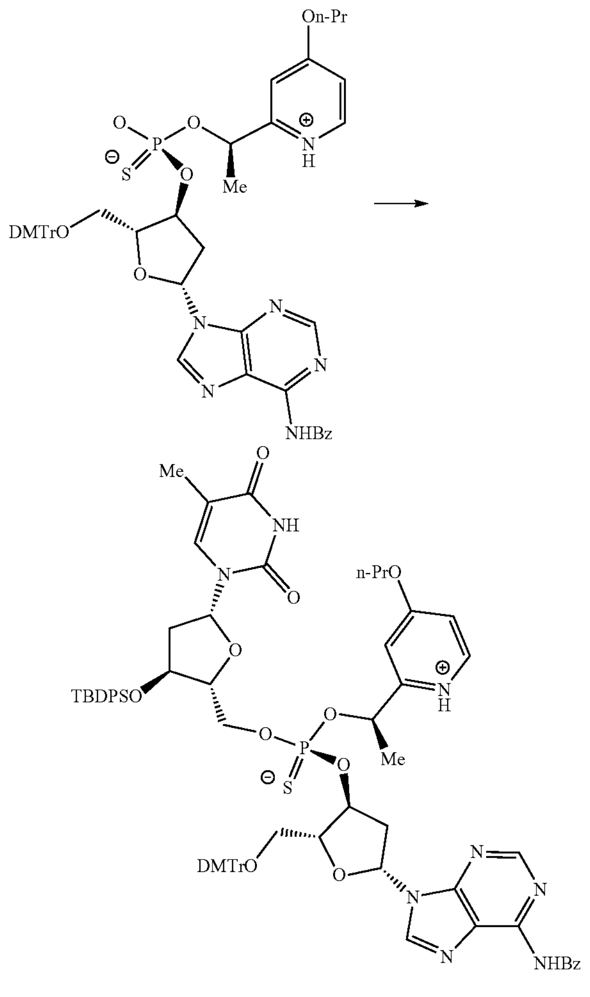

dA-dT

To a dry and clean flask was charged the nucleoside phosphorothioate dA-P(V) (1.4 g, 1.53 mmol) and dT (0.81 g, 1.68 mmol, 1.1 eq.) with TBDPS as the protection group. The mixture was dried by evaporation of 3 mL of pyridine. After 3 mL of pyridine was added, DMOCP (0.79 g, 4.3 mmol, 2.8 eq) was added in one portion. After 2 h, 0.1 mL of water was added, the mixture was diluted with 5 mL of water, 7 mL of aq. 2M $KHSO_4$ and 10 mL of EtOAc. After phase cut, the organic layer was washed with 8 mL of aq. 2M $KHSO_4$ and then 2 mL of water. After concentration, the crude product was obtained with >98.2:2.2 dr and 84% solution yield. An analytically pure sample was obtained by purification on silica gel column. The column was preloaded with $CH_2Cl_2$ and then the crude product was loaded on the column with the help of $CH_2Cl_2$. The column was eluted with 0-100% EtOAc. After the fraction was collected and concentrated, the product was obtained as a foam solid.

$^{1}$H NMR (500 MHz, DMSO-$d_6$) δ 11.33 (bs, 1H), 11.21 (bs, 1H), 8.60 (s, 1H), 8.58 (s, 1H), 8.22 (d, J=5.70 Hz, 1H), 8.06 (d, J=7.55 Hz, 2H), 7.65 (t, J=7.45 Hz, 1H), 7.59-7.54 (m, 6H), 7.47-7.39 (m, 6H), 7.35 (d, J=7.50 Hz, 2H), 7.23-7.15 (m, 8H), 6.87 (d, J=2.1 Hz, 1H), 6.82-6.78 (m, 5H), 6.45 (t, J=6.90 Hz, 1H), 6.27 (t, J=5.90 Hz, 1H), 4.28 (m, 1H), 4.19 (m, 1H), 4.01 (m, 1H), 3.89 (t, J=6.5 Hz, 2H), 3.84 (m, 1H), 3.74 (m, 1H), 3.70 (s, 3H), 3.70 (s, 3H), 3.33-3.30 (m, 1H), 3.27-3.21 (m, 2H), 2.60 (m, 1H), 2.03 (m, 1H), 1.78 (m, 1H), 1.68-1.62 (m, 2H), 1.66 (s, 1H), 1.54 (d, J=6.5 Hz, 3H), 1.02 (s, 9H), 0.90 (t, J=7.35 Hz, 3H). $^{13}$C NMR (125 MHz, DMSO-$d_6$) δ 166.1, 165.7, 164.0, 161.1 [d, J (P, C)=5.55 Hz], 152.3, 151.9, 151.0, 150.9, 150.8, 145.1, 144.0, 135.8, 135.8, 135.7, 135.7, 135.5, 133.8, 133.0, 132.9, 130.6, 130.6, 130.1, 130.1, 129.0, 129.0, 128.5, 128.5, 128.2, 128.1, 127.1, 126.6, 113.6, 110.4, 109.6, 107.6, 86.2, 85.1 [d, J (P, C)=8.63 Hz], 84.5, 84.4, 84.3 [d, J (P, C)=6.25 Hz], 79.2 [d, J (P, C)=4.54 Hz], 78.7 [d, J (P, C)=4.56 Hz], 73.8, 69.6, 67.8 [d, J (P, C)=5.99 Hz], 63.4, 36.5, 27.1, 22.3 [d, J (P, C)=5.19 Hz], 22.1, 19.0, 12.6, 10.6. $^{31}$P NMR (202 MHz, DMSO-$d_6$): δ 65.88.

6.5. dA-dT No TBDPS

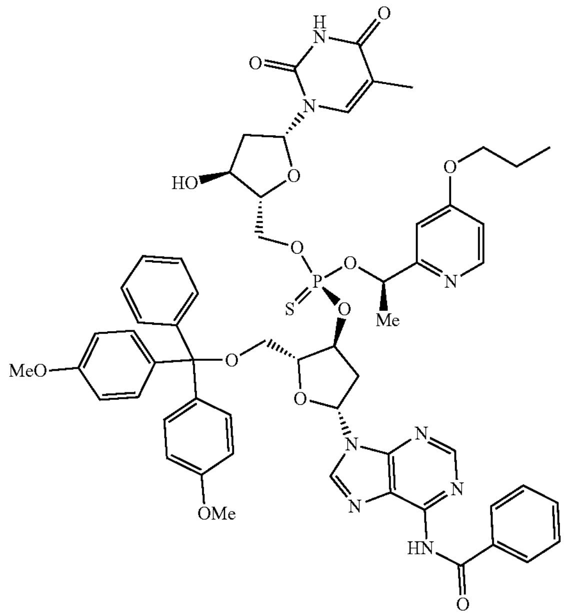

dA-dT no TBDPS

To a clean flask was charged dA-dT (0.5 g, 0.36 mmol) and THF (5 mL). 1M TBAF in THF (0.73 mL, 0.725 mmol) was added at 20-25° C. After 0.5 h, the mixture was diluted with EtOAc and then washed with water. After concentration, the crude product was purified by column chromatography on silica gel with 0-10% MeOH in $CH_2Cl_2$ to give 0.41 g of the product as a foam solid with quantitative yield.

$^{1}$H NMR (500 MHz, DMSO-$d_6$) δ 11.33 (bs, 1H), 11.22 (bs, 1H), 8.60 (bs, 2H), 8.32 (d, J=5.7 Hz, 1H), 8.06 (d, J=7.5 Hz, 2H), 7.65 (t, J=7.3 Hz, 1H), 7.56 (t, J=7.7 Hz, 2H), 7.39-7.36 (m, 3H), 7.26-7.24 (m, 6H), 7.19 (m, 1H), 6.97 (d, J=2.55 Hz, 1H), 6.88 (m, 1H), 6.85-6.81 (m, 4H), 6.52 (t, J=13.85 Hz, 1H), 6.20 (m, 1H), 5.60 (m, 1H), 5.45-5.44 (m, 2H), 4.37 (m, 1H), 4.22-4.16 (m, 3H), 3.96-3.94 (m, 3H), 3.72 (s, 1H), 3.72 (s, 1H), 3.39-3.28 (m, 2H), 2.71 (m, 1H), 2.05 (m, 1H), 1.95 (m, 1H), 1.71-1.65 (m, 5H), 1.60 (d, J=6.5 Hz, 3H), 0.92 (t, J=7.35 Hz, 3H). $^{13}$C NMR (125 MHz, DMSO-$d_6$) δ 166.1, 165.8, 164.1, 161.2 [d, J (P, C)=5.7 Hz], 158.6, 158.6, 152.2, 151.9, 151.0, 150.9, 150.8, 145.1, 144.0, 135.9, 135.8, 135.8, 133.8, 132.9, 130.2, 130.1, 128.9, 128.9, 128.2, 128.1, 127.2, 126.6, 113.6, 110.3, 109.8, 107.6, 86.3, 84.7 [d, J (P, C)=8.7 Hz], 84.5, 84.4, 84.3 [d, J (P, C)=6.4 Hz], 79.3 [d, J (P, C)=4.9 Hz], 78.7 [d, J (P, C)=4.75 Hz], 70.8, 69.6, 68.5 [d, J (P, C)=5.5 Hz], 63.6, 55.5, 55.4, 39.4, 36.5, 22.4 [d, J (P, C)=5.03 Hz], 22.1, 12.6, 10.6. $^{31}P$ NMR (202 MHz, DMSO-$d_6$): δ 65.91.

6.6. dC-dC

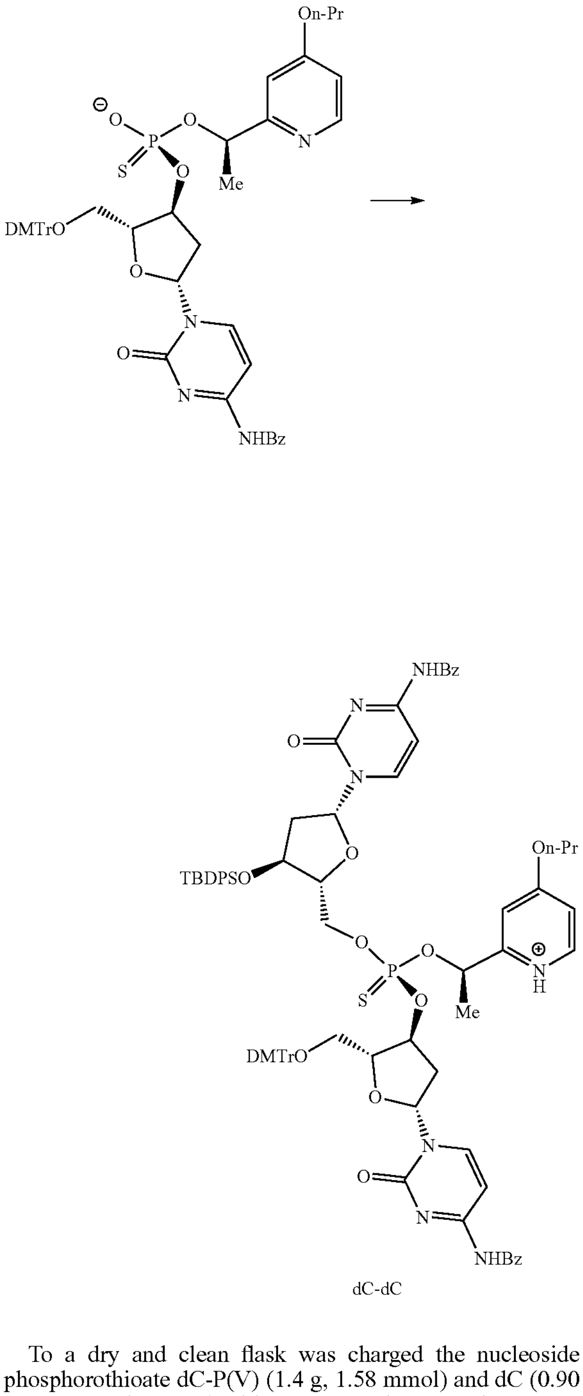

dC-dC

To a dry and clean flask was charged the nucleoside phosphorothioate dC-P(V) (1.4 g, 1.58 mmol) and dC (0.90 g, 1.58 mmol, 1.0 eq.) with TBDPS as the protection group. The mixture was dried by evaporation of 3 mL of pyridine. After 3 mL of pyridine was added, DMOCP (0.82 g, 4.6 mmol, 2.8 eq) was added in one portion. After 2 h, 0.1 mL of water was added, the mixture was diluted with 5 mL of water, 7 mL of aq. 2M $KHSO_4$ and 10 mL of EtOAc. After phase cut, the organic layer was washed with 8 mL of aq. 2M $KHSO_4$ and then 2 mL of water. After concentration, the crude product was obtained with 98.5:1.5 dr and 82% solution yield. An analytically pure sample was obtained by purification on silica gel column. The column was preloaded with $CH_2Cl_2$ and then the crude product was loaded on the column with the help of $CH_2Cl_2$. The column was eluted with 0-100% EtOAc. After the fraction was collected and concentrated, the product was obtained as a foam solid.

$^1H$ NMR (500 MHz, DMSO-$d_6$) δ 11.28 (s, 1H), 11.24 (s, 1H), 8.22 (d, J=5.60 Hz, 1H), 8.14 (d, J=7.05 Hz, 1H), 8.02-7.99 (m, 4H), 7.90 (d, J=7.15 Hz, 1H), 7.64-7.57 (m, 6H), 7.54-7.36 (m, 13H), 7.30-7.19 (m, 9H), 6.89-6.85 (m, 5H), 6.80 (d, J=5.50 Hz, 1H), 6.22 (t, J=6.50 Hz, 1H), 6.14 (t, J=6.35 Hz, 1H), 5.45 (m, 1H), 5.11 (bs, 1H), 4.33 (s, 1H), 4.25 (s, 1H), 4.13 (s, 1H), 3.93-3.85 (m, 3H), 3.84 (m, 1H), 3.71 (s, 6H), 2.65 (m, 1H), 2.38-2.33 (m, 2H), 1.81 (m, 1H), 1.67-1.59 (m, 2H), 1.52 (d, J=6.40 Hz, 3H), 1.02 (s, 9H), 0.87 (t, J=7.35 Hz, 3H). $^{13}C$ NMR (125 MHz, DMSO-$d_6$) δ 167.7, 167.6, 165.7, 163.7, 163.6, 161.1 [d, J (P, C)=5.61 Hz], 158.7, 158.6, 154.7, 154.6, 150.9, 145.0, 144.8, 144.6, 135.7, 135.6, 135.5, 133.6, 133.5, 133.2, 133.0, 132.9, 130.6, 130.2, 130.1, 128.9, 128.9, 128.5, 128.3, 128.2, 127.3, 113.7, 109.8, 107.6, 96.7, 96.6, 87.1, 87.0, 86.7, 85.7 [d, J (P, C)=7.53 Hz], 84.7 [d, J (P, C)=7.03 Hz], 78.8 [d, J (P, C)=4.86 Hz], 78.7, 73.6, 69.6, 67.5[d, J (P, C) 4.39 Hz], 63.1, 55.4, 41.0, 39.3, 27.1, 22.3 [d, J (P, C)=5.30 Hz], 22.1, 19.0, 10.6. $^{31}P$ NMR (202 MHz, DMSO-$d_6$) δ 65.76 Hz.

6.7. dC-dG

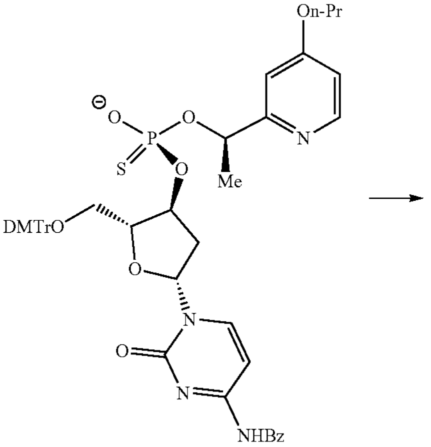

-continued

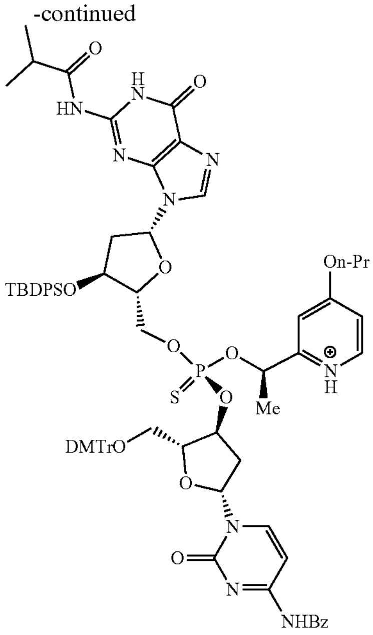

dC-dG

To a dry and clean flask was charged the nucleoside phosphorothioate dC-P(V) (1.4 g, 1.57 mmol) and dG (0.993 g, 1.73 mmol, 1.1 eq.) with TBDPS as the protection group. The mixture was dried by evaporation of 3 mL of pyridine. After 3 mL of pyridine was added, DMOCP (0.81 g, 4.4 mmol, 2.8 eq) was added in one portion. After 2 h, 0.1 mL of water was added, the mixture was diluted with 5 mL of water, 7 mL of aq. 2M $KHSO_4$ and 10 mL of EtOAc. After phase cut, the organic layer was washed with 8 mL of aq. 2M $KHSO_4$ and then 2 mL of water. After concentration, the crude product was obtained with 99:1 dr and 83% solution yield. An analytically pure sample was obtained by purification on silica gel column. The column was preloaded with $CH_2Cl_2$ and then the crude product was loaded on the column with the help of $CH_2Cl_2$. The column was eluted with 0-100% EtOAc. After the fraction was collected and concentrated, the product was obtained as a foam solid.

$^1$H NMR (500 MHz, DMSO-$d_6$) δ 12.07 (s, 1H), 11.55 (s, 1H), 11.29 (s, 1H), 8.22 (d, J=5.50 Hz, 1H), 8.12 (d, J=6.70 Hz, 1H), 8.01 (d, J=7.60 Hz, 2H), 7.98 (s, 1H), 7.63-7.57 (m, 5H), 7.52-7.50 (m, 2H), 7.48-7.41 (m, 6H), 7.35-7.33 (m, 2H), 7.29-7.26 (m, 2H), 7.22-7.18 (m, 6H), 6.86-6.85 (m, 5H), 6.80 (d, J=5.50 Hz, 1H), 6.31 (t, J=6.65 Hz, 1H), 6.10 (t, J=6.15 Hz, 1H), 5.40 (m, 1H), 5.08 (m, 1H), 4.38 (bs, 1H), 4.20 (bs, 1H), 4.14-4.10 (m, 1H), 3.89-3.78 (m, 4H), 3.70 (s, 6H), 3.27 (bs, 2H), 2.76 (m, 1H), 2.60 (m, 1H), 2.32-2.30 (m, 2H), 1.66-1.60 (m, 2H), 1.49 (d, J=6.2 Hz, 3H), 1.12 (d, J=6.75 Hz, 3H), 1.11 (d, J=6.75 Hz, 3H), 1.03 (s, 9H), 0.87 (t, J=7.30 Hz, 3H). $^{13}$C NMR (125 MHz, DMSO-$d_6$): δ 180.0, 167.2, 165.2, 163.2, 160.6 [d, J (P, C)=5.78 Hz)], 158.1, 158.1, 154.7, 154.1, 150.4, 148.4, 148.1, 144.4, 144.2, 137.0, 135.2, 135.1, 134.9, 133.0, 132.7, 132.5, 132.3, 130.1, 129.7, 129.6, 128.4, 128.0, 127.8, 127.6, 126.7, 120.3, 113.2, 109.3, 107.0, 96.1, 86.5, 86.2, 85.1 [d, J (P, C)=8.56 Hz)], 84.2 [d, J (P, C)=4.86 Hz)], 83.1, 78.1 [d, J (P, C)=4.58 Hz)], 78.0 [d, J (P, C)=4.94 Hz)], 73.7, 69.1, 67.1 [d, J (P, C)=4.65 Hz)], 62.4, 54.0, 39.0, 38.8, 34.7, 26.6, 21.7 [d, J (P, C)=4.95 Hz)], 21.6, 18.8, 18.8, 18.5, 10.1. $^{31}$P NMR (202 MHz, DMSO-$d_6$): δ 65.63.

6.8. dC-dG no DMTr

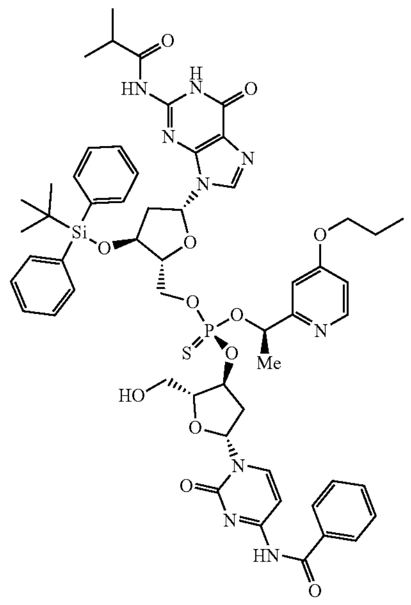

dC-dG no DMTr

To a clean flask was charged dC-dG (1.0 g, 0.689 mmol) and $CH_2Cl_2$ (10 mL). Dichloroacetic acid (0.57 mL, 6.893 mmol) was added in one portion. After the mixture was stirred for 0.5 h at 20-23° C., the reaction was complete and quenched with aq. $NaHCO_3$. The product was extracted with EtOAc and then washed with water. The crude product was purified on silica gel column with 0-10% MeOH in $CH_2Cl_2$ to give 0.75 g of the pure product with 94% yield.

$^1$H NMR (500 MHz, DMSO-$d_6$) δ 12.09 (bs, 1H), 11.57 (s, 1H), 11.27 (s, 1H), 8.33 (d, J=8.50 Hz, 1H), 8.26 (d, J=5.70 Hz, 1H), 8.04 (s, 1H), 8.03 (d, J=7.25 Hz, 2H), 7.64-7.60 (m, 5H), 7.53-7.48 (m, 8H), 7.40 (m, 1H), 6.90 (d, J=2.25 Hz, 1H), 6.82 (dd, J=2.4, 5.7 Hz, 1H), 6.33 (m, 1H), 6.15 (m, 1H), 5.44 (m, 1H), 5.26 (bs, 1H), 5.06 (m, 1H), 4.44 (m, 1H), 4.17 (m, 1H), 4.13 (m, 1H), 3.97-3.90 (m, 3H), 3.89-3.83 (m, 1H), 3.64-3.57 (m, 2H), 2.79 (m, 1H), 2.60-2.54 (m, 2H), 2.34 (m, 1H), 2.22 (m, 1H), 1.69-1.64 (m, 2H), 1.55 (d, J=6.5 Hz, 3H), 1.14 (d, J=2.0 Hz, 3H), 1.12 (d, J=2.0 Hz, 3H), 1.05 (s, 9H), 0.90 (t, J=7.35 Hz, 3H). $^{13}$C NMR (125 MHz, DMSO-$d_6$): δ 180.5, 167.8, 165.7, 163.7, 161.1 [d, J (P, C)=6.06 Hz)], 155.2, 154.8, 150.8, 149.0, 148.6, 145.2, 137.6, 135.7, 133.2, 133.0, 132.8, 130.7, 130.6, 128.9, 128.9, 128.5, 128.5, 120.9, 109.9, 107.5, 96.7, 86.8, 86.5 [d, J (P, C)=5.44 Hz)], 85.7 [d, J (P, C)=8.66 Hz)], 83.7, 79.6 [d, J (P, C)=4.96 Hz)], 78.5 [d, J (P, C)=4.93 Hz)], 74.1, 69.6, 67.6 [d, J (P, C)=4.85 Hz)], 61.2, 39.5, 39.2, 35.3, 27.2, 22.2 [d, J (P, C)=4.8 Hz)], 22.1, 19.3, 19.3, 19.1, 10.6. $^{31}$P NMR (202 MHz, DMSO-$d_6$): δ 65.49.

6.9. dC-dT

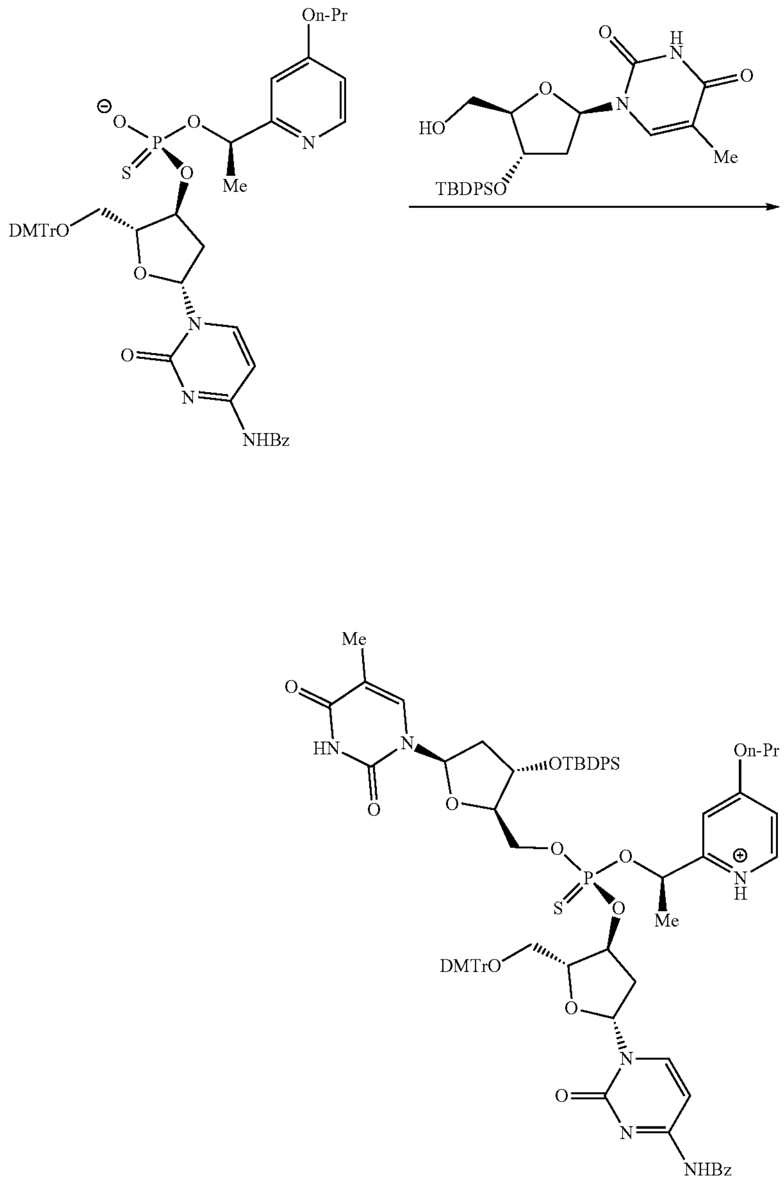

dC-dT

To a dry and clean flask was charged the nucleoside phosphorothioate dC-P(V) (1.4 g, 1.58 mmol) and dT (0.76 g, 1.58 mmol, 1.0 eq.) with TBDPS as the protection group. The mixture was dried by evaporation of 3 mL of pyridine. After 3 mL of pyridine was added, DMOCP (0.82 g, 4.6 mmol, 2.8 eq) was added in one portion. After 2 h, 0.1 mL of water was added, the mixture was diluted with 5 mL of water, 7 mL of aq. 2M $KHSO_4$ and 10 mL of EtOAc. After phase cut, the organic layer was washed with 8 mL of aq. 2M $KHSO_4$ and then 2 mL of water. After concentration, the crude product was obtained with 98.5:1.5 dr and 85% solution yield. An analytically pure sample was obtained by purification on silica gel column. The column was preloaded with $CH_2Cl_2$ and then the crude product was loaded on the column with the help of $CH_2Cl_2$. The column was eluted with 0-100% EtOAc. After the fraction was collected and concentrated, the product was obtained as a foam solid.

$^1$H NMR (500 MHz, DMSO-$d_6$) δ 11.32 (s, 1H), 11.30 (s, 1H), 8.22 (d, J=5.55 Hz, 1H), 8.14 (d, J=7.05 Hz, 1H), 8.02 (d, J=7.60 Hz, 2H), 7.63 (t, J=7.30 Hz, 1H), 7.59-7.51 (m, 6H), 7.48-7.36 (m, 8H), 7.30 (t, J=7.35 Hz, 2H), 7.25-7.21 (m, 7H), 6.88-6.85 (m, 5H), 6.81 (d, J=5.45 Hz, 1H), 6.25 (t, J=6.70 Hz, 1H), 6.12 (t, J=6.20 Hz, 1H), 5.44 (m, 1H), 5.11 (bs, 1H), 4.24 (bs, 1H), 4.16 (bs, 1H), 3.98 (bs, 1H), 3.89 (t, J=6.25 Hz, 2H), 3.77 (m, 1H), 3.72 (s, 6H), 3.69 (m, 1H), 3.30 (bs, 2H), 2.63 (m, 1H), 2.38 (m, 1H), 2.04-2.00 (m, 1H), 1.78-1.73 (m, 1H), 1.69-1.64 (m, 1H), 1.66 (s, 3H), 1.52 (d, J=6.25 Hz, 3H), 1.01 (s, 9H), 0.91 (t, J=7.30 Hz, 3H). $^{13}$C NMR (125 MHz, DMSO-$d_6$) δ 167.8, 165.7, 164.0, 163.7, 161.0 [d, J (P, C)=5.45 Hz], 158.7, 158.7, 154.7, 150.9, 150.8, 145.0, 144.8, 135.7, 135.7, 135.6, 135.5, 133.5, 133.2, 133.0, 132.9, 130.6, 130.6, 130.2, 130.2, 128.9, 128.4, 128.4, 128.2, 127.3, 113.7, 110.4, 110.0, 107.6, 96.6, 87.0, 86.7, 85.0 [d, J (P, C)=8.67 Hz], 84.5, 78.7 [d, J (P, C)=4.66 Hz], 78.5 [d, J (P, C)=4.46 Hz], 73.8, 69.6, 67.8 [d, J (P, C)=7.08 Hz], 62.9, 55.5, 39.3, 27.1, 22.3 [d, J (P, C)=5.15 Hz], 19.0, 12.5, 10.6. $^{31}$P NMR (202 MHz, DMSO-$d_6$) δ 65.85 Hz.

6.10. dG-dG

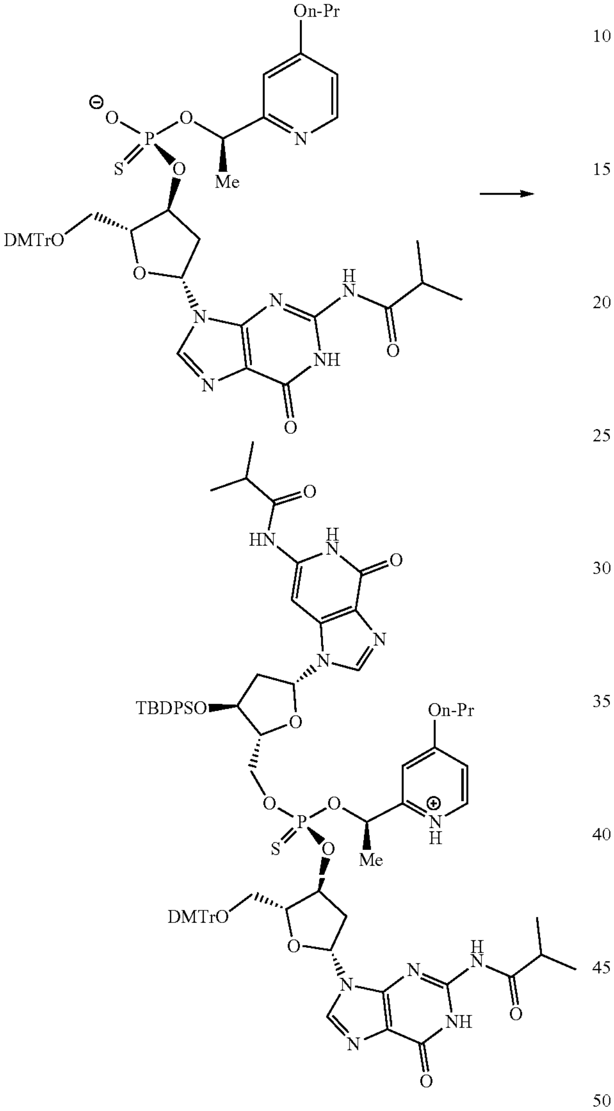

dG-dG

To a dry and clean flask was charged the nucleoside phosphorothioate dG-P(V) (1.4 g, 1.56 mmol) and dG (0.99 g, 1.71 mmol, 1.1 eq.) with TBDPS as the protection group. The mixture was dried by evaporation of 3 mL of pyridine. After 3 mL of pyridine was added, DMOCP (0.81 g, 4.4 mmol, 2.8 eq) was added in one portion. After 2 h, 0.1 mL of water was added, the mixture was diluted with 5 mL of water, 7 mL of aq. 2M $KHSO_4$ and 10 mL of EtOAc. After phase cut, the organic layer was washed with 8 mL of aq. 2M $KHSO_4$ and then 2 mL of water. After concentration, the crude product was obtained with 97.1:2.9 dr and 79% solution yield. An analytically pure sample was obtained by purification on silica gel column. The column was preloaded with $CH_2Cl_2$ and then the crude product was loaded on the column with the help of $CH_2Cl_2$. The column was eluted with 0-100% EtOAc. After the fraction was collected and concentrated, the product was obtained as a foam solid.

$^1$H NMR (500 MHz, DMSO-$d_6$) δ 12.07 (bs, 2H), 11.57 (s, 1H), 11.56 (s, 1H), 8.18 (d, J=5.55 Hz, 1H), 1H), 8.08 (s, 1H), 7.96 (s, 1H), 7.63-7.57 (m, 4H), 7.48-7.39 (m, 6H), 7.31-7.30 (m, 2H), 7.26-7.16 (m, 7H), 6.84 (s, 1H), 6.80-6.76 (m, 5H), 6.31 (t, J=6.65 Hz, 1H), 6.15 (t, J=6.60 Hz, 1H), 5.39 (m, 1H), 5.15 (bs, 1H), 4.33 (bs, 1H), 4.10-4.09 (m, 2H), 3.89-3.85 (m, 3H), 3.75-3.74 (m, 1H), 3.69 (s, 6H), 3.22 (m, 1H), 3.14 (m, 1h), 2.98 (m, 1H), 2.76-2.73 (m, 2H), 2.41 (m, 1H), 2.32 (m, 1H), 1.64-1.59 (m, 2H), 1.48 (d, J=6.25 Hz, 3H), 1.12-1.11 (m, 12H), 1.02 (s, 9H), 0.86 (t, J=7.30 Hz, 3H). $^{13}$C NMR (125 MHz, DMSO-$d_6$): δ 180.0, 180.0, 165.2, 160.4 [d, J (P, C)=5.29 Hz)], 158.0, 158.0, 154.7, 154.7, 150.4, 148.6, 148.4, 148.1, 148.1, 144.5, 137.1, 136.8, 135.2, 135.2, 132.4, 132.3, 130.2, 129.6, 129.6, 127.9, 127.7, 127.6, 126.6, 120.5, 120.2, 113.0, 113.0, 109.2, 107.3, 85.8, 85.2 [d, J (P, C)=8.83 Hz)], 83.9 [d, J (P, C)=5.95 Hz)], 83.1, 82.8, 78.9 [d, J (P, C)=4.66 Hz)], 78.0 [d, J (P, C)=5.03 Hz)], 73.6, 69.1, 67.3, 63.3, 54.9, 54.9, 36.3, 34.7, 34.7, 26.6, 21.8 [d, J (P, C)=5.30 Hz)], 21.6, 18.8, 18.5, 10.0. $^{31}$P NMR (202 MHz, DMSO-$d_6$): δ 65.74.

6.11. dG-dT

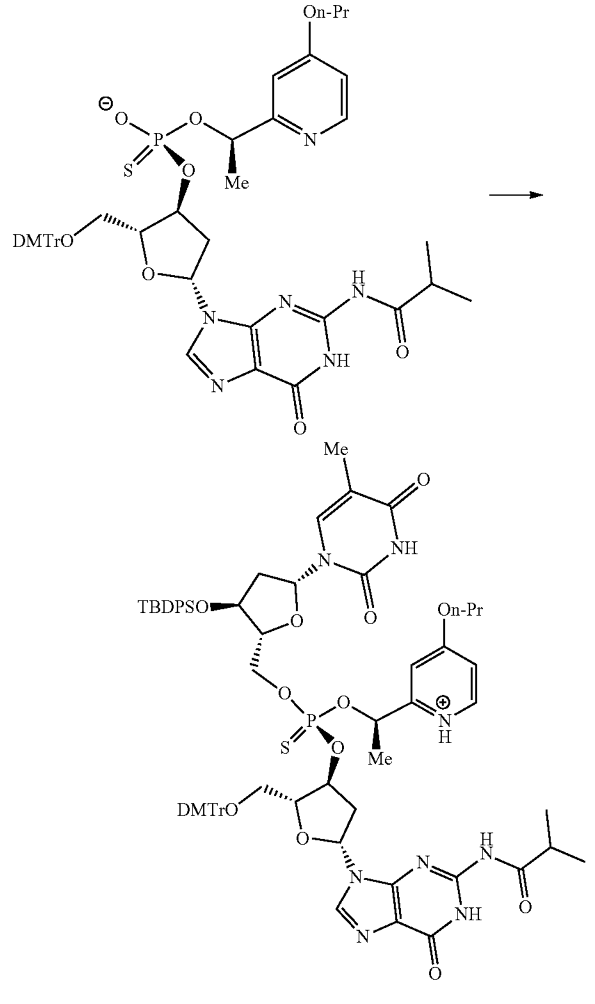

dG-dT

To a dry and clean flask was charged the nucleoside phosphorothioate dG-P(V) (1.4 g, 1.56 mmol) and dT (0.82 g, 1.71 mmol, 1.1 eq.) with TBDPS as the protection group. The mixture was dried by evaporation of 3 mL of pyridine. After 3 mL of pyridine was added, DMOCP (0.81 g, 4.4 mmol, 2.8 eq) was added in one portion. After 2 h, 0.1 mL of water was added, the mixture was diluted with 5 mL of water, 7 mL of aq. 2M $KHSO_4$ and 10 mL of EtOAc. After phase cut, the organic layer was washed with 8 mL of aq. 2M $KHSO_4$ and then 2 mL of water. After concentration, the crude product was obtained with 98.2:1.8 dr and 86% solution yield. An analytically pure sample was obtained by purification on silica gel column. The column was preloaded with $CH_2Cl_2$ and then the crude product was loaded on the column with the help of $CH_2Cl_2$. The column was eluted with 0-100% EtOAc. After the fraction was collected and concentrated, the product was obtained as a foam solid.

$^1$H NMR (500 MHz, DMSO-$d_6$) δ 12.08 (s, 1H), 11.54 (s, 1H), 11.34 (s, 1H), 8.21 (d, J=5.45 Hz, 1H), 8.10 (s, 1H), 7.58-7.55 (m, 4H), 7.46-7.37 (m, 6H), 7.33-7.31 (m, 2H), 7.24-7.18 (m, 8H), 6.84 (s, 1H), 6.80-6.77 (m, 5H), 6.25 (t, J=6.75 Hz, 1H), 6.19 (t, J=6.65 Hz, 1H), 5.45 (m, 1H), 5.19 (bs, 1H), 4.24 (bs, 1H), 4.10 (bs, 1H), 3.98 (bs, 1H), 3.87 (t, J=6.30 Hz, 2H), 3.80 (m, 1H), 3.70 (bs, 7H), 3.25-3.18 (m, 2H), 3.03 (m, 1H), 2.78 (m, 1H), 2.54 (m, 1H), 2.05 (m, 1H), 1.77 (m, 1H), 1.66-1.62 (m, 5H), 1.51 (d, J=6.20 Hz, 3H), 1.12 (d, J=6.60 Hz, 6H), 1.00 (s, 9H), 0.89 (t, J=7.30 Hz, 3H). $^{13}$C NMR (125 MHz, DMSO-$d_6$): δ 180.0, 165.2, 163.5, 160.4 [d, J (P, C)=5.49 Hz)], 158.1, 158.0, 154.7, 150.4, 150.3, 148.6, 148.1, 144.5, 137.1, 135.2, 135.2, 135.1, 132.4, 130.1, 129.7, 129.6, 128.0, 127.7, 127.6, 126.7, 120.5, 113.0, 113.0, 109.9, 109.1, 107.3, 85.8, 84.5 [d, J (P, C)=9.09 Hz)], 84.1, 84.0 [d, J (P, C)=6.05 Hz)], 82.8, 78.8 [d, J (P, C)=5.04 Hz)], 78.2 [d, J (P, C)=4.69 Hz)], 73.2, 69.1, 67.4, 63.2, 54.9, 54.9, 36.5, 34.8, 26.6, 21.8 [d, J (P, C)=5.15 Hz)], 21.6, 18.8, 18.8, 18.5, 12.0, 10.0. $^{31}$P NMR (202 MHz, DMSO-$d_6$): δ 66.00.

6.12. dT-dT

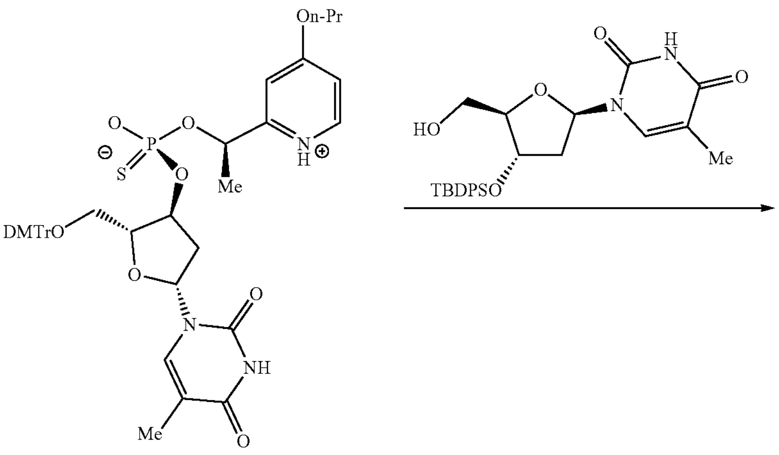

dT-P(V)

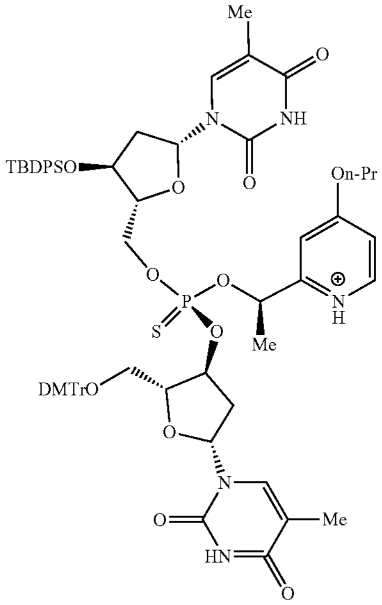

dT-dT

To a dry and clean flask was charged the nucleoside phosphorothioate dT-P(V) (1.5 g, 1.87 mmol) and dT (0.90 g, 1.87 mmol, 1.0 eq.) with TBDPS as the protection group. The mixture was dried by evaporation of 3 mL of pyridine. After 3 mL of pyridine was added, DMOCP (0.96 g, 5.23 mmol, 2.8 eq) was added in one portion. After 2 h, 0.1 mL of water was added, the mixture was diluted with 5 mL of water, 7 mL of aq. 2M $KHSO_4$ and 10 mL of EtOAc. After phase cut, the organic layer was washed with 8 mL of aq. 2M $KHSO_4$ and then 2 mL of water. After concentration, the crude product was obtained with 98.1:1.9 dr and 88% solution yield. An analytically pure sample was obtained by purification on silica gel column. The column was preloaded with $CH_2Cl_2$ and then the crude product was loaded on the column with the help of $CH_2Cl_2$. The column was eluted with 0-100% EtOAc. After the fraction was collected and concentrated, the product was obtained as a foam solid.

$^1$H NMR (500 MHz, DMSO-$d_6$) δ 11.4 (bs, 1H), 11.31 (bs, 1H), 8.21 (d, J=5.50 Hz, 1H), 7.57-7.54 (m, 4H), 7.48 (s, 1H), 7.45-7.36 (m, 8H), 7.29 (t, J=7.40 Hz, 2H), 7.28-7.19 (m, 6H), 6.88-6.80 (m, 5H), 6.81 (d, J=5.35 Hz, 1H), 6.23 (t, J=7.20 Hz, 1H), 6.18 (t, J=6.85 Hz, 1H), 5.43 (m, 1H), 5.19 (bs, 1H), 4.22 (m, 1H), 4.03 (m, 1H), 3.96 (bs, 1H), 3.89 (t, J=6.30 Hz, 2H), 3.77 (m, 1H), 3.66 (m, 1H), 3.25-3.18 (m, 2H), 2.46 (m, 1H), 2.36 (m, 1H), 2.02-1.98 (m, 1H), 1.77-1.71 (m, 1H), 1.68-1.64 (m, 5H), 1.51 (d, J=6.30 Hz, 3H), 1.46 (s, 3H), 1.00 (s, 9H), 0.90 (t, J=7.30 Hz, 3H). $^{13}$C NMR (125 MHz, DMSO-$d_6$): δ 165.2, 163.5, 163.4, 160.5 [d, J (P, C)=5.25 Hz)], 158.2, 158.2, 150.4, 150.3, 150.2, 144.4, 135.4, 135.2, 135.2, 135.0, 135.0, 132.5 132.4, 130.1, 130.1, 129.7, 129.6, 128.0, 127.9, 127.6, 126.8, 113.2, 109.9, 109.9, 109.2, 107.1, 86.1, 84.5 [d, J (P, C)=9.25 Hz)], 84.0, 83.8, 83.3 [d, J (P, C)=6.06 Hz)], 78.8 [d, J (P, C)=4.46 Hz)], 78.2 [d, J (P, C)=4.74 Hz)], 73.3, 69.1, 67.2 [d, J (P, C)=5.91 Hz)], 63.0, 55.0, 55.0, 37.3, 26.6, 21.8 [d, J (P, C)=5.29 Hz)], 21.6, 18.5, 12.0, 11.6, 10.1. $^{31}$P NMR (202 MHz, DMSO-$d_6$): δ 66.02.

6.13. F-A-3'-OH

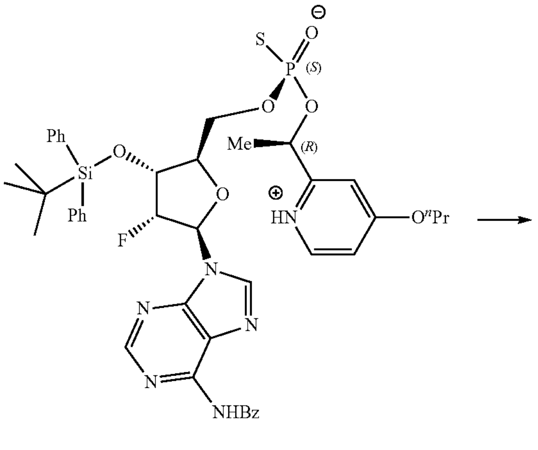

-continued

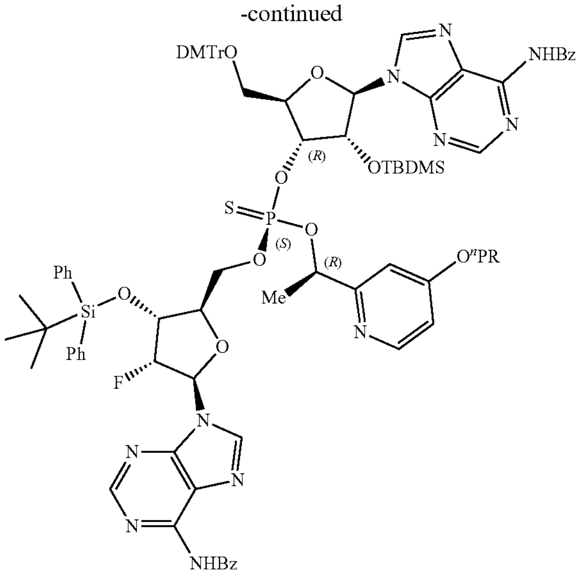

i) To a flask was charged (R, $R_p$)—FPPS$^{Pr}$ (0.42, 0.88 mmol) and N-{9-[(2R,3R,4R,5R)-4-[(tert-butyldiphenylsilyl)oxy]-3-fluoro-5-(hydroxymethyl)oxolan-2-yl]-9H-purin-6-yl}benzamide (0.5 g, 0.80 mmol). After the mixture was dried by evaporation of 5 mL of pyridine, pyridine (1.5 mL) was charged followed by addition of DMOCP (0.39 g, 2.1 mmol). After 1 h at 23° C., water (0.05 mL) was charged to quench the reaction. DBU (0.5 mL) was added. After 30 min, the mixture was diluted with 4 mL of 2M $KHSO_4$ and 5 mL of water and 5 mL of EtOAc. The organic layer was washed with 4 mL of 2M $KHSO_4$ and 5 mL of water. After concentration, 0.7 g of the crude product was isolated with quantitatively yield and directly used for next step.

ii) (S)-{[(2R,3R,4R,5R)-5-(6-benzamido-9H-purin-9-yl)-3-[(tert-butyldiphenylsilyl)oxy]-4-fluorooxolan-2-yl] methoxy}[(1R)-1-(4-propoxypyridin-2-yl)ethoxy]sulfanylidene-phosphinous acid (0.70 g, 0.804 mmol) and A-3'-OH (0.633 g, 0.804 mmol) were charged into a dry flask. After the mixture was dried by evaporation of pyridine (2×10 mL) under vacuum below 40° C. Pyridine (1.75 mL) was added followed by addition of DMOCP (0.371 g, 2.0 mmol). After 2 h at 23° C., the reaction was quenched with water. The product was extracted with EtOAc and washed with 2M $KHSO_4$ and then water. The organic layer was concentrated and the crude product was obtained with 99:1 dr and 92% solution yield. An analytically pure sample was obtained by purification on silica gel column with 0-100% EtOAc in hexane.

$^1$H NMR (500 MHz, DMSO-$d_6$): δ 11.12 (s, 1H), 8.47 (s, 1H), 8.45 (s, 1H), 8.42 (s, 1H), 8.39 (s, 1H), 8.19 (d, J=5.65 Hz, 1H), 7.97-7.93 (m, 4H), 7.66-7.62 (m, 4H), 7.57-7.53 (m, 2H), 7.47-7.33 (m, 10H), 7.30-7.29 (m, 2H), 7.16-7.09 (m, 7H), 6.81 (m, 1H), 6.79-6.78 (m, 1H), 6.74-6.72 (m, 4H), 6.35 (d, J=20.05 Hz, 1H), 5.92 (d, J=7.3 Hz, 1H), 5.40-5.34 (m, 1.5H), 5.27 (m, 0.5H), 5.16 (m, 1H), 5.04-4.96 (m, 2H), 4.36-4.23 (m, 3H), 3.83 (t, J=10.75 Hz, 2H), 3.63 (s, 1H), 3.63 (s, 1H), 3.20 (m, 1H), 3.08 (m, 1H), 1.56-1.52 (m, 2H), 1.33 (d, J=6.5 Hz, 3H), 1.05 (s, 9H), 0.77 (t, J=7.35 Hz, 3H), 0.42 (s, 9H), −0.35 (s, 3H), −0.51 (s, 3H). $^{13}$C NMR (125 MHz, DMSO-$d_6$): δ 166.0, 166.0, 165.7, 161.3 [d, J (P, C)=7.5 Hz], 158.6, 152.4, 151.9, 151.8, 151.7, 151.2, 151.1, 150.9, 145.1, 144.3, 144.0, 135.9, 135.9, 135.7, 135.5, 133.8, 132.9, 132.7, 132.6, 130.8, 130.7, 130.2, 130.1, 129.0, 128.9, 128.9, 128.5, 128.4, 128.2, 128.0, 127.1, 126.5, 126.3, 113.6, 113.6, 109.8, 107.1, 93.4, 91.9, 87.6, 87.4, 87.1, 86.3, 82.5, 81.6 [d, J (P, C)=8.3 Hz], 78.4, 78.4, 72.3 [d, J (P, C)=7.4 Hz], 71.4 [d, J (P, C)=15.9 Hz], 69.6, 68.3, 63.2, 55.5, 27.2, 25.5, 22.3 [d, J (P, C)=3.9 Hz], 19.4, 17.7, 10.6, -4.8, -5.3. $^{31}$P NMR (202 MHz, DMSO-$d_6$): δ 67.43. $^{19}$F NMR (470 MHz, DMSO-$d_6$): δ -201.7.

6.14. F—C-3'-OH

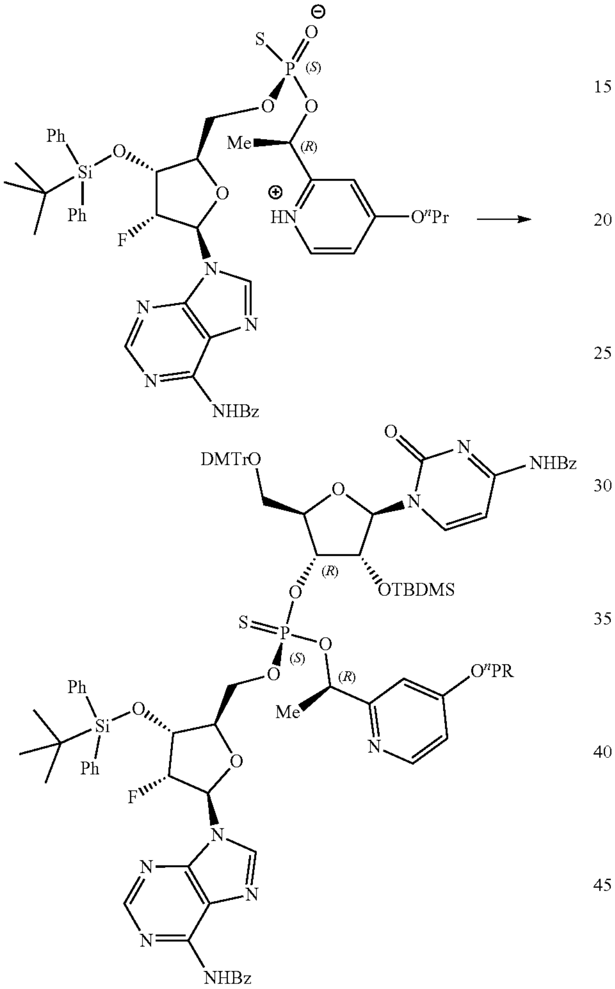

i) To a flask was charged (R, $R_p$)—FPPS$^{Pr}$ (0.42, 0.88 mmol) and N-{9-[(2R,3R,4R,5R)-4-[(tert-butyldiphenylsilyl)oxy]-3-fluoro-5-(hydroxymethyl)oxolan-2-yl]-9H-purin-6-yl}benzamide (0.5 g, 0.80 mmol). After the mixture was dried by evaporation of 5 mL of pyridine, pyridine (1.5 mL) was charged followed by addition of DMOCP (0.39 g, 2.1 mmol). After 1 h at 23° C., water (0.05 mL) was charged to quench the reaction. DBU (0.5 mL) was added. After 30 min, the mixture was diluted with 4 mL of 2M $KHSO_4$ and 5 mL of water and 5 mL of EtOAc. The organic layer was washed with 4 mL of 2M $KHSO_4$ and 5 mL of water. After concentration, 0.7 g of the crude product was isolated with quantitatively yield and directly used for next step.

ii) (S)-{[(2R,3R,4R,5R)-5-(6-benzamido-9H-purin-9-yl)-3-[(tert-butyldiphenylsilyl)oxy]-4-fluorooxolan-2-yl] methoxy}[(1R)-1-(4-propoxypyridin-2-yl)ethoxy]sulfanylidene-phosphinous acid (0.70 g, 0.804 mmol) and C-3'-OH (0.531 g, 0.804 mmol) were charged into a dry flask. After the mixture was dried by evaporation of pyridine (2×10 mL) under vacuum below 40° C. Pyridine (1.75 mL) was added followed by addition of DMOCP (0.371 g, 2.0 mmol, 2.5 eq). After 2 h at 23° C., the reaction was quenched with water. The product was extracted with EtOAc and washed with 2M $KHSO_4$ and then water. The organic layer was concentrated and the crude product was obtained with 98.9:1.1 dr and 90% solution yield. An analytically pure sample was obtained by purification on silica gel column with 0-100% EtOAc in hexane.

$^1$H NMR (500 MHz, DMSO-$d_6$): δ 11.27 (bs, 2H), 8.57 (s, 1H), 8.53 (s, 1H), 8.24 (d, J=6.35 Hz, 1H), 8.18 (bs, 1H), 8.07-8.04 (m, 4H), 7.75-7.73 (m, 4H), 7.70-7.66 (m, 3H), 7.60-7.47 (m, 10H), 7.40-7.39 (m, 2H), 7.34-7.31 (m, 2H), 7.27-7.26 (m, 5H), 7.18 (bs, 1H), 6.90 (d, J=7.7 Hz, 4H), 6.86 (bs, 2H), 6.45 (d, J=19.95 Hz, 1H), 5.90 (d, J=4.35 Hz, 1H), 5.48 (m, 0.5H), 5.41-5.35 (m, 1.5H), 5.12-5.06 (m, 1H), 4.93-4.89 (m, 1H), 4.44 (t, J=4.25 Hz, 1 h), 4.37-4.34 (m, 2H), 4.22 (m, 1H), 4.03 (m, 1H), 3.94 (t, J=6.45 Hz, 2H), 3.78 (s, 3H), 3.78 (s, 3H), 3.32-3.27 (m, 2H), 1.71-1.67 (m, 2H), 1.41 (d, J=6.45 Hz, 3H), 1.15 (s, 9H), 0.94 (t, J=7.35 Hz, 3H), 0.74 (s, 9H), 0.00 (s, 3H), -0.08 (s, 3H). $^{13}$C NMR (125 MHz, DMSO-$d_6$): δ 167.8, 166.0, 165.6, 163.8, 161.0, [d, J (P, C)=6.66 Hz], 158.7, 158.7, 154.8, 151.8, 151.7, 151.1, 150.8, 144.6, 144.2, 135.9, 135.8, 135.5, 135.2, 133.8, 133.5, 133.3, 132.9, 132.7, 132.5, 130.8, 130.7, 130.2, 130.2, 129.0, 129.0, 128.5, 128.4, 128.3, 128.2, 127.4, 126.3, 113.7, 109.7, 107.3, 97.0, 92.6 [d, J (F, C)=187.9 Hz], 89.6, 87.3 [d, J (P, C)=35.4 Hz], 86.8, 81.6, 81.5, 79.1, 78.3 [d, J (P, C)=4.56 Hz], 76.2, 74.5, 71.3 [d, J (P, C)=15.7 Hz], 69.6, 68.2, 62.4, 55.5, 55.4, 27.1, 25.8, 22.1, 22.0, 19.3, 18.0, 10.6, -4.7, -5.0. $^{31}$P NMR (202 MHz, DMSO-$d_6$): δ 67.32. $^{19}$F NMR (470 MHz, DMSO-$d_6$): δ -200.88.

6.15. F-G-3'-OH

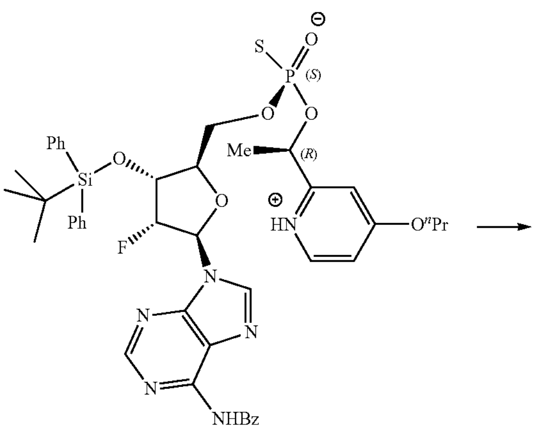

-continued

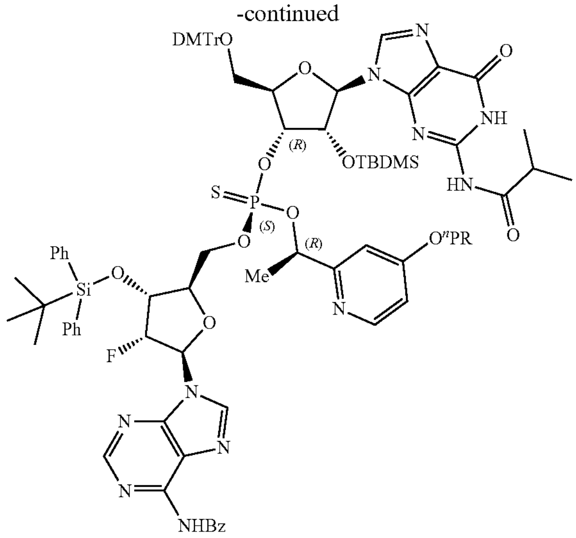

i) To a flask was charged (R, $R_p$)—FPPS$^{Pr}$ (0.42, 0.88 mmol) and N-{9-[(2R,3R,4R,5R)-4-[(tert-butyldiphenylsilyl)oxy]-3-fluoro-5-(hydroxymethyl)oxolan-2-yl]-9H-purin-6-yl}benzamide (0.5 g, 0.80 mmol). After the mixture was dried by evaporation of 5 mL of pyridine, pyridine (1.5 mL) was charged followed by addition of DMOCP (0.39 g, 2.1 mmol). After 1 h at 23° C., water (0.05 mL) was charged to quench the reaction. DBU (0.5 mL) was added. After 30 min, the mixture was diluted with 4 mL of 2M $KHSO_4$ and 5 mL of water and 5 mL of EtOAc. The organic layer was washed with 4 mL of 2M $KHSO_4$ and 5 mL of water. After concentration, 0.7 g of the crude product was isolated with quantitatively yield and directly used for next step.

ii) (S)-{[(2R,3R,4R,5R)-5-(6-benzamido-9H-purin-9-yl)-3-[(tert-butyldiphenylsilyl)oxy]-4-fluorooxolan-2-yl] methoxy}[(1R)-1-(4-propoxypyridin-2-yl)ethoxy]sulfanylidene-phosphinous acid (0.7 g, 0.804 mmol) and G-3'-OH (0.619 g, 0.804 mmol) were charged into a dry flask. After the mixture was dried by evaporation of pyridine (2×10 mL) under vacuum below 40° C. Pyridine (1.75 mL) was added followed by addition of DMOCP (0.371 g, 2.0 mmol). After 2 h at 23° C., the reaction was quenched with water. The product was extracted with EtOAc and washed with 2M $KHSO_4$ and then water. The organic layer was concentrated and the crude product was obtained with 98:2 dr and 85% solution yield. An analytically pure sample was obtained by purification on silica gel column with 0-100% EtOAc in hexane.

$^1$H NMR (500 MHz, DMSO-$d_6$): δ 12.30 (s, 1H), 11.85 (s, 1H), 11.43 (s, 1H), 8.81 (s, 1H), 8.69 (s, 1H), 8.51 (d, J=5.70 Hz, 1H), 8.25-8.24 (m, 3H), 7.95-7.93 (m, 4H), 7.87 (t, J=7.40 Hz, 1H), 7.78-7.67 (m, 8H), 7.56-7.55 (m, 2H), 7.50-7.42 (m, 7H), 7.12 (m, 1H), 7.09-7.06 (m, 5H), 6.69 (d, J=20.35 Hz, 1H), 6.03 (d, J=7.9 Hz, 1H), 5.68-5.58 (m, 2H), 5.36-5.31 (m, 1H), 5.13 (m, 1H), 4.99 (m, 1H), 4.58 (m, 2H), 4.39 (m, 1H), 4.15-4.12 (m, 3H), 3.97 (s, 6H), 3.40 (m, 2H), 2.92 (m, 1H), 1.87-1.83 (m, 2H), 1.74 (d, J=6.5 Hz, 3H), 1.35 (s, 9H), 1.33-1.30 (m, 6H), 1.09 (t, J=7.40 Hz, 3H), 0.71 (s, 9H), −0.03 (s, 3H), −0.14 (s, 3H). $^{13}$C NMR (126 MHz, DMSO-$d_6$): δ 180.5, 165.9, 165.7, 160.9 [d, J (P, C)=7.0 Hz], 158.7, 158.7, 155.1, 151.7, 151.7, 151.1, 151.0, 149.6, 149.0, 145.0, 144.4, 136.7, 135.9, 135.8, 135.5, 135.4, 133.7, 132.9, 132.6, 132.5, 130.8, 130.8, 128.9, 128.9, 128.6, 128.4, 128.3, 128.0, 127.3, 126.3, 120.4, 113.6, 109.9, 107.6, 92.8 [d, J (F, C)=187.2 Hz], 87.5 [d, J (P, C)=35.2 Hz], 86.4, 85.2, 83.0, 81.7 [d, J (P, C)=8.9 Hz], 78.8 [d, J (P, C)=5.1 Hz], 78.5 [d, J (P, C)=4.6 Hz], 74.6 [d, J (P, C)=7.3 Hz], 71.5 [d, J (P, C)=15.7 Hz], 69.6, 68.9, 63.6, 55.5, 55.5, 35.3, 27.1, 25.7, 25.4, 22.3 [d, J (P, C)=4.3 Hz], 22.1, 21.2, 19.3, 17.7, 10.5, −4.9, −5.5. $^{31}$P NMR (202 MHz, DMSO-$d_6$): δ 67.96. $^{19}$F NMR (470 MHz, DMSO-$d_6$): δ −201.2.

6.16. F—U-3'-OH

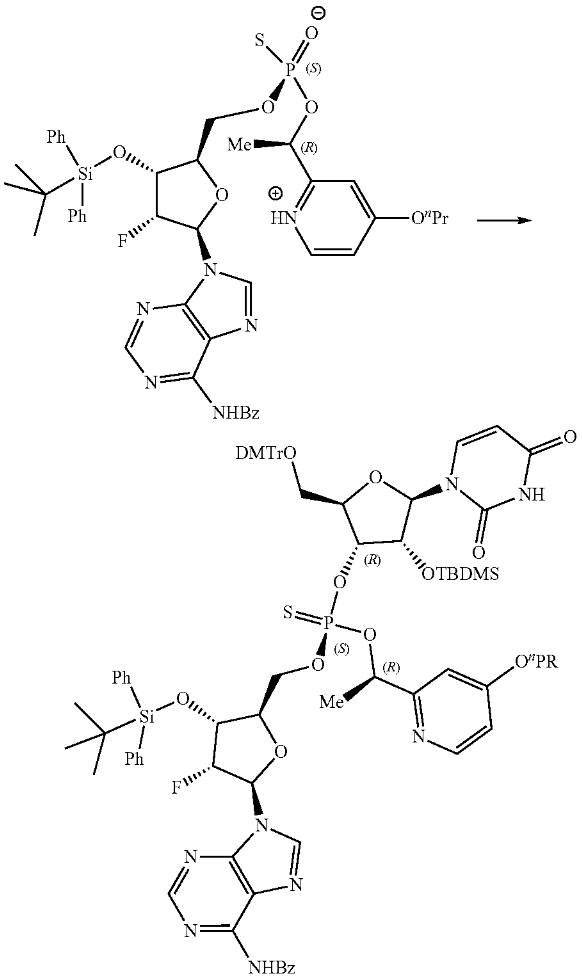

i) To a flask was charged (R, $R_p$)—FPPS$^{Pr}$ (0.42, 0.88 mmol) and N-{9-[(2R,3R,4R,5R)-4-[(tert-butyldiphenylsilyl)oxy]-3-fluoro-5-(hydroxymethyl)oxolan-2-yl]-9H-purin-6-yl}benzamide (0.5 g, 0.80 mmol). After the mixture was dried by evaporation of 5 mL of pyridine, pyridine (1.5 mL) was charged followed by addition of DMOCP (0.39 g, 2.1 mmol). After 1 h at 23° C., water (0.05 mL) was charged to quench the reaction. DBU (0.5 mL) was added. After 30 min, the mixture was diluted with 4 mL of 2M $KHSO_4$ and 5 mL of water and 5 mL of EtOAc. The organic layer was washed with 4 mL of 2M $KHSO_4$ and 5 mL of water. After concentration, 0.7 g of the crude product was isolated with quantitatively yield and directly used for next step.

ii) (S)-{[(2R,3R,4R,5R)-5-(6-benzamido-9H-purin-9-yl)-3-[(tert-butyldiphenylsilyl)oxy]-4-fluorooxolan-2-yl] methoxy}[(1R)-1-(4-propoxypyridin-2-yl)ethoxy]sulfanylidene-phosphinous acid (0.7 g, 0.804 mmol) and U-3'-OH (0.531 g, 0.804 mmol) were charged into a dry flask.

After the mixture was dried by evaporation of pyridine (2×10 mL) under vacuum below 40° C. Pyridine (1.75 mL) was added followed by addition of DMOCP (0.371 g, 2.0 mmol, 2.5 eq). After 2 h at 23° C., the reaction was quenched with water. The product was extracted with EtOAc and washed with 2M $KHSO_4$ and then water. The organic layer was concentrated and the crude product was obtained with 96.4:1.4 dr and 87% solution yield. An analytically pure sample was obtained by purification on silica gel column with 0-100% EtOAc in hexane.

$^1$H NMR (500 MHz, DMSO-$d_6$) δ 11.58 (s, 1H), 11.29 (s, 1H), 8.64 (s, 1H), 8.59 (s, 1H), 8.31 (d, J=5.15 Hz, 1H), 8.12 (d, J=7.45 Hz, 2H), 7.83-7.80 (m, 4H), 7.76 (t, J=7.35 Hz, 1H), 7.67-7.64 (m, 3H), 7.63-7.55 (m, 6H), 7.42-7.37 (m, 4H), 7.33 (m, 1H), 7.28-7.27 (m, 4H), 6.97-6.92 (m, 6H), 6.52 (d, J=20 Hz, 1H), 5.91 (d, J=6.7 Hz, 1H), 5.58-5.45 (m, 3H), 5.17 (m, 1H), 4.98 (m, 1H), 4.51-4.40 (m, 3H), 4.29-4.08 (m, 2H), 3.99 (t, J=6.25 Hz, 2H), 3.84 (bs, 6H), 3.19 (m, 2H), 1.78-1.71 (m, 2H), 1.43 (d, J=6.25 Hz, 1H), 1.23 (s, 9H), 1.00 (t, J=7.30 Hz, 3H), 0.79 (s, 9H), 0.02 (s, 3H), 0.00 (s, 3H). $^{13}$C NMR (125 MHz, DMSO-$d_6$): δ 166.0, 165.6, 163.1, 161.1 [d, J (P, C)=6.94 Hz)], 158.7, 158.7, 151.8, 151.7, 151.0, 150.9, 150.8, 144.7, 144.2, 139.9, 135.9, 135.8, 135.3, 135.0, 133.8, 132.9, 132.7, 132.5, 130.8, 130.7, 130.1, 128.9, 128.9, 120.5, 120.4, 120.4, 127.9, 127.3, 126.3, 113.7, 113.7, 109.8, 107.3, 102.8, 92.5 [d, J (F, C)=186.8 Hz)], 87.2, 86.8, 82.1, 81.4 [d, J (P, C)=9.24 Hz)], 78.4 [d, J (P, C)=4.59 Hz)], 77.5, 73.5 [d, J (P, C)=6.19 Hz)], 71.3 [d, J (P, C)=15.4 Hz)], 69.6, 68.0, 63.1, 55.5, 55.5, 27.2, 25.9, 25.7, 22.1, 19.3, 17.9, 10.6, −4.77, −5.06. $^{31}$P NMR (202 MHz, DMSO-$d_6$): δ 67.66. $^{19}$F NMR (470 MHz, DMSO-$d_6$): δ −201.5.

6.17. F-A-2'-OH

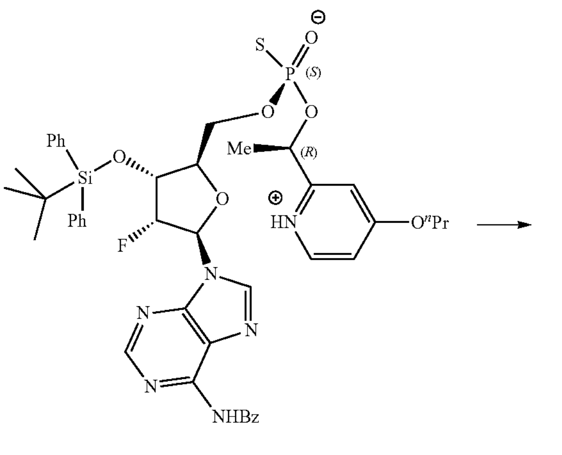

-continued

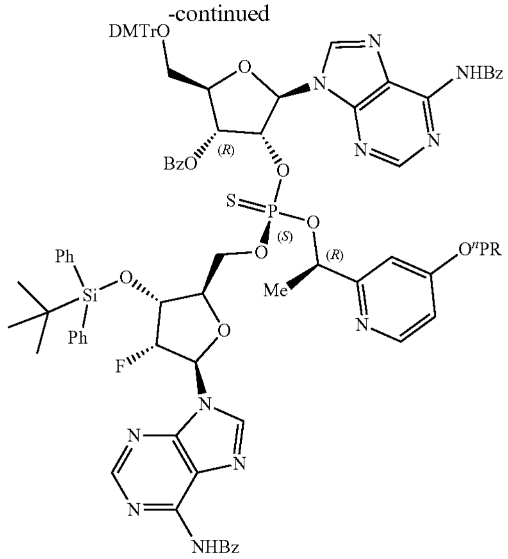

i) To a flask was charged (R, $R_p$)—$FPPS^{Pr}$ (0.42, 0.88 mmol) and N-{9-[(2R,3R,4R,5R)-4-[(tert-butyldiphenylsilyl)oxy]-3-fluoro-5-(hydroxymethyl)oxolan-2-yl]-9H-purin-6-yl}benzamide (0.5 g, 0.80 mmol). After the mixture was dried by evaporation of 5 mL of pyridine, pyridine (1.5 mL) was charged followed by addition of DMOCP (0.39 g, 2.1 mmol). After 1 h at 23° C., water (0.05 mL) was charged to quench the reaction. DBU (0.5 mL) was added. After 30 min, the mixture was diluted with 4 mL of 2M $KHSO_4$ and 5 mL of water and 5 mL of EtOAc. The organic layer was washed with 4 mL of 2M $KHSO_4$ and 5 mL of water. After concentration, 0.7 g of the crude product was isolated with quantitatively yield and directly used for next step.

ii) (S)-{[(2R,3R,4R,5R)-5-(6-benzamido-9H-purin-9-yl)-3-[(tert-butyldiphenylsilyl)oxy]-4-fluorooxolan-2-yl]methoxy}[(1R)-1-(4-propoxypyridin-2-yl)ethoxy]sulfanylidene-phosphinous acid (0.7 g, 0.804 mmol) and (2R,3S,4R,5R)-5-(6-benzamido-9H-purin-9-yl)-2-{[bis(4-methoxyphenyl)(phenyl)methoxy]methyl}-4-hydroxyoxolan-3-yl benzoate (0.656 g, 0.844 mmol) were charged into a dry flask. After the mixture was dried by evaporation of pyridine (2×10 mL) under vacuum below 40° C. Pyridine (1.75 mL) was added followed by addition of DMOCP (0.371 g, 2.0 mmol, 2.5 eq). After 2 h at 23° C., the reaction was quenched with water. The product was extracted with EtOAc and washed with 2M $KHSO_4$ and then water. The organic layer was concentrated and the crude product was obtained with 96.8: 3.2 dr and 85% solution yield. An analytically pure sample was obtained by purification on silica gel column with 0-100% EtOAc in hexane.

$^1$H NMR (500 MHz, DMSO-$d_6$): δ 11.24 (s, 1H), 11.18 (s, 1H), 8.61 (s, 1H), 8.53 (s, 1H), 8.49 (s, 1H), 8.47 (s, 1H), 8.17 (d, J=5.75 Hz, 1H), 8.07-8.03 (m, 4H), 7.90 (d, J=7.35 Hz, 2H), 7.66-7.62 (m, 7H), 7.56-7.52 (m, 4H), 7.47-7.36 (m, 10H), 7.25-7.14 (m, 7H), 6.82-6.76 (m, 6H), 6.44 (m, 1H), 6.29 (d, J=19.2 Hz, 1H), 6.09 (m, 1H), 5.98 (m, 1H), 5.31-5.20 (m, 2H), 4.88 (m, 1H), 4.46 (m, 1H), 4.20-4.14 (m, 3H), 3.94-3.84 (m, 3H), 3.68 (s, 6H), 3.43-3.35 (m, 2H), 1.69-1.65 (m, 2H), 1.06 (s, 9H), 0.91 (t, J=7.35 Hz, 3H). $^{13}$C NMR (125 MHz, DMSO-$d_6$): δ 164.0, 163.9, 163.5, 163.0, 158.9 [d, J (P, C)=6.84 Hz], 156.4, 150.1, 150.0, 149.8, 149.6, 149.0, 148.8, 148.5, 142.9, 141.9, 141.7, 133.7, 133.6, 133.6, 133.5, 132.0, 131.7, 131.6, 130.8, 130.8, 130.5, 130.4, 128.6, 128.5, 128.1, 128.0, 127.7, 127.1, 126.9, 126.9, 126.8, 126.3, 126.2, 126.1, 126.0, 125.0, 124.1, 124.1, 111.5, 107.7, 104.7, 90.2 [d, J (F, C)=188.4 Hz], 85.0 [d, J (P, C)=11.5 Hz], 84.7, 84.2, 79.3 [d, J (P, C)=5.0 Hz], 79.0, 76.4 [d, J (P, C)=5.0 Hz], 74.1, 69.3 [d, J (P, C)=4.8 Hz], 69.0 [d, J (P, C)=15.7 Hz], 67.4, 65.7, 60.7, 53.3, 53.3, 25.0, 25.0, 20.0, 20.0, 17.2, 8.5.

$^{31}$P NMR (202 MHz, DMSO-$d_6$): δ 66.76. $^{19}$F NMR (470 MHz, DMSO-$d_6$): δ −201.5.

F-A-2-OH-DTBS $^1$H NMR (500 MHz, DMSO-$d_6$): δ 11.21 (bs, 2H), 8.62 (s, 1H), 8.55 (s, 1H), 8.49 (s, 1H), 8.48 (s, 1H), 8.21 (d, J=5.70 Hz, 1H), 8.05 (d, J=7.45 Hz, 2H), 8.01 (d, J=7.50 Hz, 2H), 7.68-7.67 (m, 4H), 7.64-7.61 (m, 2H), 7.56-7.51 (m, 4H), 7.49-7.41 (m, 6H), 6.86 (d, J=2.1 Hz, 1H), 6.80 (m, 1H), 6.34 (d, J=19.55 Hz, 1H), 6.24 (s, 1H), 5.44-5.35 (m, 2.5H), 5.28 (m, 0.5H), 4.93 (m, 1H), 4.33-4.30 (m, 3H), 4.12 (m, 1H), 3.94-3.91 (m, 3H), 3.84 (m, 1H), 1.71-1.67 (m, 2H), 1.36 (d, J=6.45 Hz, 3H), 1.08 (s, 9H), 0.99 (s, 9H), 0.92 (t, J=7.35 Hz, 3H), 0.83 (s, 9H). $^{13}$C NMR (125 MHz, DMSO-$d_6$): δ 166.2, 166.1, 165.7, 161.1 [d, J (P, C)=6.74 Hz], 152.2, 151.8, 151.8, 151.6, 151.1, 151.0, 150.8, 144.0, 143.9, 135.8, 135.8, 133.7, 132.0, 132.9, 130.8, 130.7, 129.0, 128.9, 128.9, 128.5, 128.4, 126.1, 126.0, 109.3, 107.4, 92.4 [d, J (F, C)=188.4 Hz], 88.7, 87.0 [d, J (P, C)=34.63 Hz], 81.7 [d, J (P, C)=8.35 Hz], 78.5 [d, J (P, C)=5.6 Hz], 78.4 [d, J (P, C)=5.6 Hz], 74.6, 74.6, 71.3 [d, J (P, C)=15.67 Hz], 69.6, 67.9, 67.0, 27.5, 27.1, 27.1, 22.6, 22.4, 22.3, 22.1, 20.2, 19.3, 10.7. $^{31}$P NMR (202 MHz, DMSO-$d_6$): δ 65.76. $^{19}$F NMR (470 MHz, DMSO-$d_6$): δ −201.5.

6.18. F—C-2'-OH

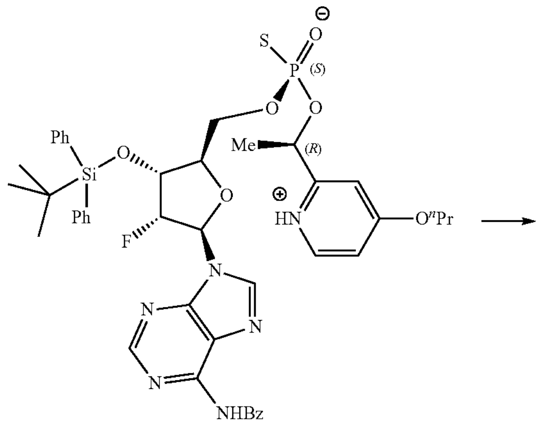

-continued

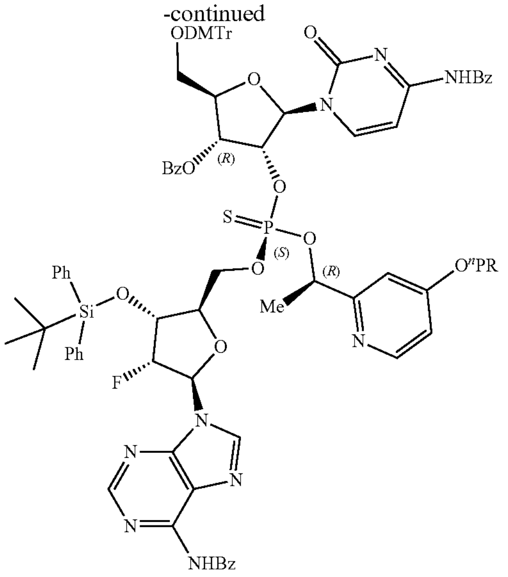

i) To a flask was charged (R, $R_p$)—FPPS$^{Pr}$ (0.42, 0.88 mmol) and N-{9-[(2R,3R,4R,5R)-4-[(tert-butyldiphenylsilyl)oxy]-3-fluoro-5-(hydroxymethyl)oxolan-2-yl]-9H-purin-6-yl}benzamide (0.5 g, 0.80 mmol). After the mixture was dried by evaporation of 5 mL of pyridine, pyridine (1.5 mL) was charged followed by addition of DMOCP (0.39 g, 2.1 mmol). After 1 h at 23° C., water (0.05 mL) was charged to quench the reaction. DBU (0.5 mL) was added. After 30 min, the mixture was diluted with 4 mL of 2M $KHSO_4$ and 5 mL of water and 5 mL of EtOAc. The organic layer was washed with 4 mL of 2M $KHSO_4$ and 5 mL of water. After concentration, 0.7 g of the crude product was isolated with quantitatively yield and directly used for next step.

ii) (S)-{[(2R,3R,4R,5R)-5-(6-benzamido-9H-purin-9-yl)-3-[(tert-butyldiphenylsilyl)oxy]-4-fluorooxolan-2-yl]methoxy}[(1R)-1-(4-propoxypyridin-2-yl)ethoxy]sulfanylidene-phosphinous acid (0.7 g, 0.804 mmol) and (2R,3S,4R,5R)-5-(6-benzamido-9H-purin-9-yl)-2-{[bis(4-methoxyphenyl)(phenyl)methoxy]methyl}-4-hydroxyoxolan-3-yl benzoate (0.606 g, 0.804 mmol) were charged into a dry flask. After the mixture was dried by evaporation of pyridine (2×10 mL) under vacuum below 40° C. Pyridine (1.75 mL) was added followed by addition of DMOCP (0.371 g, 2.0 mmol, 2.5 eq). After 2 h at 23° C., the reaction was quenched with water. The product was extracted with EtOAc and washed with 2M $KHSO_4$ and then water. The organic layer was concentrated and the crude product was obtained with 97.1:2.9 dr and 86% solution yield. An analytically pure sample was obtained by purification on silica gel column with 0-100% EtOAc in hexane.

$^1$H NMR (500 MHz, DMSO-$d_6$): δ 11.37 (s, 1H), 11.18 (s, 1H), 8.52 (s, 1H), 8.51 (s, 1H), 8.25 (s, 1H), 8.24 (s, 1H), 8.03 (d, J=7.70 Hz, 4H), 7.85 (d, J=7.35 Hz, 2H), 7.69-7.61 (m, 7H), 7.54-7.51 (m, 4H), 7.46-7.35 (m, 10H), 7.30-7.17 (m, 8H), 6.89 (d, J=2.2 Hz, 1H), 6.85-6.80 (m, 5H), 6.39 (dd, J=1.95, 18.75 Hz, 1H), 5.99 (d, J=2.5 Hz, 1H), 5.70 (m, 1H), 5.47 (m, 1H), 5.39 (m, 0.5H), 5.31-5.28 (m, 1.5H), 4.95 (m, 1H), 4.39-4.30 (m, 3H), 4.12 (m, 1H), 3.97-3.90 (m, 2H), 3.68 (s, 6H), 3.40 (m, 2H), 1.68-1.64 (m, 2H), 1.17 (t, J=7.15 Hz, 3H), 1.08 (s, 9H), 0.89 (t, J=7.35 Hz, 3H). $^{13}$C NMR (125 MHz, DMSO-$d_6$): δ 167.9, 166.0, 165.7, 165.1, 164.3, 161.3 [d, J (P, C)=6.83 Hz], 158.6, 158.6, 154.6, 151.9, 151.8, 151.0, 150.7, 146.6, 144.7, 143.8, 135.8, 135.8, 135.5, 135.5, 134.1, 133.8, 133.5, 133.3, 132.9, 132.7, 132.6, 130.7, 130.6, 130.1, 130.1, 129.9, 129.8, 129.2, 129.1, 129.0, 128.9, 128.9, 128.4, 128.4, 128.1, 127.3, 126.2, 113.7, 109.8, 106.8, 97.2, 93.0, 91.5, 86.9, 86.7, 81.5 [d, J (P, C)=7.84 Hz], 80.4, 78.3 [d, J (P, C)=4.74 Hz], 77.5, 71.2 [d, J (P, C)=15.16 Hz], 70.5, 69.6, 67.6, 64.5, 55.4, 27.1, 22.2, 22.1 [d, J (P, C)=4.11 Hz], 19.3, 10.6. $^{31}$P NMR (202 MHz, DMSO-$d_6$): δ 66.76. $^{19}$F NMR (470 MHz, DMSO-$d_6$): δ −201.5.

6.19. F-G-2'-OH

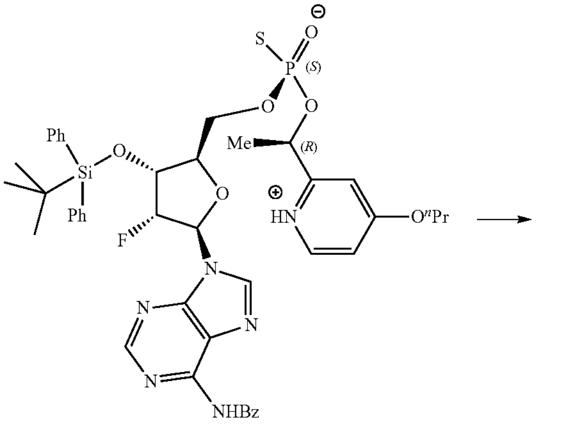

i) To a flask was charged (R, $R_p$)—FPPS$^{Pr}$ (0.42, 0.88 mmol) and N-{9-[(2R,3R,4R,5R)-4-[(tert-butyldiphenylsilyl)oxy]-3-fluoro-5-(hydroxymethyl)oxolan-2-yl]-9H-purin-6-yl}benzamide (0.5 g, 0.80 mmol). After the mixture was dried by evaporation of 5 mL of pyridine, pyridine (1.5 mL) was charged followed by addition of DMOCP (0.39 g, 2.1 mmol). After 1 h at 23° C., water (0.05 mL) was charged to quench the reaction. DBU (0.5 mL) was added. After 30 min, the mixture was diluted with 4 mL of 2M $KHSO_4$ and 5 mL of water and 5 mL of EtOAc. The organic layer was washed with 4 mL of 2M $KHSO_4$ and 5 mL of water. After concentration, 0.7 g of the crude product was isolated with quantitatively yield and directly used for next step.

ii) (S)-{[(2R,3R,4R,5R)-5-(6-benzamido-9H-purin-9-yl)-3-[(tert-butyldiphenylsilyl)oxy]-4-fluorooxolan-2-yl] methoxy}[(1R)-1-(4-propoxypyridin-2-yl)ethoxy]sulfanylidene-phosphinous acid (0.25 g, 0.287 mmol) and G-2'-OH (0.218 g, 0.287 mmol) was charged into a dry flask. After the mixture was dried by evaporation of pyridine (2×10 mL) under vacuum below 40° C. Pyridine (1.75 mL) was added followed by addition of DMOCP (0.132 g, 0.718 mmol, 2.5 eq). After 2 h at 23° C., the reaction was quenched with water. The product was extracted with EtOAc and washed with 2M $KHSO_4$ and then water. The organic layer was concentrated and the crude product was obtained with 97.7:2.3 dr and 82% solution yield. An analytically pure sample was obtained by purification on silica gel column with 0-100% EtOAc in hexane.

$^1$H NMR (500 MHz, DMSO-$d_6$): δ 8.44 (s, 1H), 8.43 (s, 1H), 8.16 (d, J=5.60 Hz, 1H), 8.05 (d, J=7.35 Hz, 2H), 8.01 (s, 1H), 7.86 (d, J=7.40 Hz, 2H), 7.66-7.63 (m, 6H), 7.54 (t, J=7.70 Hz, 2H), 7.46-7.38 (m, 8H), 7.35 (d, J=6.50 Hz, 2H), 7.29-7.15 (m, 7H), 6.86-6.78 (m, 2H), 6.76-6.74 (m, 2H), 6.27 (d, J=18.7 Hz, 1H), 6.19 (d, J=5.60 Hz, 1H), 5.80 (m, 1H), 5.72 (m, 1H), 5.30-5.25 (m, 1.5H), 5.18 (m, 0.5H), 4.93-4.87 (m, 1H), 4.41 (m, 1H), 4.23-4.19 (m, 2H), 3.91-3.84 (m, 3H), 3.69 (s, 6H), 3.49 (m, 1H), 3.33 (m, 1H), 2.68 (m, 1H), 1.67-1.62 (m, 2H), 1.18 (d, J=6.45 Hz, 3H), 1.08-1.05 (m, 15H), 0.89 (t, J=7.40 Hz, 3H). $^{13}$C NMR (125 MHz, DMSO-$d_6$): δ 178.5, 164.0, 163.5, 162.9, 158.8 [d, J (P, C)=7.25 Hz], 156.5, 156.5, 154.4, 150.0, 149.4, 149.1, 148.5, 147.6, 142.9, 141.7, 135.2, 133.7, 133.6, 132.0, 131.9, 130.6, 130.4, 128.6, 128.5, 128.1, 128.0, 127.6, 127.1, 127.0, 126.9, 126.8, 126.2, 126.1, 126.0, 125.1, 124.1, 118.6, 111.5, 107.6, 104.7, 90.3 [d, J (F, C)=187.75 Hz], 84.9 [d, J (P, C)=34.6 Hz], 84.3, 83.5, 79.9, 79.2 [d, J (P, C)=7.94 Hz], 76.4 [d, J (P, C)=4.8 Hz], 74.6, 70.0, 69.0 [d, J (P, C)=15.5 Hz], 67.4, 65.8, 61.8, 53.3, 33.3, 25.0, 20.0, 17.4, 17.3, 17.2. $^{31}$P NMR (202 MHz, DMSO-$d_6$): δ 66.76. $^{19}$F NMR (470 MHz, DMSO-$d_6$): δ −201.04.

6.20. F—U-2'-OH

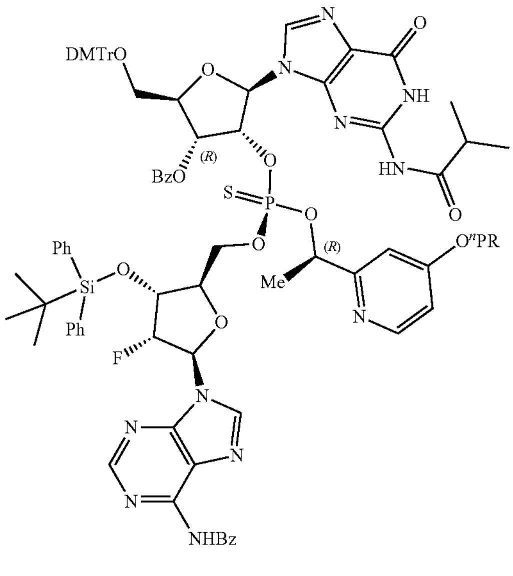

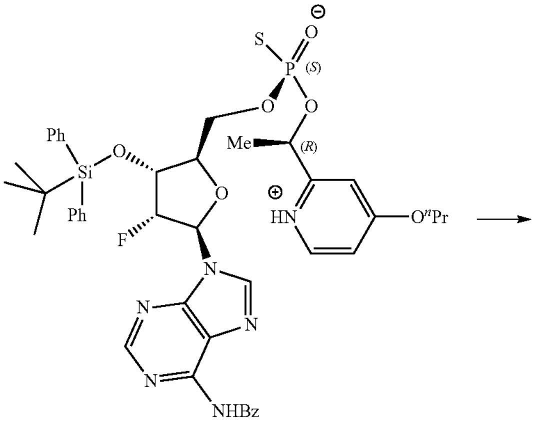

-continued

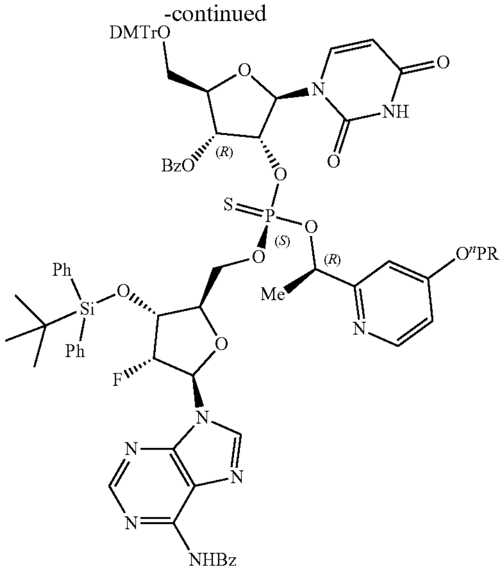

i) To a flask was charged (R, $R_p$)—$FPPS^{Pr}$ (0.42, 0.88 mmol) and N-{9-[(2R,3R,4R,5R)-4-[(tert-butyldiphenylsilyl)oxy]-3-fluoro-5-(hydroxymethyl)oxolan-2-yl]-9H-purin-6-yl}benzamide (0.5 g, 0.80 mmol). After the mixture was dried by evaporation of 5 mL of pyridine, pyridine (1.5 mL) was charged followed by addition of DMOCP (0.39 g, 2.1 mmol). After 1 h at 23° C., water (0.05 mL) was charged to quench the reaction. DBU (0.5 mL) was added. After 30 min, the mixture was diluted with 4 mL of 2M $KHSO_4$ and 5 mL of water and 5 mL of EtOAc. The organic layer was washed with 4 mL of 2M $KHSO_4$ and 5 mL of water. After concentration, 0.7 g of the crude product was isolated with quantitatively yield and directly used for next step.

ii) (S)-{[(2R,3R,4R,5R)-5-(6-benzamido-9H-purin-9-yl)-3-[(tert-butyldiphenylsilyl)oxy]-4-fluorooxolan-2-yl]methoxy}[(1R)-1-(4-propoxypyridin-2-yl)ethoxy]sulfanylidene-phosphinous acid (0.7 g, 0.804 mmol) and (2R,3S,4R,5R)-5-(6-benzamido-9H-purin-9-yl)-2-{[bis(4-methoxyphenyl)(phenyl)methoxy]methyl}-4-hydroxyoxolan-3-yl benzoate (0.656 g, 0.844 mmol, 1.05 eq.) were charged into a dry flask. After the mixture was dried by evaporation of pyridine (2×10 mL) under vacuum below 40° C. Pyridine (1.75 mL) was charged followed by addition of DMOCP (0.37 g, 2.0 mmol; 2.5 eq). After 2 h at 23° C., the reaction was quenched with water. The product was extracted with EtOAc and washed sequentially with 2M $KHSO_4$ and water. The organic layer was concentrated and the crude product was obtained with 97.1:2.9 dr and 87% solution yield. An analytically pure sample was obtained by purification on silica gel column with 0-100% EtOAc in hexane.

$^1$H NMR (500 MHz, DMSO-$d_6$) δ 11.49 (s, 1H), 11.17 (s, 1H), 8.47 (bs, 2H), 8.20 (d, J=5.35 Hz, 1H), 8.02 (d, J=7.40 Hz, 2H), 7.83 (d, J=7.55 Hz, 2H), 7.68-7.60 (m, 7H), 7.54 (t, J=7.30 Hz, 2H), 7.47-7.39 (m, 8H), 7.34-7.33 (m, 2H), 7.25-7.17 (m, 7H), 6.84-6.82 (m, 5H), 6.79 (d, J=5.30 Hz, 1H), 6.35 (d, J=19.4 Hz, 1H), 5.96 (d, J=3.4 Hz, 1H), 5.60 (m, 1H), 5.45-5.39 (m, 2H), 5.34-5.24 (m, 2H), 4.96-4.92 (m, 1H), 4.30-4.23 (m, 3H), 4.08-4.01 (m, 1H), 3.93-3.89 (m, 2H), 3.69 (s, 6H), 3.38-3.29 (m, 2H), 1.69-1.65 (m, 2H), 1.18 (d, J=6.30 Hz, 3H), 1.08 (s, 9H), 0.91 (t, J=7.25 Hz, 3H). $^{13}$C NMR (125 MHz, DMSO-$d_6$): δ 166.0, 165.7, 165.0, 163.3, 161.1 [d, J (P, C)=7.24 Hz)], 158.6, 158.6, 151.9, 151.7, 151.0, 150.7, 150.6, 144.9, 144.0, 141.7, 135.8, 135.8, 135.5, 135.4, 134.1, 133.8, 132.9, 132.7, 132.6, 130.7, 130.7, 130.2, 130.1, 129.8, 129.1, 129.0, 129.0, 128.9, 128.5, 128.4, 128.3, 128.1, 127.3, 126.2, 113.7, 109.8, 106.7, 102.7, 92.3 [d, J (F, C)=188.2 Hz)], 89.9, 87.0 [d, J (P, C)=34.19 Hz)], 86.6, 81.3 [d, J (P, C)=9.55 Hz)], 80.7, 78.4 [d, J (P, C)=4.66 Hz)], 76.6, 71.2, 71.1, 69.6, 67.6, 63.1, 55.5, 55.5, 27.1, 22.1, 22.1, 22.1, 21.2, 19.3, 10.7. $^{31}$P NMR (202 MHz, DMSO-$d_6$): δ 67.07. $^{19}$F NMR (470 MHz, DMSO-$d_6$): δ -201.4.

Example 7

Synthesis of Tetramer

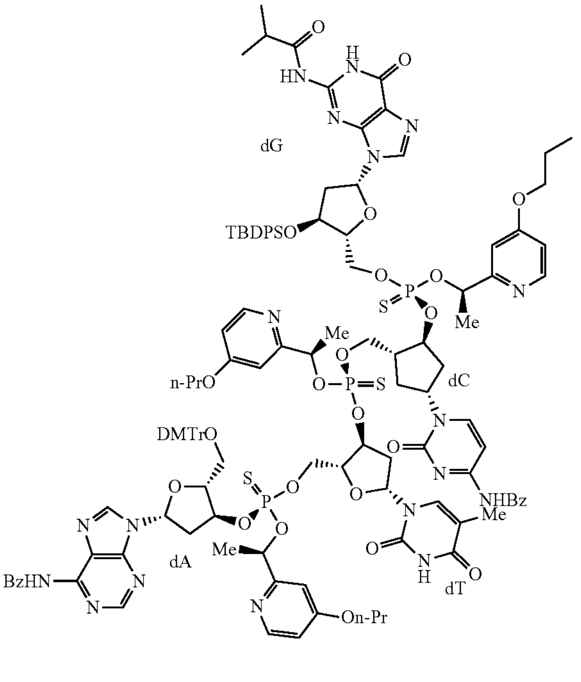

Step 1: Synthesis of dC-dG-P(V)

To a dry flask was charged dC-dG without DMTr (350 mg, 0.305 mmol), FPPSPr (145.9 mg, 0.317 mmol) and pyridine (1.05 mL). Then diisopropyl chlorophosphate (157.6 mg, 0.762 mmol, 2.5 eq) was added. After 2 h at 23° C., water (0.035 mL) was added. After 10 min, DBU (0.35 mL) was added. After 10 min, the product was extracted with EtOAc and then washed with 2M $KHSO_4$. The crude product was isolated with 94:6 dr and used for next step directly. An analytic sample was obtained by purification on silica gel with 0-10% MeOH in $CH_2Cl_2$.

Step 2: Synthesis of dC-dG-dT-dA

To a dry flask was charged dC-dG-P(V) (0.1 g, 0.071 mmol) and dA-dT without TBDPS (0.081 g, 0.071 mmol). The mixture was dried by co-evaporation of pyridine. After pyridine (0.25 mL) was charged, DMOCP (0.033 g, 0.178 mmol) was added. After 2 h at 23° C., the reaction gave full conversion. The product was extracted with EtOAc and then washed with 2M $KHSO_4$. The crude product was purified on C18 reverse phase column with 0-100% MeOH in water and isolated with 87% yield.

$^1$H NMR (500 MHz, DMSO-$d_6$) δ 12.06 (s, 1H), 11.54 (s, 1H), 11.33 (s, 1H), 11.27 (s, 1H), 11.19 (s, 1H), 8.56 (s, 1H), 8.54 (s, 1H), 8.29 (d, J=4.8 Hz, 1H), 8.25 (d, J=4.75 Hz, 1H), 8.22 (d, J=4.70 Hz, 1H), 8.11 (d, J=6.1 Hz, 1H), 8.04 (d, J=6.25 Hz, 2H), 7.99 (s, 1H), 7.98 (d, J=7.3 Hz, 2H), 7.65-7.53 (m, 8H), 7.50-7.42 (m, 8H), 7.37-7.32 (m, 3H), 7.28 (s, 1H), 7.21-7.18 (m, 6H), 7.15 (m, 1H), 6.94 (d, J=1.9 Hz, 1H), 6.91 (d, J=1.9 Hz, 1H), 6.86 (d, J=1.9 Hz, 1H), 6.82-6.76 (m, 7H), 6.46 (t, J=5.8 Hz, 1H), 6.31 (m, 1H), 6.12-6.08 (m, 2H), 5.54-5.51 (m, 2H), 5.43-5.40 (m, 2H), 5.06 (m, 1H), 4.96 (m, 1H), 4.39 (bs, 1H), 4.32-4.28 (m, 2H), 4.27-4.24 (m, 2H), 4.17-4.12 (m, 2H), 4.09 (bs, 2H), 3.93-3.84 (m, 8H), 3.69 (s, 3H), 3.68 (s, 3H), 3.29-3.24 (m, 5H), 2.76 (m, 1H), 2.63 (m, 1H), 2.55 (m, 1H), 2.31 (m, 1H), 2.25 (m, 1H), 2.08 (m, 1H), 1.67-1.61 (m, 9H), 1.56-1.51 (m, 9H), 1.28-1.19 (m, 4H), 1.11 (d, J=5.7 Hz, 6H), 1.03 (s, 9H), 0.91-0.84 (m, 9H). $^{13}$C NMR (125 MHz, DMSO-$d_6$): no data was collected due to the complex NMR. $^{31}$P NMR (202 MHz, DMSO-$d_6$): δ 65.65, 65.62.

The invention claimed is:

1. A compound of formula (I)

(I)

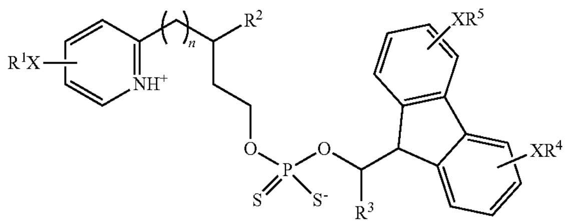

wherein n is 0, 1, 2, 3, 4, 5, or 6;

each X is selected from the group consisting of a bond; —$(CH_2)_m$— optionally substituted with halogen, —CN, $C_{1-3}$alkyl or —O—$C_{1-3}$alkyl; O; $NR^N$ and S; wherein m is 1, 2, 3 or 4, and $R^N$ is H or $C_{1-3}$alkyl;

$R^1$ is selected from the group consisting of H, $C_{1-6}$alkyl, $C_{3-6}$cycloalkyl, —$CH_2$-$C_{3-10}$cycloalkyl, aryl, —$CH_2$-aryl, and heteroaryl, wherein each aryl and heteroaryl group is optionally substituted with 1-3 substituents selected from the group consisting of halogen, —CN, $C_{1-3}$alkyl and —O—$C_{1-3}$alkyl;

$R^2$ is selected from the group consisting of $C_{1-4}$alkyl, —C(O)OR$^6$, and aryl, wherein each alkyl group of $R^2$ is optionally substituted with halogen, cyano, or trimethylsilyl, and wherein $R^6$ is a $C_{1-4}$alkyl;

$R^3$ is selected from the group consisting of H, $C_{1-6}$alkyl, $C_{3-6}$cycloalkyl,—$CH_2$—$C_{3-10}$cycloalkyl, aryl, —$CH_2$-aryl, and heteroaryl, wherein each aryl and heteroaryl group is optionally substituted with 1-3 substituents selected from the group consisting of halogen,—CN, $C_{1-3}$alkyl and —O—$C_{1-3}$alkyl; and $R^4$ and $R^5$ are each independently of each other selected from the group consisting of H, $C_{1-6}$alkyl, $C_{3-6}$cycloalkyl, —$CH_2$—$C_{3-10}$cycloalkyl, aryl, —$CH_2$-aryl, and heteroaryl, wherein each aryl and heteroaryl group is optionally substituted with 1-3 substituents selected from the group consisting of halogen,—CN, $C_{1-3}$alkyl and —O-$C_{1-3}$alkyl;

or a tautomer, stereoisomer or salt thereof.

2. A compound of formula (I) according to claim 1, wherein n is 0 or 1;

X is selected from the group consisting of a bond, O, NH, $NCH_3$ and S;

$R^1$ is selected from the group consisting of H, $C_{1-4}$alkyl, —$CH_2$-$C_{3-6}$cycloalkyl, and —$CH_2$-phenyl, wherein the phenyl group is optionally substituted with 1 to 3 substituents selected from the group consisting of halogen, —CN, $CH_3$ and —O—$CH_3$;

$R^2$ is selected from the group consisting of $C_{1-4}$alkyl optionally substituted with one or more F, or with one substituent selected from Cl, Br, cyano, and trimethylsilyl;

$R^3$ is selected from the group consisting of H and $C_{1-3}$alkyl;

$R^4$ is selected from the group consisting of H and $C_{1-3}$alkyl; and $R^5$ is selected from the group consisting of H and $C_{1-3}$alkyl;

or a tautomer, stereoisomer or salt thereof.

3. A compound of formula (I) according to claim 2, wherein n is 0 or 1;

X is selected from the group consisting of a bond, O, NH, and S;

$R^1$ is selected from the group consisting of H and $C_{1-4}$alkyl;

$R^2$ is a $C_{1-3}$alkyl optionally substituted with one or more F;

$R^3$ is selected from the group consisting of H and $C_{1-3}$alkyl;

$R^4$ is selected from the group consisting of H and $C_{1-3}$alkyl; and $R^5$ is selected from the group consisting of H and $C_{1-3}$alkyl;

or an enantiomer, diastereomer or salt thereof.

4. A compound of formula (I) according to claim 3, wherein n is 0;

X is selected from the group consisting of a bond and O;

$R^1$ is selected from the group consisting of H and $C_{1-4}$alkyl;

$R^2$ is a $C_{1-2}$alkyl optionally substituted with one to three F;

$R^3$ is H;

$R^4$ is H; and $R^5$ is H;

or an enantiomer, diastereomer or salt thereof.

5. A compound of formula (I) according to claim 4, wherein n is 0;

X is selected from the group consisting of a bond and O;

$R^1$ is selected from the group consisting of H and $C_{1-4}$alkyl;

$R^2$ is a $C_{1-2}$alkyl;

$R^3$ is H;

$R^4$ is H; and $R^5$ is H;

or an enantiomer, diastereomer or salt thereof.

6. A compound of formula (I) according to claim 5, wherein n is 0;

X is selected from the group consisting of a bond and O;

$R^1$ is selected from the group consisting of H and $C_{1-4}$alkyl;

$R^2$ is $CH_3$;

$R^3$ is H;

$R^4$ is H; and $R^5$ is H;

or an enantiomer, diastereomer or salt thereof.

7. A compound according to claim 1 having formula (I.2)

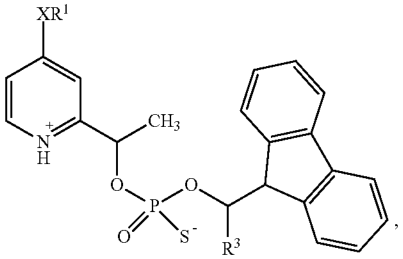

wherein

X is O;

$R^1$ is selected from the group consisting of H and $C_{1-4}$alkyl;

$R^2$ is $CH_3$; and $R^3$ is H;

or an enantiomer, diastereomer or salt thereof.

8. A compound of formula (I.2) according to claim 7 wherein

X is O;

$R^1$ is $C_{1-3}$alkyl; $R^2$ is $CH_3$, and $R^3$ is H;

or an enantiomer, diastereomer or salt thereof.

9. The compound according to claim 7, with the structure and stereochemistry shown in formulae I.2a or I.2b (I.2a)

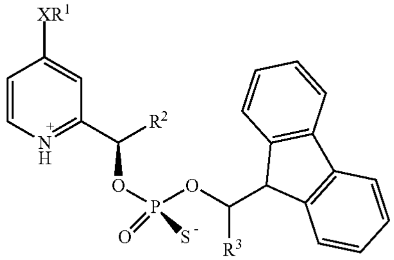

(I.2b)

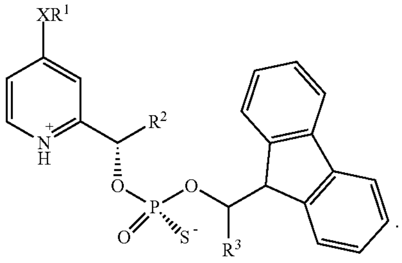

10. A compound according to claim 1 selected from the group consisting of:

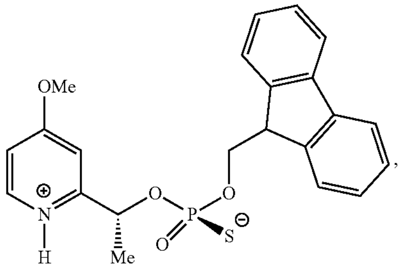

(R, $R_P$)

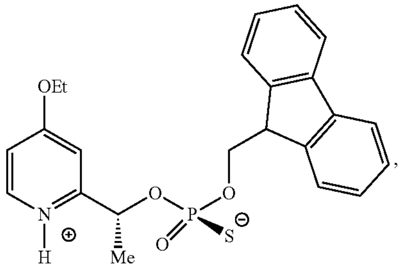

(R, $R_P$)

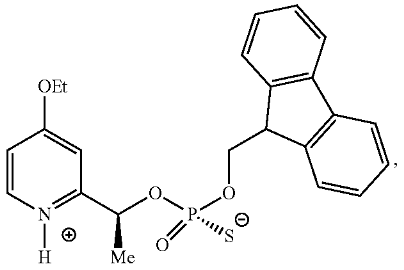

(S, $S_P$)

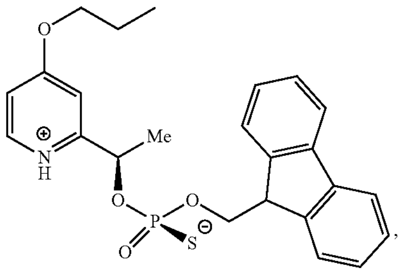

(R, $R_P$)

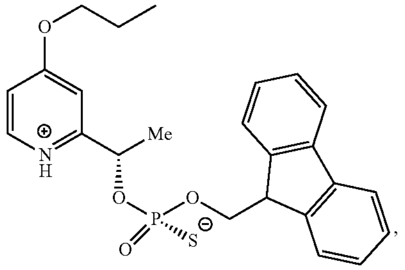

and (S, $S_P$)

-continued

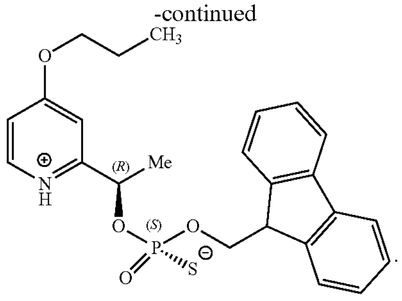

(R, $S_P$)

11. A process for the synthesis of a chiral phosphorothioate, wherein a compound according to claim 1 is used in the synthesis process; and the synthesis process comprises the following steps:

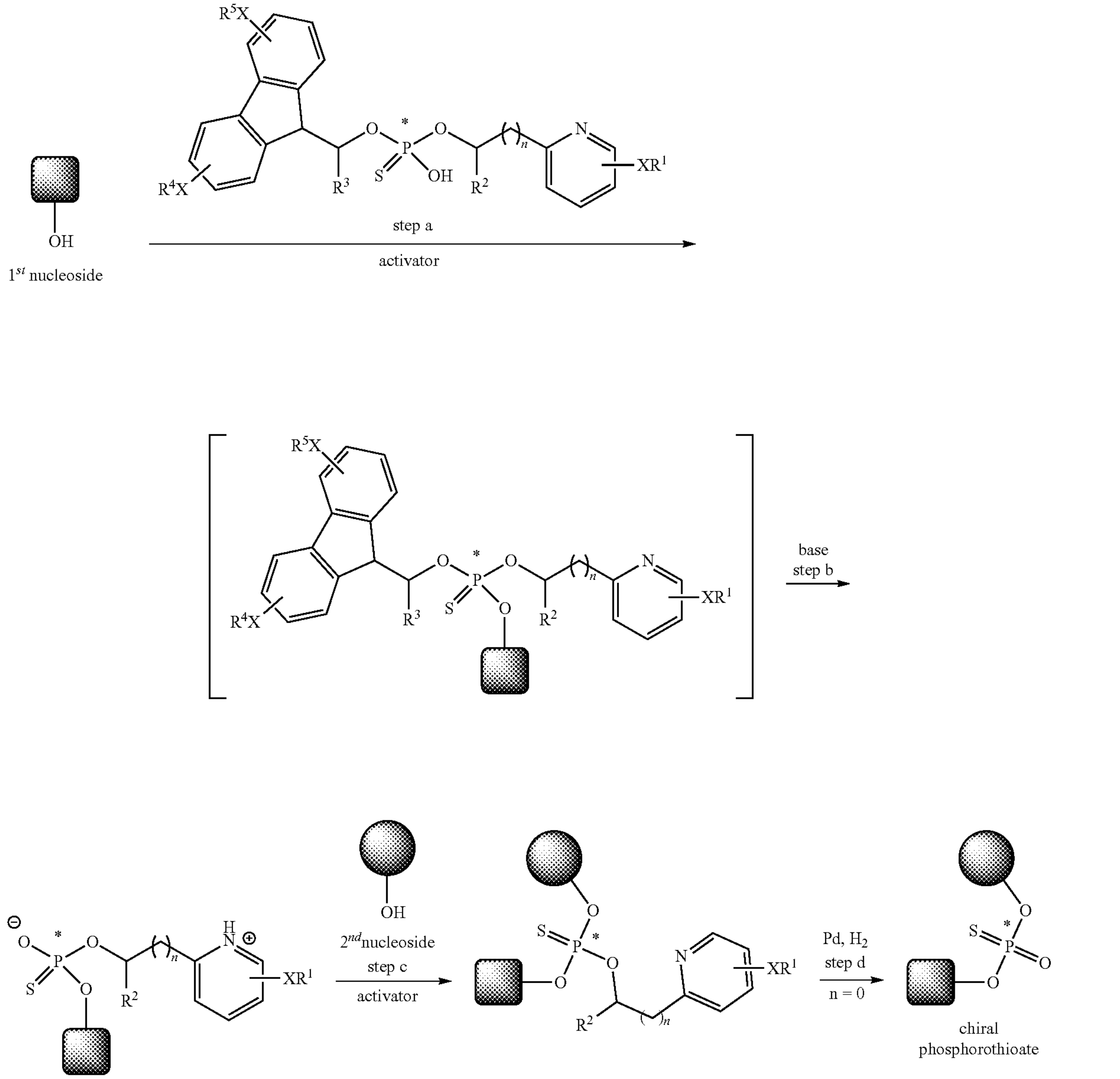

wherein in step a) the first nucleoside is coupled with a compound according to claim 1.

12. A process for the synthesis of a chiral phosphorothioate wherein the synthesis process comprises the following steps:

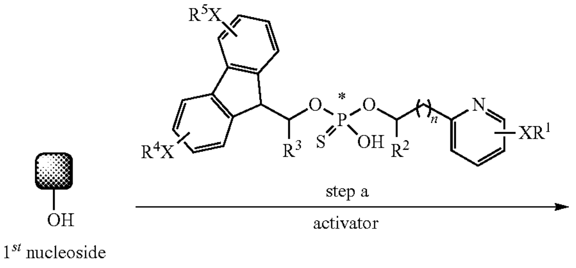

-continued

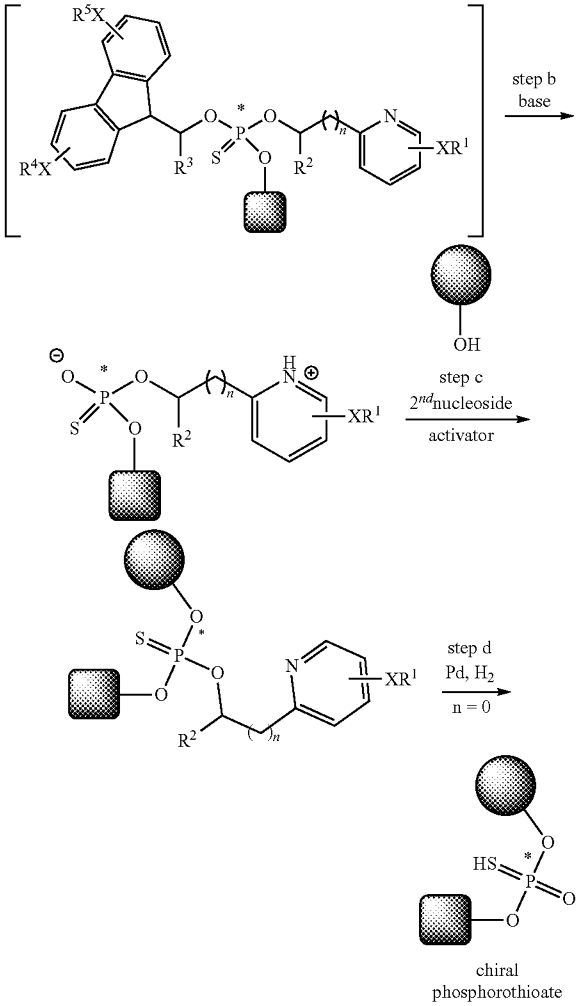

wherein:

(i) in step a) the first nucleoside is coupled with a compound according to claim 1, wherein n is 0, $R^2$ is $CH_3$ and $R^3$ is H;

(ii) in step b) the fluorenylmethyl group is removed from the product resulting from step a);

(iii) in step c) the product resulting from step b) is coupled with a second nucleoside; and (iv) in step d) the 1 (-2-pyridinyl) ethyl group is removed from the product of step c), thereby producing the chiral phosphorothioate.

13. A process according to claim 12, wherein in step a) DMOCP is used as the activator.

14. A process according to claim 12, wherein the base in step b) is selected from the group consisting of DBU, TMG, t-$BuNH_2$ and trialkyl amines.

15. A process according to claim 12, wherein in step c) DMOCP is used as the activator.

16. A process for the synthesis of a chiral phosphorothioate, wherein the synthesis process comprises the following steps:

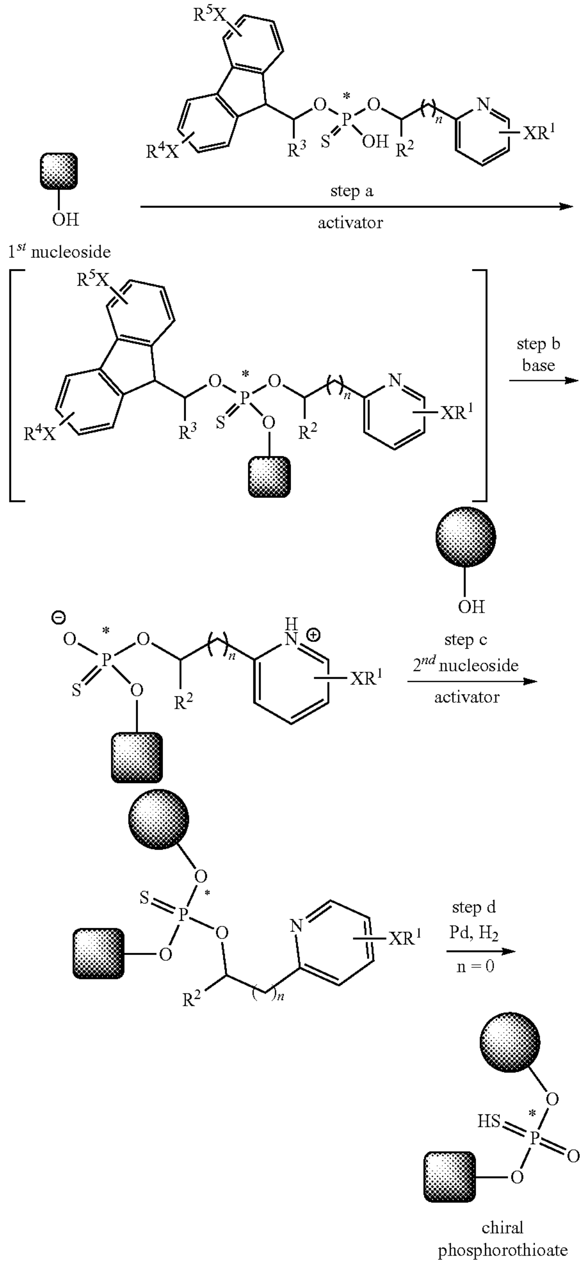

wherein (i) in step a) the first nucleoside is coupled with a compound according to claim 6;

(ii) in step b) the fluorenylmethyl group is removed from the product resulting from step a), (iii) in step c) the product resulting from step b) is coupled with a second nucleoside, and (iv) in step d) the 1(-2-pyridinyl) ethyl group is removed from the product resulting from step c), thereby producing the chiral phosphorothioate.

* * * * *